(12) United States Patent
Lau

(10) Patent No.: US 7,064,185 B2
(45) Date of Patent: Jun. 20, 2006

(54) ANTIBODY FOR HUMAN CYR61

(75) Inventor: Lester F. Lau, Chicago, IL (US)

(73) Assignee: Munin Corporation, Chicago, IL (US)

( * ) Notice: Subject to any disclaimer, the term of this patent is extended or adjusted under 35 U.S.C. 154(b) by 274 days.

(21) Appl. No.: 10/053,753

(22) Filed: Jan. 22, 2002

(65) Prior Publication Data

US 2002/0150986 A1 Oct. 17, 2002

Related U.S. Application Data

(63) Continuation of application No. 09/142,569, filed as application No. PCT/US97/04193 on Mar. 14, 1997, now Pat. No. 6,413,735.

(60) Provisional application No. 60/013,958, filed on Mar. 15, 1996.

(51) Int. Cl.
C07K 1/00 (2006.01)
C07K 14/00 (2006.01)
A61K 39/395 (2006.01)
A61K 39/40 (2006.01)

(52) U.S. Cl. ............... 530/351; 424/130.1; 424/178.1; 424/184; 530/387.1; 530/402

(58) Field of Classification Search ............. 536/23.53, 536/23.4; 530/387.1, 402, 351; 424/130.1, 424/178.1, 184.1
See application file for complete search history.

(56) References Cited

U.S. PATENT DOCUMENTS

| 4,554,101 | A | | 11/1985 | Hopp |
|---|---|---|---|---|
| 5,408,040 | A | | 4/1995 | Grotendorst et al. |
| 5,565,332 | A | * | 10/1996 | Hoogenboom et al. .... 435/69.1 |
| 5,945,300 | A | | 8/1999 | Li et al. |
| 6,008,022 | A | | 12/1999 | Su et al. |
| 6,149,916 | A | | 11/2000 | Grotendorst et al. |
| 6,150,101 | A | | 11/2000 | Grotendorst et al. |

FOREIGN PATENT DOCUMENTS

| AU | 2329697 A | 10/1997 |
|---|---|---|
| AU | 733382 B2 | 5/2001 |
| CA | 2248549N A1 | 9/1997 |
| CA | 0888452 A2 | 1/1999 |
| EP | 0 495 674 | 7/1992 |
| JP | 2000506732 T | 6/2000 |
| WO | WO 96/01896 | 1/1996 |
| WO | WO 97/33995 A | 9/1997 |
| WO | WO 9733995 A2 | 9/1997 |

OTHER PUBLICATIONS

Jay et al., Oncogene 14:1753-1757, 1997.*
Kireeva et al. Exp Cel Research 233:63-77, 1997.*
Latinkic et al. NAR 19(12):3261-3267, 1991.*
O'Brian et al. Molecular and Cellualar Biology 10(7):3569-77, Jul. 1990.
G.D. Phillips et al., Natl.Library of Medicine, "Vascular endothelial growth factor(rhVEGF165) stimulates direct angiogenesis in the rabbit cornea," in vivo Nov.-Dec. 1994,8(6):abstract.
T.Kanoh et al., Natl. Library of Medicine, "Suppression of in vivo tumor-induced angiogenesis by the protein-bound polysaccharide PSK," in vivo Mar.-Apr. 1994, 8(2):abstract.
G.D. Phillips et al., Natl.Library of Medicine, "Platelet derived wound healing factors (PDWHF) accelerate and augment wound healing angiogenesis in the rat," in vivo Mar.-Apr. 1994,8(2):abstract.
D.S.Grant et al., Annals New York Academy of Sciences," Role of Basement Membranes in Vascular Development," (1990),588:61-72.
A.E.Canfield et al., Journal of Cell science,"Evidence that tenascin and thrombospondin-1 modulate sprouting of endothelial cells," Feb. 1995, 108,pp. 797-809.
M.L. Kireeva et al., Molecular and Cellular Biology, "Cyr61, a Product of a growth Factor-Inducible immediate-early gene, promotes cell proliferation, migration, and adhesion," Apr. 1996, vol. 16, No. 4, pp. 1326-1334.
A.M. Babic et al., Proc. Natl.Acad.Sci . USA,"Cyr61, a product of a growth factor-inducible immediate early gene, promotes agiogenesis and tumor growth," May 1998, vol. 95, pp. 6355-6360.

(Continued)

Primary Examiner—Joseph Woitach
(74) Attorney, Agent, or Firm—Howrey LLP; David W. Clough

(57) ABSTRACT

Polynucleotides encoding mammalian ECM signalling molecules affecting the cell adhesion, migration, and proliferation activities characterizing such complex biological processes as angiogenesis. chondrogenesis, and oncogenesis, are provided. The polynucleotide compositions include DNAs and RNAs comprising part, or all, of an ECM signalling molecule coding sequence, or biological equivalents. Polypeptide compositions are also provided. The polypeptide compositions comprise mammalian ECM signalling molecules, peptide fragments, inhibitory peptides capable of interacting with receptors for ECM signalling molecules, and antibody products recognizing Cyr61. Also provided are methods for producing mammalian ECM signalling molecules. Further provided are methods for using mammalian ECM signalling molecules to screen for, and/or modulate, disorders associated with angiogenesis, chondrogenesis, and oncogenesis: ex vivo methods for using mammalian ECM signalling molecules to prepare blood products are also provided.

12 Claims, 1 Drawing Sheet

OTHER PUBLICATIONS

J.U. Bowie et al., Science, "Deciphering the message in protein sequences:tolerance to amino acid substitutions," Mar. 1990, vol. 247, pp. 1306-1310.

J.T. Ngo et al., Protein Folding Problem and Teriay Structure Prediction, "Computational complexity, protein structure prediction, and the levinthal paradox, "14:491-495.

J.A. Parsons, Natl.Institute for Medical Research, "Peptide Hormones," Jun. 1976, pp. 5-7.

Adra, C.N. et al., "Cloning and expression of the mouse pgk-1 gene and the neucleotide sequence of its promoter," Gene, 60:65-74 (1987).

Ahrens, P.B. et al., "Stage-Related Capacity for Limb Chondrogenesis in Cell Culture," Developmental Biology, 60:69-82 (1977).

Bradham, D.M. et al., "Connective Tissue Growth Factor: a Cysteine-rich Mitogen Secreted by Human Vascular Endothelial Cells Is Related to the SRC-induced Immediate Early Gene Product CEF-10," Journal Cellular Biology, 114(6):1285-1294 (Sep., 1991).

Fajardo, L.F. et al., "Methods in Laboratory Investigation: The Disc Angiogenesis System," Laboratory Investigation, 58(6):718-724 (1988).

Greenberger, J.S. et al., "Demonstration of permanent factor-dependent multipotential (erythroid/neutrophil/basophol) hematopoietic progenitor cell lines," Proc. Natl. Acad. Sci. (USA), 80:2931-2935 (May,1983).

Hartzell, S. et al., "A Growth Factor-Responsive Gene of Murine BALB/c 3T3 Cells Encodes a Protein Homologous to Human Tissue Factor," Molecular and Cellular Biology, 9(6):2567-2573 (Jun., 1989).

Joliot, V. et al., "Proviral Rearrangements and Overexpression of a New Cellular Gene (nov) in Myeloblastosis-Associated Virus Type 1-Induced Nephroblastomas," Molecular and Cellular Biology, 12(1):10-21 (Jan., 1992).

Latinkic, B.V. et al., "Promoter function and structure of the growth factor-inducible immediate early gene cyr61," Nucleic Acids Research, 19(12):3261-3267 (1991).

Lau, L.F. et al., "Identification of a set of genes expressed during the G0-G1 transition of cultured mouse cells," EMBO Journal, 4(12):3145-3151 (1985).

Lau, L.F. "Growth factors and growth control," Current Opinion in Cell Biology, 2:280-284 (1990).

Lau, L.F. et al., "Expression of a set of growth-related immediate early genes in BALB/c 3T3 cells: Coordinate regulation with c-fos or c-myc," Proc. Natl. Acad. Sci. (USA), 84:1182-1186 (Mar., 1987).

Lau, L.F. et al., "Genes induced by serum growth factors," in Molecular Aspects of Cellular Regulation, vol. 6: The hormonal control regulation of gene transcription, Chapter 13, Cohen, P. et al., (eds.), Elsevier Science Publishers B.V., Amersterdam, pp. 257-293 (1991).

O'Brien, T.P. et al., "Expression of cyr61, a Growth Factor-Inducible Immediate-Early Gene," Molecular and Cellular Biology, 10(7):3569-3577 (Jul., 1990).

O'Brien, T.P. et al., "Expression of the Growth Factor-inducible Immediate Early Gene cyr61 Correlates with Chondrogenesis during Mouse Embryonic Development," Cell Growth & Differentiation, 3:645-654 (Sep., 1992).

Ryseck, R-P. et al., "Structure, Mapping, and Expression of fisp-12, a Growth Factor-inducible Gene Encoding a Secreted Cysteine-rich Protein," Cell Growth and Differentiation, 2:225-233 (May, 1991).

Spooncer, E. et al., "Continuous in vitro generation of multipotential stem cell clones form src-infected cultures," Nature, 310:288-230 (Jul., 1984).

Tolsma, S.S. et al., "Peptides Derived from Two Separated Domains of the Matrix Protein Thrombospondin-1 Have Anti-Angiogenic Activity," Journal of Cell Biology, 122(2):497-511 (Jul., 1993).

Yang, G.P. et al., "Cyr61, Product of a Growth Factor-inducible Immediate Early Gene, Is Associated with Extracellular Matrix and the Cell Surface," Cell Growth and Differentiation, 2:351-357 (Jul., 1991).

Yang, G.P., "Biochemical and Functional Analysis of Cyr61, The Product of a Growth Factor-Inducible Immediate Early Gene," Ph.D. Thesis, University of Illinois at Chicago, Chicago, Illinois (1993).

Iwamoto et al., Advances in Experimental Medicine and Biology, 324:141-149 (1992).

Yang, G.P. Dissertaion Abstracts International, 54(8):DA9335171, February, (1994).

O'Brien et al. Cell Growth and Differentiation 3:645-354, (1992).

Bork, P. FEBS letters 327(2):125-130, July, (1993).

Lin et al. Cancer Research 53:2950-2953, July, (1993).

Felch et al., Regional Immunology 4:363-370, (1992).

Mackinnon et al., Invasion Metastasis 12:241-252 (1992).

Wallukar, G. et al. Z. Kardiol., 81:Suppl. 4, 79-83 (1992).

Hoermann, et al. Acta Endocrinologica 111:487-493 (1986).

Jedsadayanmata et al. "Activation-dependent adhision of human platelets to Cyr 61 and Fisp12/Mouse Connective Tissue Growth Factor is Mediated Through Integrin Alpha IIB beta3," Journal of Biol. Chem. 274 (34):24321-24327 (1999).

Chen N. et al. "Adhesion of human skin fibroblasts to Cyr61 is mediated through integrin alpha6beta1 and cell surface heparin sulfate proteoglycans," Journal of Bio. Chem. 275 (32):24953-24961 (2000).

* cited by examiner

```
Cyr61    M--SSSTFRTLAVAVTLLHL--TRLALST-CPAAC--HCPLE-APKCAPGVGLVRDGCGRCTCAGGX      58
CEF10    M--GSAGARP-ALAAALLCL--ARLALGSPCPAVC--QCPAA-AEQCAPGVGLVPDGCCGXCTCAK      58
Fisp12   M--LASVAGPISLA-LVLLALCTRPATGQDCSAQC--QCAAEAAPHGPAGVSLSLDGCCCHCTCEX     61
CTGF     M--IAASMGPVRVAFVVLLALCSRPAVGQNCSGPC--RCPDEPAPRCPAGVSLSLDGCCSCTCEX      62
Nov      METGCQGCLFVLLLLLTLRPCEVSGREAACFRPCGGRCPAEP-PRCAPGVPAVLDGCCSCLVCAR      65

Cyr61    QLNEDCSKTQPCDHTKGLECNFGASSTALKGICRAQSEGRPCEYNSKIYQNGESFQPNCKHQCTCI    124
CEF10    QLNEDCSRTQPCDHTKGLECNFGASPAATNGICRAQSEGRPCEYNSKIYQNGESEQPNCKHQCTCI    124
Fisp12   QLGZLCTERDPCDPHKGIFCDFGSPANRKIGVCTAK-DGAPCVFGGSVERSGZSFDSSEKYDCTCL    126
CTGF     QLGZLCTERDPCDPHKGLFCDFGSPANRKIGVCTAK-DGAPCIFGGTVERSGZSFDSSEKYDCTCL    127
Nov      QRGZSCSPLLECDESGGLYCDRGPEDCGGAGICMVL-EGDNCVFDGCCERNCETDDPSEKYDCTCR    130

Cyr61    DGAVGCIPLCPQELSLPNLGCPNPRLVKVSGQCCEEVVCDEDSIK-DSLDD-QDDLLGLDASEVEL    188
CEF10    DGAVGCIPLCPQELSLPNLGCPSPRLVKVPGQCCEEVVCDESKDALPELEGFFSKEFGLDASEGEL    190
Fisp12   DGAVGCTVPLCSMDVRLPSPDCPFPRRVKLPGKCCEEVVCDEPKDRTAVGP-------ALAEYRLED    185
CTGF     DGAVCCCFLCSMDVRLPSPDCPFPRRVKLPGKCCEEVVCDEPKDQTVVGP-------ALAEYRLED    186
Nov      DGQIGCCFLRCNLGLLLPGPDCPFPBKIEVPGECCEKVVCDPRDEVLLGCP-------AMAEYRQBA   189

Cyr61    IRHNELIAIGKGSSLKRLPVFGTEPRVLFNPLHAHCQKCIVQITSESQCSKSCGTGISIKVIRUHP    254
CEF10    IRRNELIAIVKGG-LKCLPVFGSEPQ----SRAFENPKCIVQITSESQCSKTGGTGISIKVIRDNP    251
Fisp12   T--------------FGPDP-------TMGRANCLVQITERSACSKICGKGISIKVIRDBT        225
CTGF     T--------------FGPDP-------IMIRANCLVQITERSACSKICGKGISIKVCDHDMA       226
Nov      T--------------LGIDV-------SDSSANCIECTTERSACSKSCGKCFSIKCINRNQ        229

Cyr61    EGRLVKETKICEVRPCGQPVYSSLKKGKKCSKTKKSPEPVRFTYAGCSSVKCTRPKYCGSCVDCKC    320
CEF10    DCKLIKETRICEVRPCGQPSYASLKKGKKCTCTCKSPSPVRFTYAGCSSVKCKRPKYDGSCVDCRQ    317
Fisp12   FCRLEKQSRLCMVRPCEADLEENIKKGKKCIRTPKIAKPVKFELSGCTSVKICTYRAKFCGVCTDCED   291
CTGF     SCRLEKQSRLCMVRPCEADLEENIKKGKKCIRTPKISKPIKFELSGCTSMKCTYRAKFCGVCTDCED   292
Nov      QCEMVKQTRLCMORPCEM-EEPSDKKGKKCIQTDKSMKAVRFEYKNGTSVQTEKFRYCGLENDGRC   294

Cyr61    CTFLGTRTVKCKFRCEDGEMFSKNVMM-IQSCKCNYRCPHPHEASFRLY--SLFKDIHKFRD       379
CEF10    CTPQQIRTVKIRFRCEDDGETFTKSVMM-IQSCRCNYNCPHANEA-YPFY--RLVNDIHKFRD      376
Fisp12   CTPHRITTLPVEFKCPDGEIMKKN-MCFIKTCAGHYNCPGDNDIFESLYYRKMYGDMA           348
CTGF     CTPHRITTLPVEFKCPDGEVMKKN-MCFIKTLAGHYNCPGDNDIFESLYYRKMYGDMA           349
Nov      CTPHNDKCTIQVEFRCPQGKFLKKP-MMLINTCVGHCNCPQSNNAFFQPLDPMSSEAKI          351
```

FIGURE 1

ANTIBODY FOR HUMAN CYR61

This is a continuation, or prior application Ser. No. 09/142,569, filed Apr. 2, 1999, now U.S. Pat. No. 6,413,735, which is the U.S. National Phase filing (371) of PCT/US97/04193, filed Mar. 14, 1997, and claims priority of U.S. Provisional Application No. 60/013,958, filed Mar. 15, 1996 which is hereby incorporated herewith by reference in its entirety.

FIELD OF THE INVENTION

The present invention is directed to materials and methods involving extracellular matrix signalling molecules—polypeptides involved in cellular responses to growth factors. More particularly, the invention is directed to Cyr61-, Fisp12-, and CTGF-related polynucleotides, polypeptides, compositions thereof, methods of purifying these polypeptides, and methods of using these polypeptides.

BACKGROUND OF THE INVENTION

The growth of mammalian cells is tightly regulated by polypeptide growth factors. In the adult animal, most cells are metabolically active but are quiescent with regard to cell division. Under certain conditions, these cells can be stimulated to reenter the cell cycle and divide. As quiescent cells reenter the active growth and division phases of the cell cycle, a number of specific genes, the immediate early genes, are rapidly activated. Reentry to the active cell cycle is by necessity tightly regulated, since a breakdown of this control can result in uncontrolled growth, frequently recognized as cancer. Controlled reentry of particular cells into the growth phase is essential for such biological processes as angiogenesis (e.g., blood vessel growth and repair), chondrogenesis (e.g., skeletal development and prosthesis integration), oncogenesis (e.g., cancer cell metastasis and tumor neovascularization), and other growth-requiring processes.

Angiogenesis, the formation of new blood vessels from the endothelial cells of preexisting blood vessels, is a complex process which involves a changing profile of endothelial cell gene expression, associated with cell migration, proliferation, and differentiation. Angiogenesis begins with localized breakdown of the basement membrane of the parent vessel. In vivo, basement membranes (primarily composed of laminin, collagen type IV. nidogen/entactin, and proteoglycan) support the endothelial cells and provide a barrier separating these cells from the underlying stroma. The basement membrane also affects a variety of biological activities including cell adhesioen, migration, and growth during development and differentiation.

Following breakdown of the basement membrane, endothelial cells migrate away from the parent vessel into the interstitial extracellular matrix (ECM), at least partially due to chemoattractant gradients. The migrating endothelial cells form a capillary sprout, which elongates. This elongation is the result of migration and proliferation of cells in the sprout. Cells located in the leading capillary tip migrate toward the angiogenic stimulus, but neither synthesize DNA nor divide. Meanwhile, behind these leading tip cells, other endothelial cells undergo rapid proliferation to ensure an adequate supply of endothelial cells for formation of the new vessel. Capillary sprouts then branch at their tips, the branches anastomose or join with one another to form a lumen, the basement membrane is reconstituted, and a vascular connection is established leading to blood flow.

Alterations in at least three endothelial cell functions occur during angiogenesis: 1) modulations of interactions with the ECM, which require alterations of cell-matrix contacts and the production of matrix-degrading proteolytic enzymes; 2) an initial increase and subsequent decrease in endothelial cell migration, effecting cell translocation towards an angiogenic stimulus; and 3) a transient increase in cell proliferation, providing cells for the growing and elongating vessel, with a subsequent return to the quiescent cell state once the vessel is formed. These three functions are realized by adhesive, chemotactic, and mitogenic interactions or responses, respectively. Therefore, control of angiogenesis requires intervention in three distinct cellular activities: 1) cell adhesion, 2) cell migration, and 3) cell proliferation. Another biological process involving a similar complex array of cellular activities is chondrogenesis.

Chondrogenesis is the cellular process responsible for skeletal organization, including the development of bone and cartilage. Chondrogenesis, like angiogenesis, involves the controlled reentry of quiescent cells into the growth phase of the cell cycle. The growth phase transition is associated with altered cell adhesion characteristics, changed patterns of cell migration, and transiently increased cell proliferation. Chondrogenesis involves the initial development of chondrogenic capacity (i.e., the proto-differentiated state) by primitive undifferentiated mesenchyme cells. This stare involves the production of chondrocyte-specific markers without the ability to produce a typical cartilage ECM. Subsequently, the cells develop the capacity to produce a cartilage-specific ECM as they differentiate into chondrocytes. Langille, *Microscop. Res. & Tech.* 28:455–469 (1994). Chondrocyte migration, adhesion, and proliferation then contribute to the development of bony, and cartilaginous, skeleton. Abnormal elaboration of the programmed development of cells participating in the process of chondrogenesis results in skeletal defects presenting problems that range from cosmetic concerns to life-threatening disorders.

Like angioogenesis and chondrogenesis, oncogenesis is characterized by changes in cell adhesion, migration, and proliferation. Metastasizing cancer cells exhibit altered adhesion and migration properties. Establishment of tumorous masses requires increased cell proliferation and the elaboration of the cellular properties characteristic of angiogenesis during the neovascularization of tumors.

Abnormal progression of angiogenesis or chondrogenesis, as well as mere progression of oncogenesis, substantially impairs the quality of life for afflicted individuals and adds to modern health care costs. The features common to these complex biological processes, comprising altered cell adhesion, migration, and proliferation, suggest that agents capable of influencing all three of these cellular activities would be effective in screening for, and modulating, the aforementioned complex biological processes. Although the art is aware of agents that influence individual cellular activities. e.g., integrins and selectins (cell adhesion), chemokines (cell migration). and a variety of growth factors or cytokines (cell proliferation), until recently no agent has been identified that exerts an influence over all three cellular activities in humans.

Murine Cyr61 (CYsteine-Rich protein) is a protein expressed in actively growing and dividing cells that may influence each of these three cellular activities. RNase protection analyses have shown that the gene encoding murine Cyr61, murine Cyr61, is transcribed in the developing mouse embryo. O'Brien et al., *Cell Growth & Diff* 3:645–654 (1992). In situ hybridization analysis showed that expression of cyr61 during mouse embryogenesis is closely correlated with the differentiation of mesenchymal cells, derived from ectoderm and mesoderm, into chondrocytes. In addition, cyr61 is expressed in the vessel walls of the developing circulatory system. These observations indicate that murine cyr61 is expressed during cell proliferation and differentiation, which are characteristics of expression of genes involved in regulatory cascades that control the cell growth cycle.

Further characterization of the Cyr61 polypeptide has been hampered by an inability to purify useful quantities of the protein. Efforts to purify Cyr61 in quantity by overexpression from either eukaryotic or prokaryotic cells typically fail, Yang, *University of Illinois at Chicago, Ph.D. Thesis* (1993). One problem associated with attempting to obtain useful quantities of Cyr61 is the reduction in mammalian growth rates induced by overexpression of Cyr61. Another problem with Cyr61 purification is that the cysteine-rich polypeptide, when expressed in bacterial cells using recombinant DNA techniques, is often found in insoluble protein masses. Nevertheless. Cyr61 has been characterized as a polypeptide of 349 amino acids, containing 39 cysteine residues, a hydrophobic putative N-terminal signal sequence, and potential N-linked glycosylation sites ($Asn_{28}$ and $Asn_{225}$). U.S. Pat. No. 5,408,040 at column 3, lines 41–54, Grotendorst et al. incorporated herein by reference (the '040 Patent).

Recently, proteins related to Cyr61 have been characterized.

For example, a human protein, Connective Tissue Growth Factor (CTGF), has been identified, (See '040 Patent). CTGF is expressed in actively growing cells such as fibroblasts and endothelial cells ('040 Patent, at column 5. lines 62–64), an expression pattern shared by Cyr61. In terms of function. CTGF has been described as a protein growth factor because its primary biological activity has been alleged to be its mitogenicity ('040 Patent, at column 2, lines 25–27 and 53–55). In addition, CTGF reportedly exhibits chemotactic activity. '040 Patent, at column 2. lines 56–59. In terms of structure, the polynucleotide sequence encoding CTGF, and the amino acid sequence of CTGF, have been published. '040 Patent, SEQ ID NO: 7 and SEQ ID NO: 8. respectively.

Another apparently related protein is the mouse protein Fisp12 (Fibroblast Secreted Protein). Fisp12 has been subjected to amino acid sequence analysis, revealing a primary structure that is rich in cysteines. Ryseck et al., *Cell Growth & Diff* 2:225–233 (1991), incorporated herein by reference. The protein also possesses a hydrophobic N-terminal sequence suggestive of the signal sequence characteristic of secreted proteins.

Sequence analyses involving Cyr61, Fisp12, CTGF, and other proteins, have contributed to the identification of a family of cysteine-rich secreted proteins. Members of the family share similar primary structures encoded by genes exhibiting similar sequences. Each of the proteins in this emerging family is further characterized by the presence of a hydrophobic N-terminal signal sequence and 38 cysteine residues in the secreted forms of the proteins. Members of the family identified to date include the aforementioned Cyr61 (human and mouse), Fisp12 (mouse), and CTGF (the human ortholog of Fisp12), as well as CEF10 (chicken), and Nov (avian).

One of several applications for a purified protein able to affect cell adhesion, migration, and proliferation properties involves the development of stable, long term ex vivo hematopoietic stem cell cultures. Patients subjected to high-dose chemotherapy have suppressed hematopoiesis: expansion of stem cells, their maturation into various hematopoietic lineages. and mobilization of mature cells into circulating blood routinely take many weeks to complete. For such patients, and others who need hematopoietic cell transplantation, introduction into those patients of autologous stem cells that have been manipulated and expanded in culture is advantageous. Such hematopoietic stem cells (HSC) express the CD34 stem cell antigen, but do not express lineage commitment antigens. These cells can eventually give rise to all blood cell lineages (e.g., erythrocytes, lymphocytes, and myelocytes).

Hematopoietic progenitor cells that can initiate and sustain long term cultures (i.e. long term culture system-initiating cells or LTC-IC) represent a primitive population of stem cells. The frequency of LTC-IC has been estimated at only 1–2 per $10^4$ cells in normal human marrow and only about 1 per 50–100 cells in a highly purified $CD34^+$ subpopulation. Thus, it would be useful to have methods and systems for long term cell culture that maintain and expand primitive, pluripotent human HSC to be used for repopulation of the hematopoietic system in vivo.

Cell culture models of hematopoiesis have revealed a multitude of cytokines that appear to play a role in the hematopoietic process, including various colony stimulating factors, interleukins, stem cell factor, and the c-kit ligand. However, in ex vivo cultures, different combinations of these cytokines favor expansion of different sets of committed progenitors. For example, a factor in cord blood plasma enhanced expansion of granulocyte-erythroid-macrophage-megakaryocyte colony forming unit (CFU-GEMM) progenitors, but expansion in these cultures favored the more mature subsets of cells. Therefore, it has been difficult to establish a culture system that mimics in vivo hematopoiesis.

An HSC culture system should maintain and expand a large number of multi- or pluripotent stem cells capable of both long term repopulation and eventual lineage commitment under appropriate induction. However, in most ex vivo culture systems, the fraction of the cell population comprised of LTC-IC decreases steadily with continued culturing, often declining to 20% of their initial level after several weeks, as the culture becomes populated by more mature subsets of hematopoietic progenitor cells that are no longer pluripotent. Moreover, the proliferative capacity exhibited by individual LTC-IC may vary extensively. Thus, a need exists in the art for HSC culture systems comprising biological agents that maintain or promote the pluripotent potential of cells such as LTC-IC cells. In addition to a role in developing ex vivo HSC cultures, biological agents affecting cell adhesion, migration, and proliferation are useful in a variety of other contexts.

Proteins that potentiate the activity of mitogens but have no mitogenic activity themselves may play important roles as signalling molecules in such processes as hematopoiesis. Moreover, these signalling proteins could also serve as probes in the search for additional mitogens, many of which have not been identified or characterized. Several biological factors have been shown to potentiate the mitogenic activity of other factors, without being mitogenic themselves. Some of these potentiators are associated with the cell surface and/or extracellular matrix. Included in this group are a secreted basic Fibroblast Growth Factor-binding protein (bFGF-binding protein), the basal lamina protein perlecan, and the Human Immunodeficiency Virus-1 TAT protein, each protein being able to promote bFGF-induced cell proliferation and angiogenesis. Also included in this group of mitogen potentiators are thrombospondin, capable of activating a latent form of Transforming Growth Factor-β, and an unidentified secreted growth-potentiating factor from vascular smooth muscle cells (Nakano et al., *J. Biol. Chem.* 270:5702–5705 [1995]), the latter factor being required for efficient activation of Epidermal Growth Factor- or thrombin-induced DNA synthesis. Further, the B cell stimulatory factor-1/interleukin-4, a T cell product with no demonstrable mitogenic activity, is able to 1) enhance the proliferative response of granulocyte-macrophage progenitors to granulocyte-colony stimulating factor. 2) enhance the proliferative response of erythroid progenitors to erythropoietin, and 3) together with erythropoietin, induce colony formation by multipotent progenitor cells. Similarly, interleukin-7 enhanced stem cell factor-induced colony formation by primitive murine bone marrow progenitors, although interleukin-7 had no proliferative effect by itself. In addition, lymphocyte growth enhancing factor (LGEF) was found to enhance mitogen-stimulated human peripheral blood lymphocyte (PBL) or purified T cell proliferation in a dose-dependent fashion. LGEF alone did not stimulate PBL or T cell proliferation.

Therefore, a need continues to exist for biological agents capable of exerting a concerted and coordinated influence on one or more of the particularized functions collectively characterizing such complex biological processes as angiogenesis, chondrogenesis, and oncogenesis. In addition, a need persists in the art for agents contributing to the reproduction of these in vivo processes in an ex vivo environment, e.g., the development of HSC cultures. Further, there continues to be a need for tools to search for the remaining biological components of these complex processes, e.g., mitogen probes, the absence of which impedes efforts to advantageously modulate and thereby control such processes.

SUMMARY OF THE INVENTION

The present invention provides extracellular matrix (ECM) signalling molecule-related materials and methods. In particular, the present invention is directed to polynucleotides encoding ECM signalling molecules and fragments or analogs thereof, ECM signalling molecule-related polypeptides and fragments, analogs, and derivatives thereof, methods of producing ECM signalling molecules, and methods of using ECM signalling molecules.

One aspect of the present invention relates to a purified and isolated polypeptide comprising an ECM signalling molecule. The polypeptides according to the invention retain at least one biological activity of an ECM signalling molecule, such as the ability to stimulate cell adhesion, cell migration, or cell proliferation; the ability to modulate angiogenesis. chondrogenesis, or oncogenesis: immunogenicity or the ability to elicit an immune response, and the ability to bind to polypeptides having specific binding sites for ECM signalling molecules including antibodies and integrins. The polypeptides may be native or recombinant molecules. Further, the invention comprehends full-length ECM signalling molecules, and fragments thereof. In addition, the polypeptides of the invention may be underivatized, or derivatized in conformity with a native or non-native derivatization pattern. The invention further extends to polypeptides having a native or naturally occurring amino acid sequence, and variants (i.e., polypeptides having different amino acid sequences), analogs (i.e., polypeptides having a non-standard amino acid or other structural variation from the conventional set of amino acids) and homologs (i.e., polypeptides sharing a common evolutionary ancestor with another polypeptide) thereof. Polypeptides that are covalently linked to other compounds, such as polyethylene glycol, or other proteins or peptides, i.e. fusion proteins, are contemplated by the invention.

Exemplary ECM signalling molecules include mammalian Cyr61, Fisp12, and CTGF polypeptides. Beyond ECM signalling molecules, the invention includes polypeptides that specifically bind an ECM signalling molecule of the invention, such as the aforementioned antibody products. A wide variety of antibody products fall within the scope of the invention, including polyclonal and monoclonal antibodies, antibody fragments, chimeric antibodies, CDR-grafted antibodies, "humanized" antibodies, and other antibody forms known in the art. Other molecules such as peptides, carbohydrates or lipids designed to bind to an active site of the ECM molecules thereby inhibiting their activities are also contemplated by the invention. However molecules such as peptides that enhance or potentiate the activities of ECM molecule are also within the scope of the invention. The invention further extends to a pharmaceutical composition comprising a biologically effective amount of a polypeptide and a pharmaceutically acceptable adjuvant, diluent or carrier, according to the invention. A "biologically effective amount" of the biomaterial is an amount that is sufficient to result in a detectable response in the biological sample when compared to a control lacking the biomaterial.

Another aspect of the invention relates to a purified and isolated polynucleotide comprising a sequence that encodes a polypeptide of the invention. A polynucleotide according to the invention may be DNA or RNA, single- or double-stranded, and may be may purified and isolated from a native source, or produced using synthetic or recombinant techniques known in the art. The invention also extends to polynucleotides encoding fragments, analogs (i.e., polynucleotides having a non-standard nucleotide), homologs (i.e., polynucleotides having a common evolutionary ancestor with another polynucleotide), variants (i.e., polynucleotides differing in nucleotide sequence), and derivatives (i.e., polynucleotides differing in a structural manner that does not involve the primary nucleotide sequence) of ECM molecules. Vectors comprising a polynucleotide according to the invention are also contemplated. In addition, the invention comprehends host cells transformed or transfected with a polynucleotide or vector of the invention.

Other aspects of the invention relate to methods for making or using the polypeptides and/or polynucleotides of the invention. A method for making a polypeptide according to the invention comprises expressing a polynucleotide encoding a polypeptide according to the present invention in a suitable host cell and purifying the polypeptide. Other methods for making a polypeptide of the invention use techniques that are known in the art such as the isolation and purification of native polypeptides or the use of synthetic techniques for polypeptide production. In particular, a method of purifying an ECM signalling molecule such as human Cyr61 comprises the steps of identifying a source containing human Cyr61, exposing the source to a human Cyr61-specific biomolecule that binds Cyr61 such as an anti-human Cyr61 antibody, and eluting the human Cyr61 from the antibody or other biomolecule, thereby purifying the human Cyr61.

Another aspect of the invention is a method of screening for a modulator of angiogenesis comprising the steps of: (a) contacting a first biological sample capable of undergoing angiogenesis with a biologically effective (i.e., angiogenically effective) amount of an ECM signalling molecule-related biomaterial and a suspected modulator (inhibitor or potentiator); (b) separately contacting a second biological sample with a biologically effective amount of an ECM signalling molecule-related biomaterial, thereby providing a control: (c) measuring the level of angiogenesis resulting from step (a) and from step (b); and (d) comparing the levels of angiogenesis measured in step (c), whereby a modulator of angiogenesis is identified by its ability to alter the level of angiogenesis when compared to the control of step (b). The modulator may be either a potentiator or inhibitor of angiogenesis and the ECM signalling molecule-related biomaterial includes, but is not limited to, Cyr61, and fragments, variants, homologs, analogs, derivatives, and antibodies thereof.

The invention also extends to a method of screening for a modulator of angiogenesis comprising the steps of: (a) preparing a first implant comprising Cyr61 and a second implant comprising Cyr61 and a suspected modulator of Cyr61 angiogenesis; (b) implanting the first implant in a first cornea of a test animal and the second implant in a second cornea of the test animal: (c) measuring the development of blood vessels in the first and second corneas: and (d) comparing the levels of blood vessel development measured in step (c), whereby a modulator of angiogenesis is identified by its ability to alter the level of blood vessel development in the first cornea when compared to the blood vessel development in the second cornea.

Another aspect of the invention relates to a method of screening for a modulator of chondrogenesis comprising the steps of: (a) contacting a first biological sample capable of undergoing chondrogenesis with a biologically effective (e.g. chondrogenically effective) amount of an ECM signalling molecule-related biomaterial and a suspected modulator; (b) separately contacting a second biological sample capable of undergoing chondrogenesis with a biologically effective amount of an ECM signalling molecule-related biomaterial, thereby providing a control; (c) measuring the level of chondrogenesis resulting from step (a) and from step (b); and (d) comparing the levels of chondrogenesis measured in step (c), whereby a modulator of chondrogenesis is identified by its ability to alter the level of chondrogenesis when compared to the control of step (b). The modulator may be either a promoter or an inhibitor of chondrogenesis; the ECM signalling molecules include those defined above and compounds such as mannose-6-phosphate, heparin, and tenascin.

The invention also relates to an in vitro method of screening for a modulator of oncogenesis comprising the steps of: (a) inducing a first tumor and a second tumor; (b) administering a biologically effective amount of an ECM signalling molecule-related biomaterial and a suspected modulator to the first tumor; (c) separately administering a biologically effective amount of an ECM signalling molecule-related biomaterial to the second tumor, thereby providing a control; (d) measuring the level of oncogenesis resulting from step (b) and from step (c); and (e) comparing the levels of oncogenesis measured in step (d), whereby a modulator of oncogenesis is identified by its ability to alter the level of oncogenesis when compared to the control of step (c). Modulators of oncogenesis contemplated by the invention include inhibitors of oncogenesis. Tumors may be induced by a variety of techniques including, but not limited to, the administration of chemicals, e.g., carcinogens, and the implantation of cancer cells. A related aspect of the invention is a method for treating a solid tumor comprising the step of delivering a therapeutically effective amount of a Cyr61 inhibitor to an individual, thereby inhibiting the neovascularization of the tumor. Inhibitors include, but are not limited to. inhibitor peptides such as peptides having the "RGD" motif, and cytotoxins, which may be free or attached to molecules such as Cyr61.

Yet another aspect of the invention is directed to a method of screening for a modulator of cell adhesion comprising the steps of: (a) preparing a surface compatible with cell adherence; (b) separately placing first and second biological samples capable of undergoing cell adhesion on the surface; (c) contacting a first biological sample with a suspected modulator and a biologically effective amount of an ECM signalling molecule-related biomaterial selected from the group consisting of a human Cyr61, a human Cyr61 fragment, a human Cyr61 analog, and a human Cyr61 derivative; (d) separately contacting a second biological sample with a biologically effective amount of an ECM signalling molecule-related biomaterial selected from the group consisting of a human Cyr61, a human Cyr61 fragment, a human Cyr61 analog, and a human Cyr61 derivative, thereby providing a control; (e) measuring the level of cell adhesion resulting from step (c) and from step (d); and (f) comparing the levels of cell adhesion measured in step (e), whereby a modulator of cell adhesion is identified by its ability to alter the level of cell adhesion when compared to the control of step (d).

The invention also extends to a method of screening for a modulator of cell migration comprising the steps of: (a) forming a gel matrix comprising Cyr61 and a suspected modulator of cell migration: (b) preparing a control gel matrix comprising Cyr61; (c) seeding endothelial cells capable of undergoing cell migration onto the gel matrix of step (a) and the control gel matrix of step (b); (d) incubating the endothelial cells; (e) measuring the levels of cell migration by inspecting the interior of the gel matrix and the control gel matrix for cells: (f) comparing the levels of cell migration measured in step (e), whereby a modulator of cell migration is identified by its ability to alter the level of cell migration in the gel matrix when compared to the level of cell migration in the control gel matrix. The endothelial cells include, but are not limited to, human cells, e.g., human microvascular endothelial cells. The matrix may be formed from gelling materials such as Matrigel, collagen, or fibrin or combinations thereof.

Another aspect of the invention is directed to an in vitro method of screening for cell migration comprising the steps of: (a) forming a first gelatinized filter and a second gelatinized filter, each filter having two sides; (b) contacting a first side of each the filter with endothelial cells, thereby adhering the cells to each the filter: (c) applying an ECM signalling molecule and a suspected modulator of cell migration to a second side of the first gelatinized filter and an ECM signalling molecule to a second side of the second gelatinized filter; (d) incubating each the filter; (e) detecting cells on the second side of each the filter, and (f) comparing the presence of cells on the second side of the first gelatinized filter with the presence of cells on the second side of the second gelatinized filter, whereby a modulator of cell migration is identified by its ability to alter the level of cell migration measured on the first gelatinized filter when compared to the cell migration measured on the second gelatinized filter. The endothelial cells are defined above. The ECM signalling molecules extend to human Cyr61 and each of the filters may be placed in apparatus such as a Boyden chamber, including modified Boyden chambers.

The invention also embraces an in vivo method of screening for a modulator of cell migration comprising the steps of: (a) removing a first central portion of a first biocompatible sponge and a second central portion of a second biocompatible sponge; (b) applying an ECM signalling molecule and a suspected modulator to the first central portion and an ECM signalling molecule to the second central portion; (c) reassociating the first central portion with said first biocompatible sponge and said second central portion with the second biocompatible sponge; (d) attaching a first filter to a first side of the first biocompatible sponge and a second filter to a second side of the first biocompatible sponge; (e) attaching a third filter to a first side of the second biocompatible sponge and a fourth filter to a second side of the second biocompatible sponge; (f) implanting each of the biocompatible sponges, each biocompatible sponge comprising the central portion and the filters, in a test animal; (e) removing each the sponge following a period of incubation; (f) measuring the cells found within each of the biocompatible sponges; and (g) comparing the presence of cells in the first biocompatible sponge with the presence of cells in the second biocompatible sponge, whereby a modulator of cell migration is identified by its ability to alter the level of cell migration measured using the first biocompatible sponge when compared to the cell migration measured using the second biocompatible sponge. ECM signalling molecules include, but are not limited to, human Cyr61; the ECM signalling molecule may also be associated with Hydron. In addition, the in vivo method of screening for a modulator of cell migration may include the step of providing a radiolabel to the test animal and detecting the radiolabel in one or more of the sponges.

Another aspect of the invention relates to a method for modulating hemostasis comprising the step of administering an ECM signalling molecule in a pharmaceutically acceptable adjuvant, diluent or carrier. Also, the invention extends to a method of inducing wound healing in a tissue comprising the step of contacting a wounded tissue with a biologically effective amount of an ECM signalling molecule, thereby promoting wound healing. The ECM signalling molecule may be provided in the form of an ECM signalling molecule polypeptide or an ECM signalling molecule nucleic acid, e.g., using a gene therapy technique. For example, the nucleic acid may comprise an expression control sequence operably linked to an ECM signalling molecule which is then introduced into the cells of a wounded tissue. The expression of the coding sequence is controlled, e.g., by using a tissue-specific promoter such as the K14 promoter operative in skin tissue to effect the controlled induction of wound healing. The nucleic acid may include a vector such as a Herpesvirus, an Adenovirus, an Adeno-associated Virus, a Cytomegalovirus, a Baculovirus, a retrovirus, and a Vaccinia Virus. Suitable wounded tissues for treatment by this method include, but are not limited to, skin tissue and lung epithelium. A related method comprises administering a biologically effective amount of an ECM signalling molecule. e.g. Cyr61, to an animal to promote organ regeneration. The impaired organ may be the result of trauma, e.g. surgery, or disease. Another method of the invention relates to improving the vascularization of grafts. e.g., skin grafts. Another method of the invention is directed to a process for promoting bone implantation, including bone grafts. The method for promoting bone implantation comprises the step of contacting a bone implant or receptive site with a biologically effective (i.e., chondrogenically effective) amount of an ECM signalling molecule. The contacting step may be effected by applying the ECM signalling molecule to a biocompatible wrap such as a biodegradable gauze and contacting the wrap with a bone implant, thereby promoting bone implantation. The bone implants comprise natural bones and fragments thereof, as well as inanimate natural and synthetic materials that are biocompatible, such as prostheses. In addition to direct application of an ECM signalling molecule to a bone, prosthesis, or receptive site, the invention contemplates the use of matrix materials for controlled release of the ECM signalling molecule, in addition to such application materials as gauzes.

Yet another aspect of the invention relates to a method of screening for a modulator of cell proliferation comprising the steps of: (a) contacting a first biological sample capable of undergoing cell proliferation with a suspected modulator and a biologically effective (i.e., mitogenically effective) amount of an ECM signalling molecule-related biomaterial selected from the group consisting of a human Cyr61, a human Cyr61 fragment, a human Cyr61 analog, and a human Cyr61 derivative; (b) separately contacting a second biological sample capable of undergoing cell proliferation with a biologically effective amount of an ECM signalling molecule-related biomaterial selected from the group consisting of a human Cyr61, a human Cyr61 fragment, a human Cyr61 analog, and a human Cyr61 derivative, thereby providing a control; (c) incubating the first and second biological samples; (d) measuring the level of cell proliferation resulting from step (c); and (e) comparing the levels of cell proliferation measured in step (d), whereby a modulator of cell proliferation is identified by its ability to alter the level of cell adhesion when compared to the control of step (b).

Also comprehended by the invention is a method for expanding a population of undifferentiated hematopoietic stein cells in culture, comprising the steps of: (a) obtaining hematopoietic stem cells from a donor: and (b) culturing said cells under suitable nutrient conditions in the presence of a biologically effective (i.e., hematopoietically effective) amount of Cyr61.

Another method according to the invention is a method of screening for a mitogen comprising the steps of: (a) plating cells capable of undergoing cell proliferation: (b) contacting a first portion of the cells with a solution comprising Cyr61 and a suspected mitogen; (c) contacting a second portion of the cells with a solution comprising Cyr61, thereby providing a control; (c) incubating the cells; (d) detecting the growth of the first portion of cells and the second portion of the cells; and (e) comparing growth of the first and second portions of cells, whereby a mitogen is identified by its ability to induce greater growth in the first portion of cells when compared to the growth of the second portion of cells. The cells include, but are not limited to, endothelial cells and fibroblast cells. Further, the method may involve contacting the cells with a nucleic acid label. e.g., [$^3$H]-thymidine, and detecting the presence of the label in the cells. Another method relates to improving tissue grafting, comprising administering to an animal a quantity of Cyr61 effective in improving the rate of neovascularization of a graft.

Numerous additional aspects and advantages of the present invention will be apparent upon consideration of the following drawing and detailed description.

BRIEF DESCRIPTION OF THE DRAWING

FIG. 1 presents the comparative amino acid sequence of the following members of the cystein-rich protein family of growth-regulating proteins: Cyr61 (SEQ ID NO:2): CEF10 (SEQ ID NO:20); Fisp12 (SEQ ID NO:6); CTGF (SEQ ID NO:8): and Nov (SEQ ID NO:21).

DETAILED DESCRIPTION OF THE INVENTION

In the mouse, the Cyr61 protein has been found to influence cell adhesion, migration, and proliferation. The cyr61 gene, which encodes Cyr61, is an immediate-early gene that is transcriptionally activated by serum growth factors in mouse fibroblasts, Lau et al., *EMBO J.* 4:3145–3151 (1985), incorporated herein by reference; Lau et al., *Proc. Natl. Acad. Sci.* (*USA*) 84:1182–1186 (1987), incorporated herein by reference. The murine cyr61 cDNA coding sequence is set forth in SEQ ID NO: 1. (The human cyr61 cDNA coding sequence is provided in SEQ ID NO: 3). The amino acid sequence of murine Cyr61 is set out in SEQ ID NO: 2. (The human Cyr61 amino acid sequence is presented in SEQ ID NO: 4). Cyr61 is a 41 kDa polypeptide exhibiting 39 cysteine residues, approximately 10% of the 379 amino acids constituting the unprocessed protein. Yang et al., *Cell Growth & Diff* 2:351–357 (1991), incorporated herein by reference. Investigations have revealed that murine Cyr61 binds heparin and is secreted. Yang et al. Consistent with the observed secretion of Cyr61 is the identification of an N-terminal signal sequence in nascent Cyr61, deduced from inspection of the murine cyr61 cDNA sequence. Yang et al. Additionally, Cyr61 is not found in the conditioned medium of cultured cells expressing Cyr61, but is found associated with the extracellular matrix (ECM) and the cell surface. Yang et al. Structurally similar cysteine-rich mammalian proteins have been characterized.

Fisp12. a cysteine-rich murine protein, exhibits structural similarity to Cyr61. The cDNA sequence encoding Fisp12 is set forth in SEQ ID NO: 5; the amino acid sequence of Fisp12 is presented in SEQ ID NO: 6. Murine Fisp12, like Cyr61, influences cell adhesion, proliferation and migration. The human ortholog of Fisp12 is Connective Tissue Growth Factor (CTGF), a protein similar in structure and function to Cyr61, Fisp12, and CTGF, are distinguishable from Cyr61, however. For example, a greater proportion of secreted Fisp12 is found in the culture medium than is the case with Cyr61: a correspondingly lower proportion of Fisp12 is localized in the area of expressing cells (cell surface and nearby extracellular matrix) than is found with Cyr61. Additional similarities and distinctions among the proteins comprising the ECM signalling molecules of the invention will become apparent in the recitations hereinbelow.

The present invention has multiple aspects, illustrated by the following examples. Example 1 describes the cloning of polynucleotides encoding members of the cysteine-rich protein family of ECM signalling molecules: Example 2 describes sequence analyses; Example 3 describes RNA analyses; Example 4 describes the production of transgenic animals; Example 5 describes the expression of Cyr61 polypeptides: Example 6 describes the expression of Fisp12 polypeptides; Example 7 sets out methods of polypeptide purification: Example 8 provides a characterization of the polypeptides of the invention; Example 9 discloses a heparin binding assay for the polypeptide members of the cysteine-rich protein family: Example 10 is directed to receptors for the polypeptides: Example 11 describes anti-ECM signalling molecule antibodies: Example 12 is directed to inhibitory peptides: Example 13 describes cell adhesion and polypeptide-based methods for influencing the process of cell adhesion: Example 14 describes polypeptide-influenced migration of fibroblasts: Example 15 describes the migration of endothelial cells and in vitro assays for migration: Example 16 describes an in vitro assay for inhibitors of endothelial cell migration: Example 17 describes an in vivo assay for endothelial cell migration: Example 18 describes mitogen potentiation by the polypeptides of the invention; Example 19 describes an in vivo cornea assay for angiogenic factors and modulators; Example 20 is directed to methods for influencing blood clotting using the polypeptides of the invention; Example 21 discloses the use of the polypeptides for ex vivo hematopoietic stem cell cultures: Example 22 addresses organ regeneration; Example 23 describes chondrogenesis and the expression of extracellular matrix signalling molecules in mesenchyme cells; Example 24 describes the promotion of cell adhesion in the process of chondrogenesis using the polypeptides of the invention; Example 25 describes chondrogenesis and the influence of the polypeptides of the invention on cell aggregation: Example 26 describes the promotion of cell proliferation by polypeptides of the invention in the process of chondrogenesis; Example 27 addresses methods for using the polypeptides of the invention to affect chondrogenesis; and Example 28 provides genetic approaches to the use of polynucleotides of the invention. These examples are intended to be illustrative of the present invention and should not be construed to limit the scope of the invention.

EXAMPLE 1

Polynucleotide Cloning

A human cyr61 cDNA was isolated from a human placental cDNA library by probing with the murine cyr61cDNA sequence using techniques that are standard in the art. See Sambrook et al., incorporated herein by reference. Isolation of the complete murine cyr61cDNA from a BALB/c 3T3 (ATCC CRL-1658) cDNA library has been described. O'Brien et al., *Mol. Cell. Biol.* 10:3569–3577 (1990), incorporated herein by reference. The nucleotide and deduced amino acid sequences of murine cyr61 are available from the GenBank database under accession number M32490. The nucleotide sequence of murine cyr61 is presented in SEQ ID NO: 1; the murine Cyr61 amino acid sequence is presented in SEQ ID NO: 2.

The human cDNA library was constructed using λgt11 (Promega Corp., Madison. Wis.) as a vector which was transfected into *E. coli* and plated on LB agar. A murine cDNA expression construct cloned in pGEM-2 (O'Brien et al., [1990]), containing the entire murine cyr61 coding sequence [nucleotides 56–1560, using the numbering of O'Brien et al., (1990); see SEQ ID NO: 1] was used as a probe. The mouse cDNA probe was radiolabeled by techniques standard in the art. Sambrook et al. Plaque screenings using the mouse probe were performed using standard techniques.

Sambrook et al.

More particularly, agar plates containing the human cDNA library described above were exposed to nitrocellulose filters (BA85, 82 mm, Schleicher & Schuell, Keene, N.H.) were placed on each plate. After plaque adsorption (approximately 20 minutes), the filters were removed and air dried for approximately 30 minutes. Subsequently, each filter was sequentially submerged for 30–60 seconds in 0.2 M NaOH, 1.5 M NaCl (100 ml); 2×SSC, 0.4 M Tris-HCl, pH 7.4 (100 ml); and 0.2×SSC (100 ml). Filters were then dried at room temperature for approximately 1 hour and subjected to 80° C. under vacuum for 2 hours. Filters were probed with radiolabeled murine cyr61 cDNA.

Alternatively, human cyr61 cDNA clones were identified with probes generated by RT-PCR. In particular, the prove for screening the human placental cDNA library was a PCR fragment generated with degenerate primers by RT-PCR of total RNA from logarithmically growing W138 cells. The primers were derived from the sequences corresponding to the most conserved region of the open reading frame of the mouse cyr61 cDNA. One primer, designated H61-5 [5' GGGAATTCTG(TC)GG(GATC)TG(TC)TG(TC)AA(GA)GT(GC)TG-3' (SEQ ID NO: 18)], contains a degenerate sequence, which, with the exception of the "GGGAATTC" sequence at the 5' end which was used to introduce an EcoRI site, is derived from nucleotides 327–346 (sense strand) of the mouse cyr61 sequence set forth in SEQ ID NO: 1. The degeneracies appear in positions corresponding to the third position of codons in SEQ ID NO: 1. The second primer used for PCR amplification of a human cyr61 sequence was designated H61-3 [5'-CCGGATCC(GA)CA(GA)TT(GA)TA(GA)TT(GA)CA-3' (SEQ ID NO: 19)], which, with the exception of the 5' sequence "CCGGATCC" used to introduce a BamHI site, corresponds to the anti-sense strand complementary to nucleotides 1236–1250 of the mouse cyr61 sequence set forth in SEQ ID NO: 1. The degeneracies occur in positions complementary to the third positions of codons in mouse cyr61 as set forth in SEQ ID NO: 1. The amplified cyr61 cDNA was cloned into the pBlueScript SK+ vector (Stratagene, La Jolla, Calif.) and sequenced with a Sequenase II kit (U.S. Biochemicals, Cleveland, Ohio).

Serial screenings of the human placental cDNA library led to the isolation of a clone containing a human cyr61 cDNA. The human cir61 cDNA is approximately 1,500 bp in length. The human cDNA is contained on an EcoRI fragment cloned into the EcoRI site in pGEM-2. As shown in SEQ ID NO: 3. the human cDNA sequence includes the entire coding region for human Cyr61, along with 120 bp of 5' flanking sequence, and about 150 bp of 3' flanking sequence.

The polynucleotides of the invention may be wholly or partially synthetic. DNA or RNA, and single- or double-stranded. Because polynucleotides of the invention encode ECM signalling molecule polypeptides which may be fragments of an ECM signalling molecule protein, the polynucleotides may encode a partial sequence of an ECM signalling molecule. Polynucleotide sequences of the invention are useful for the production of ECM signalling molecules by recombinant methods and as hybridization probes for polynucleotides encoding ECM signalling molecules.

DNA polynucleotides according to the invention include genomic DNAs. cDNAs, and oligonucleotides comprising a coding sequence of an ECM signalling molecule, or a fragment or analog of an ECM signalling molecule, as described above, that retains at least one of the biological activities of an ECM signalling molecule such as the ability to promote cell adhesion, cell migration, or cell proliferation in such biological processes as angiogenesis, chondrogenesis, and oncogenesis, or the ability to elicit an antibody recognizing an ECM signalling molecule.

Other polynucleotides according to the invention differ in sequence from sequences contained within native ECM signalling molecule polynucleotides (i.e., by the addition, deletion, insertion, or substitution of nucleotides) provided the polynucleotides encode a protein that retains at least one of the biological activities of an ECM signalling molecule. A polynucleotide sequence of the invention may differ from a native ECM signalling molecule polynucleotide sequence by silent mutations that do not alter the sequence of amino acids encoded therein. Additionally. polynucleotides of the invention may specify an ECM signalling molecule that differs in amino acid sequence from native ECM signalling molecule sequences or subsequences, as described above. For example, polynucleotides encoding polypeptides that differ in amino acid sequence from native ECM signalling molecules by conservative replacement of one or more amino acid residues, are contemplated by the invention. The invention also extends to polynucleotides that hybridize under standard stringent conditions to polynucleotides encoding an ECM signalling molecule of the invention, or that would hybridize but for the degeneracy of the genetic code. Exemplary stringent hybridization conditions involve hybridization at 42° C. in 50% formamide, 5×SSC. 20 mM Na.PO$_4$, pH 6.8 and washing in 0.2×SSC at 55° C. It is understood by those of skill in the art that variation in these conditions occurs based on the length and GC nucleotide content of the sequences to be hybridized. Formulas standard in the art are appropriate for determining exact hybridization conditions. See Sambrook et al., Molecular Cloning: A Laboratory Manual (Second ed. Cold Spring Harbor Laboratory Press 1989) §§ 9.47–9.51.

ECM signalling molecule polynucleotides comprising RNA are also within the scope of the present invention. A preferred RNA polynucleotide according to the invention is an mRNA of human cyr61. Other RNA polynucleotides of the invention include RNAs that differ from a native ECM signalling molecule mRNA by the insertion, deletion, addition, or substitution of nucleotides (see above), with the proviso that they encode a polypeptide retaining a biological activity associated with an ECM signalling molecule. Still other RNAs of the invention include anti-sense RNAs (i.e., RNAs comprising an RNA sequence that is complementary to an ECM signalling molecule mRNA).

Accordingly, in another embodiment a set of DNA fragments collectively spanning the human cyr61 cDNA were cloned in pGEM-2 and M13 derivatives using methods well known in the art to facilitate nucleotide sequence analyses. The pGEM-2 clones provided substrates for the enzymatic generation of serial deletions using techniques known in the art. This collection of clones, collectively containing a series of DNA fragments spanning various parts of the cyr61cDNA coding region, are useful in the methods of the invention. The resulting series of nested pGEM-2 clones, in turn, provided substrates for nucleotide sequence analyses using the enzymatic chain terminating technique. The fragments are also useful as nucleic acid probes and for preparing Cyr61 deletion or truncation analogs. For example, the cyr61 cDNA clones may be used to isolate cyr61 clones from human genomic libraries that are commercially available, (Clontech Laboratories, Inc., Palo Alto, Calif.). Genomic clones, in turn, may be used to map the cyr61 locus in the human genome, a locus that may be associated with a known disease locus.

Other embodiments involve the polynucleotides of the invention contained in a variety of vectors, including plasmid, viral (e.g., prokaryotic and eukaryotic viral vectors derived from Lambda phage, Herpesviruses, Adenovirus, Adeno-associated viruses, Cytomegalovirus, Vaccinia Virus, the M13-fl-fd family of viruses, retroviruses, Baculovirus, and others), phagemid, cosmid, and YAC (i.e., Yeast Artificial Chromosome) vectors.

Yet other embodiments involve the polynucleotides of the invention contained within heterologous polynucleotide environments. Polynucleotides of the invention have been inserted into heterologous genomes, thereby creating transgenes, and transgenic animals, according to the invention. In particular, two types of gene fusions containing partial murine cyr61 gene sequences have been used to generate transgenic mice. (See below). One type of fused gene recombined the coding sequence of cyr61 with one of three different promoters: 1) the K14 keratin promoter. 2) the β-actin promoter, or 3) the phosphoglycerokinase promoter. Adra et al. *Gene* 60:65–74 (1987). These fusion constructs were generated using standard techniques, as described below in the context of a phosphoglycerokinase promoter (pgk-1)-cyr61 fusion. An XhoI-ScaI genomic DNA fragment containing the entire cyr61coding region and all introns, but lacking the transcription initiation site and polyadenylation signal, was cloned into plasmid pgk/β-gal, replacing the lacZ coding sequence. The resulting construct placed cyr61 under the control of the strong pgk-1 promoter which is active in all cells.

The second type of gene fusion recombined the cyr61 expression control sequences (i.e., promoter) with the *E. coli* β*-galactosidase coding sequence. The cyr*61-lacZ fusion gene was constructed using the following approach. A DNA fragment spanning nucleotides –2065 to +65 relative to the transcription initiation nucleotide was used to replace the pgk-1 promoter (Adra et al., *Gene* 60:65–74 [1987]) in plasmid pgk/β-gal by blunt end cloning. In addition, the polyadenylation signal from the bovine growth hormone gene was cloned into the plasmid containing the fusion gene. The resulting construct. Plasmid 2/lacZ, has the *E. coli* lacZ gene under the transcriptional control of a 2 kb DNA fragment containing the cyr61 promoter. The related plasmid 1.4/lacZ was derived from plasmid 2lacZ by removing about 600 bp of cyr61 DNA found upstream of an AflII site. Also, plasmid 2M/lacZ resembles Plasmid 2/lacZ, except for a C-to-T transition in the CArG Box, created by PCR. These constructs were excised from the vectors by NotI digestion, purified using GeneClean [Bio 101, Inc., La Jolla, Calif.), and used to generate transgenic mice (see below).

A cDNA fragment encoding mouse fisp12 has also been cloned using standard techniques. Ryseck et al., *Cell Growth & Diff:* 2:225–233 (1991), incorporated herein by reference. The cloning was accomplished by ligating an XhoII fragment containing the fisp12 cDNA coding region into Bat2HI-cleaved pBlueBacIII, a baculovirus expression vector (Invitrogen Corp., San Diego, Calif.). Recombinant baculovirus clones were obtained as described in Summers et al., *TX Ag. Exp. Sta., Bulletin* 1555 (1987).

The human ortholog of fisp12, the gene encoding CTGF, was cloned by screening a fusion cDNA library with anti-Platelet-Derived Growth Factor (anti-PDGF) antibodies, as described in U.S. Pat. No. 5,408,040. column 12, line 16. to column 13, line 29, incorporated herein by reference. The screening strategy exploited the immunological cross-reactivity of CTGF and PDGF.

The cloned copies of the Cyr61, fisp12, and ctgf cDNAs provide a ready source for polynucleotide probes to facilitate the isolation of genomic coding regions, as well as allelic variants of the genomic DNAs or cDNAs. In addition, the existing cDNA clones, or clones isolated by probing as described above, may be used to generate transgenic organisms. For example, transgenic mice harboring cyr61 have been generated using standard techniques, as described in the next Example.

A clone, hCyr61 cDNA, containing the human cyr61 cDNA sequence set forth in SEQ ID NO: 3, and a bacterial strain transformed with that clone. *Escherichia coli* DH5α (hCyr61 cDNA), were deposited with the American Type Culture Collection 12301 Parklawn Drive, Rockville, Md. 20852 USA, on Mar. 14. 1997.

EXAMPLE 2

Sequence Analyses

The nucleotide sequence of murine cyr61 has been described, O'Brien et al. (1990); Latinikic et al., *Nucl. Acids Res.* 19:3261–3267 (1991), and is set out herein as SEQ ID NO: 1.

The deduced amino acid sequence of murine Cyr61 has been reported. O'Brien et al. (1990), and is set forth in SEQ ID NO: 2.

The nucleotide sequence of the human cyr61 cDNA was determined using the method of Sanger, as described in Sambrook et al. Sequencing templates were generated by constructing a series of nested deletions from a pGEM-2 human cyr61 cDNA clone, as described in Example 1 above. The human cyr61 cDNA sequence is set forth in SEQ ID NO: 3. The amino acid sequence of human Cyr61 was deduced from the human cyr61 cDNA sequence and is set forth in SEQ ID NO: 4.

A comparison of the mouse and human Cyr61 sequences. presented in SEQ ID NO: 2 and SEQ ID NO: 4, respectively, reveals 91% similarity. Both sequences exhibit an N-terminal signal sequence indicative of a processed and secreted protein; both proteins also contain 38 cysteine residues, distributed throughout both proteins but notably absent from the central regions of both murine and human Cyr61. Notably, the region of greatest sequence divergence between the mouse and human Cyr61 coding regions is this central region free of cysteine residues. However, the 5' untranslated regions of the mouse and human cyr61 cDNAs are even more divergent (67% similarity). In contrast, the 3' untranslated regions are the most similar regions (91% similarity). In overall length, the encoded murine Cyr61 has 379 amino acids; human Cyr61 has 381 amino acids.

A fisp12 cDNA sequence has also been determined and is set out in SEQ ID NO: 5. The amino acid sequence of Fisp12 has been deduced from the fisp12 cDNA sequence and is set forth in SEQ ID NO: 6. A comparison of the amino acid sequences of murine Cyr61 and Fisp12 reveals that the two proteins are 65% identical. The structural similarity of Cyr61 and Fisp12 is consistent with the similar functional properties of the two proteins, described below.

A partial cDNA sequence of CTGF, containing the complete CTGF coding region, has also been determined. The CTGF cDNA sequence was obtained using M13 clones as templates for enzymatic sequencing reactions, as described. '040 Patent, at column 12, line 68 to column 13, line 14 Additional cloning coupled with double-stranded enzymatic sequencing reactions, elucidated the entire sequence of the cDNA encoding CTGF. U.S. Pat. No. 5,408,040, column 14, line 44, to column 15, line 8. incorporated herein by reference. The nucleotide sequence of the cDNA encoding CTGF is presented herein in SEQ ID NO: 7. The deduced amino acid sequence of the cDNA encoding CTGF is presented in SEQ ID NO: 8.

EXAMPLE 3

RNA Analyses

Polynucleotide probes are useful diagnostic tools for angiogenic, and other, disorders correlated with Cyr61 expression because properly designed probes can reveal the location, and level, of cyr61 gene expression at the transcriptional level. The expression of cyr61, in turn, indicates whether or not genes controlling the process of angiogenesis are being expressed at typical, or expected, levels.

Using these tools, the mouse cyr61 mRNA expression pattern was determined using an RNase protection technique. O'Brien et al., (1992). In particular, a 289 nucleotide antisense riboprobe was used that would protect 246 nucleotides of the murine cyr61 mRNA (nucleotides 67 to 313 using the numbering of O'Brien et al.) The assays showed levels of cyr61 mRNA in PSA-1 cells (10 μg of total RNA) from either the undifferentiated state or stages 1, 2, and 3 of differentiation (PSA-1 cells undergo three stages of cellular differentiation corresponding to mouse embryonic cells of the following gestational ages, in days: 4.5–6.5 [PSA-1 stage 1]; 6.5–8.5 [PSA-1 stage 2]; 8.5–10.5 [PSA-1 stage 3]). A comparison of the protection of whole embryonic and placental total RNAs (20 μg each) showed that cyr61 is expressed in embryonic tissues at times that are coincident with the processes of cell differentiation and proliferation.

Expression characteristics of human cyr61 were determined by Northern analyses, using techniques that are standard in the art. Sambrook et al. RNA was isolated from the human diploid fibroblastic cell line WI38 (ATCC CCL-75). In addition, RNA was isolated from rat cells (REF52), hamster cells (CHO), and monkey cells (BSC40). Each of the cell lines was grown to confluence in MEM-10 (Eagle's Minimal Essential Medium with Earle's salts [GIBCO-BRL, Inc.], 2 mM glutamine, and 10% fetal calf serum [fcs]) and maintained in MEM-0.5 (a 0.5% serum medium) for two days. Cultures were then stimulated with 20% fcs, in the presence or absence of cycloheximide, by techniques known in the art. Lau et al. (1985: 1987). Ten microgram aliquots of RNA isolated from these cell lines were then fractionated by formaldehyde-agarose gel electrophoresis, transferred and immobilized on nitrocellulose filters, and exposed to a full-length [$^{32}$P]-radiolabeled murine cyr61 cDNA probe under hybridization conditions of high stringency. Human cyr61 RNA expression was similar to murine cyr61 expression. Both mouse and human cyr61 expression yielded approximately 2 kilobase RNAs. Additionally, both mouse and human expression of Cyr61 were stimulated by serum and were resistant to cycloheximide.

The distribution of human cyr61 mRNA was also examined using multiple tissue Northern blots (Clontech). The blots were hybridized in an ExpressHyb Solution (Clontech) according to the manufacturer's instructions. The results showed that cyr61 mRNA is abundant in the human heart, lung, pancreas, and placenta; is present at low levels in skeletal muscle, kidney and brain; and is not detectable in liver. These results are consistent with the expression of cyr61 in mouse tissues.

In addition, total cellular RNA was isolated from human skin fibroblasts (HSFS) that were either quiescent, growing exponentially, stimulated by serum, or exposed to cycloheximide. HUVE cells (ATCC CRL 1730) were maintained in Ham's F12 medium supplemented with 10% fbs (Intergene), 100 μg/ml heparin (Gibco BRL) and 30 μg/ml endothelial cell growth supplement (Collaborative Biomedical Products). Human skin fibroblasts (HSF, ATCC CRL-1475) and WI38 fibroblasts (ATCC CCL-75) were grown in Dulbecco's Modified Eagle's Medium (DMEM) supplemented with 10% fbs. Quiescent HSFs were prepared by growth in DMEM supplemented with 10% fbs to confluence followed by changing the medium to DMEM containing 0.1% fbs, for 2 days. Serum stimulation was carried out by changing the medium to 20% fbs for 1 hour. Where indicated. cycloheximide was added to 10 μg/ml simultaneously with serum for 3 hours.

RNAs from the aforementioned cells were isolated using a guanidinium isothiocyanate protocol. Chonzcynski et al., Anal. Biochem. 162:156–159 (1987). RNA samples were analyzed by electrophoretic separation in formaldehyde-agarose gels followed by transfer to nylon filters. Blots were hybridized with random-primed probes generated using either cyr61 or GAPDH as a template. Adams et al., Nature 355:632–634 (1992). The results indicated that human cyr61 mRNA is not detectably present in quiescent human skin fibroblasts, is abundant in logarithmically growing and serum stimulated HSFs, and is superinduced by cycloheximide.

The analysis of RNA encoding CTGF also involved techniques that are standard in the art. In particular, investigation of RNA encoding CTGF involved the isolation of total cellular RNA and Northern analyses, performed as described in U.S. Pat. No. 5,408,040, column 11, line 59. to column 12. line 14. and column 13. lines 10–29, incorporated herein by reference. A 2.4 kb RNA was identified. The expression of CTGF was high in the placenta, lung, heart, kidney, skeletal muscle and pancreas. However, CTGF expression was low in the liver and brain.

EXAMPLE 4

Transgenic Animals

The construction of transgenic mice bearing integrated copies of recombinant cyr61 sequences was accomplished using linear DNA fragments containing a fusion gene. The cyr61 coding sequence was independently fused to the β-actin, K14, and pgk promoters, described above. Expression of cyr61 was driven by these promoters in the transgenic animals. The fusion gene was produced by appropriate restriction endonuclease digestions, using standard techniques. The fusion gene fragments were injected into single-cell zygotes of Swiss Webster mice. The injected zygotes were then implanted into pseudopregnant females. Several litters of mice were produced in this manner. Newborns exhibiting unusual phenotypes were subjected to additional analyses. For example, neonatal transgenic mice expressing cyr61 under the pgk promoter exhibited skeletal deformities. including curly tails, immobile joints, and twisted limbs, resulting in locomotive difficulties. These mice typically were runted and died within seven days of birth. Transgenic mice expressing cyr61 under the β-actin promoter showed no obvious phenotype except that the mice were smaller. When mice bearing the transgene were back-crossed to the in-bred strain C57 BL/6, the progeny mice became progressively more runted with continued back-crossing. After three to four such back-crosses, essentially no progeny survive to reproduce. Transgenic mice expressing cyr61 under the K14 promoter exhibited a form of fibrotic dermatitis. The pathology involved excessive surface scratching, sometimes resulting in bleeding. Transgenic organisms having knock-out mutations of cyr61 can also be created using these standard techniques. Hogan et al., Manipulating the Mouse Embryo: A Laboratory Manual (Cold Spring Harbor Laboratory Press 1994), and are useful as models of disease states.

EXAMPLE 5

Cyr61 Expression

Native Cyr61 is expressed in embryonic tissues and is induced in a variety of wounded tissues. See below see also, O'Brien et al. (1992). The tissue distribution of Cyr61 was examined with rabbit anti-Cyr61 polyclonal antibodies elicited using a conventional immunological technique (Harlow et al., 1987) and affinity-purified. Using affinity-purified anti-Cyr61 polyclonal antibodies according to the invention, cyr61 expression was found in a variety of tissues, including smooth muscle, cardiomyocytes, and endothelia of the cardiovascular system; brain, spinal cord, ganglia and neurons, and retina of the nervous system; cartilage and bone of the skeletal system: epidermis, hair, oral epithelia, and cornea of the skin; bronchioles and blood vessels of the lung: and placental tissues. In addition to expression studies directed towards native cyr61 (mRNA and protein), studies using cyr61 transgenes, as described above, have contributed to our understanding of Cyr61 expression. The use of transgene fusions comprising the expression control sequences of cyr61 and the coding sequence of lacZ (encoding β-galactosidase) has provided a convenient colorimetric assay for protein expression.

The colorimetric assay involves the use of 5-Bromo-4-Chloro-3-Indolyl-β-D-Galactopyranoside (i.e., X-Gal) as a substrate for β-galactosidase, the gene product of lacZ. Enzymatic cleavage of X-Gal by β-galactosidase produces an intensely colored indigo dye useful in histochemical staining. In practice, embryonic and adult tissues subjected to analysis were dissected and fixed in 2% formaldehyde. 0.2% glutaraldehyde, 0.02% Nonidet P-40, and 0.01 sodium deoxycholate, in standard phosphate-buffered saline (PBS). Fixation times varied from 15–120 minutes, depending on the size and density of organ or embryo samples being subjected to analysis. Subsequently, samples were rinsed in PBS and stained overnight at 37° C. in a PBS solution containing 5 mM potassium ferrocyanide, 5 mM potassium ferricyanide, 2 mM $MgCl_2$, 0.02% Nonidet P-40, 0.01% sodium deoxycholate and 1 mg/ml of X-Gal (40 mg/ml in dimethylsulfoxide [DMSO]). Samples were then rinsed in PBS, post-fixed in 4% paraformaldehyde for 1–2 hours. and stored in 70% ethanol at 4° C. until subjected to microscopic examination. Mice containing the cyr61-lacZ transgene were used to map the expression profile of cyr61. The results are presented in Table I for embryonic tissues at day 12.5.

TABLE I

| Transgenic Mouse Line | Blood Vessels | Skeleton | Nervous System | Epidermis |
| --- | --- | --- | --- | --- |
| 1.S[1] | +[2] | − | + | + |
| 2.S | + | + | + | + |
| 3.S | + | +/− | + | + |
| 4.T | + | − | − | NA |
| 5.T | + | − | − | NA |
| 6.T | + | +/− | − | NA |
| 7.T | + | +/− | − | NA |
| 8.T | + | +/− | + | NA |

[1] Transgenic lines, S-stable (established) transgenic lines; T-transient lines
[2] +/− Expression pattern only partially reproduced.

The results indicate that Cyr61 is expressed in a variety of embryonic cell types. Additional information has been gleaned from the ectopic expression of Cyr61 resulting from another type of transgene fusion comprising a heterologous expression control sequence coupled to the coding sequence of cyr61. The control sequences, the K14 keratin promoter, the β-actin promoter, and the phosphoglycerokinase promoter, directed the expression of Cyr61 in a pattern that differed from its native expression.

Transgenic mice ectopically expressing Cyr61 were routinely smaller than wild type mice and exhibited a reduction in average life span. Moreover, these transgenic mice had abnormal hearts (i.e., thickened chamber walls with a corresponding reduction in internal capacity) and abnormal skeletons characterized by curved spines, joints swollen to the point of immobility, and curly tails. Therefore, ectopic expression of Cyr61 interferes with angiogenesis (blood vessel development and heart development) and chondrogenesis (skeletal development). In addition, transgenic mice carrying knockout mutations of cyr61 may be developed and tested as models of disease states associated with a lack of Cyr61 activity.

A strategy for the expression of recombinant cyr61 was designed using a Baculovirus expression vector in Sf9 cells. Expression systems involving Baculovirus expression vectors and Sf9 cells are described in *Current Protocols in Molecular Biology* §§ 16.9.1–16.12.6 (Ausubel et al., eds., 1987). One embodiment of the present invention implemented the expression strategy by cloning the murine cyr61 cDNA into pBlueBac2 a transfer vector. The recombinant clone, along with target AcMNPV (i.e., *Autographa californica* nuclear polyhedrosis virus, or Baculovirus) DNA, were delivered into Sf9 cells by liposome-mediated transfection, using the MaxBac Kit (Invitrogen, Inc., San Diego, Calif.) according to the manufacturer's instructions. Recombinant virus was plaque-purified and amplified by 3 passages through Sf9 cells via infection.

Conditioned medium of Sf9 insect cells infected with a baculovirus construct driving the synthesis of murine Cyr61 was used as a source for purification of Cyr61 (see below). The purified recombinant Cyr61 retains certain characteristics of the endogenous protein, e.g., the heparin-binding activity of Cyr61 (described below) from 3T3 fibroblast cells and had a structure similar to the endogenous protein as revealed by independent peptide profiles produced by partial proteolysis using either chymotrypsin or trypsin (sequencing grade: Boehringer-Mannheim, Inc., Indianapolis, Ind.).

Human cyr61 was also expressed using the baculovirus system. A SmaI-HindIII fragment (corresponding to nucleotides 100–1649 of SEQ ID NO: 3) of cyr61 cDNA spanning the entire human cyr61 open reading frame was subcloned into a pBlueBac3 baculovirus expression vector (Invitrogen). Recombinant baculovirus clones were obtained, plaque purified and amplified through three passages of Sf9 infection, using conventional techniques. Infection of Sf9 cells and human Cyr61 (hCyr61) purification was performed using standard techniques, with some modifications. Sf9 cells were maintained in serum-free Sf900-II medium (Sigma). Sf9 cells were seeded, at $2–3 \times 10^6$ cells per 150 mm dish, in monolayer cultures and were infected with 5 plaque forming units (PFU) of recombinant virus per cell. The conditioned medium was collected at 8 and 96 hours post-infection, cleared by centrifugation (5000×g. 5 minutes) and adjusted to 50 mM MES [2-(N-Morpholino)ethanesulfonic acid], pH 6.0, 1 mM PMSF (phenylmethylsulfonyl fluoride), and 1 mM EDTA. The medium was mixed with Sepharose S beads equilibrated with loading buffer (50 mM MES, pH 6.0, 1 mM PMSF, 1 mM EDTA. 150 mM NaCl) at a ratio of 5 ml Sepharose S beads per 500 ml of conditioned medium and the proteins were allowed to bind to the Sepharose S at 4° C. (o/n) with gentle stirring. Sepharose S beads were collected by sedimentation without stirring for 20 minutes and applied to the column. The column was washed with 6 volumes of 0.3 M NaCl in loading buffer and recombinant human Cyr61 was eluted from the column with a step gradient of NaCl (0.4–0.8 M) in loading buffer. This procedure resulted in 3–4 milligrams of purified Cyr61 protein from 500 ml of conditioned medium, and the purified Cyr61 was over 90% pure as judged by Coomassie Blue staining of SDS-gels.

In another embodiment, the complete human cyr61 cDNA is cloned into a cytomegalovirus vector such as pBK-CMV (Stratagene, La Jolla, Calif.) using the Polymerase Chain Reaction (Hayashi, in PCR: The Polymerase Chain Reaction 3–13 [Mullis et al. eds., Birkhauser 1994]) and Taq Polymerase with editing function, followed by conventional cloning techniques to insert the PCR fragment into a vector. The expression vector is then introduced into HUVE cells by liposome-mediated transfection. Recipient clones containing the vector-borne neo gene are selected using G418. Selected clones are expanded and Cyr61 expression is identified by Reverse Transcription-Polymerase Chain Reaction (i.e., RT-PCR; Chelly et al, in PCR: The Polymerase Chain Reaction 97–109 [Mullis et al. eds., Birkhauser 1994]) or Enzyme-Linked Immunosorbent Assays (i.e., ELISA; Stites et al., in Basic and Clinical Immunology 243 [Stites et al. eds., Appleton & Lange 1991]) assays.

In other embodiments of the invention, Cyr61 protein is expressed in bacterial cells or other expression systems (e.g., yeast) using, the cyr61 cDNA coding region linked to promoters that are operative in the cell type being used. Using one of these approaches, Cyr61 protein may be obtained in a form that can be administered directly to patients, e.g., by intravenous routes, to treat angiogenic, chondrogenic, or oncogenic disorders. One of skill in the art would recognize that other administration routes are also available. e.g., topical or local application, liposome-mediated delivery techniques, or subcutaneous, intradermal, intraperitoneal, or intramuscular injection.

EXAMPLE 6

Fisp12 Expression

The expression of Fisp12, and a comparison of the expression characteristics of Cyr61 and Fisp12, were investigated using immunohistochemical techniques. For these immunohistochemical analyses. tissue samples (see below) were initially subjected to methyl-Carnoy's fixative (60% methanol. 30% chloroform and 10% glacial acetic acid) for 2–4 hours. They were then dehydrated, cleared and infiltrated in Paraplast X-tra wax at 55–56 C for minimal duration. 7 µm thick sections were collected on poly-L-lysine-coated slides (Sigma), mounted and dewaxed. They were then treated with 0.03% solution of $H_2O_2$ in methanol for 30 min. to inactivate endogenous peroxidase activity. After rehydration, sections were put in Tris-buffered saline (TBS: 10 mM Tris. pH 7.6 and 140 mM NaCl) for 15 minutes. At that point, sections were blotted to remove excess TBS with paper towels and blocked with 3% normal goat serum in TBS for 10 minutes in a humid chamber. Excess buffer was then drained and primary antibodies applied. Affinity purified anti-Cyr61 antibodies were diluted 1:50 in 3% normal goat serum-TBS solution. Dilution for affinity-purified anti-Fisp12 antibody was 1:25. Routine control was 3% normal goat serum-TBS, or irrelevant antibody (for example, monoclonal anti-smooth muscle cell α-actin). Specificity of staining was confirmed by incubation of anti-Cyr61 or anti-Fisp12 antibodies with an excess of the corresponding antigen on ice for at least two hours prior to applying to sections. Complete competition was observed. By contrast, cross-competition (incubation of anti-Cyr61 antibodies with Fisp12 antigen and vice versa) did not occur.

Primary antibodies were left on sections overnight at 4 C. They were then washed with TBS twice, and subjected to 30 minutes incubation with secondary antibodies at room temperature. Secondary antibodies used were goat anti-rabbit horseradish peroxidase conjugates from Boehringer-Mannheim, Inc., Indianapolis, Ind. (used at 1:400 dilution). Sections were washed twice in TBS and chromogenic horseradish peroxidase substrate was applied for 5 minutes (1 mg/ml of diaminobenzidine in 50 mM Tris-HCl. pH 7.2 and 0.03% $H_2O_2$). Sections were then counterstained in Ehrlich's haematoxylin or in Alcian blue, dehydrated and mounted in Permount.

Mouse embryos between the neural fold (E8.5) and late organogenesis (E18.5) stages of development were sectioned and subjected to immunostaining with antigen-affinity-purified rabbit anti-Cyr61 and anti-Fisp12 antibodies. As various organs developed during embryogenesis. the presence of Cyr61 and Fisp12 was determined. Cyr61 and Fisp12 were co-localized in a number of tissues and organs. A notable example is the placenta, where both proteins were readily detectable. In particular, both Cyr61 and Fisp12 were found in and around the trophoblastic giant cells. corroborating the previous detection of cyr61 mRNA in these cells by in situ hybridization (O'Brien and Lau, 1992). Both Cyr61 and Fisp12 signals in immunohistochemical staining were blocked by either the corresponding Cyr61 or Fisp 12 antigen but not by each other, nor by irrelevant proteins, demonstrating specificity. In general, Cyr61 and Fisp12 proteins could be detected both intracellularly and extracellularly.

In addition to the placenta, both Cyr61 and Fisp12 were detected in the cardiovascular system, including the smooth muscle, the cardiomyocytes, and the endothelia. Both proteins were also found in the bronchioles and the blood vessels in the lung. Low levels of anti-Cyr61 and anti-Fisp12 staining could be detected transiently in the skeletal muscle. This staining is associated with connective tissue sheets, rather than myocytes; in this instance the staining pattern was clearly extracellular.

A more complex pattern of distribution was found in the epidermis and the epithelia. Both Cyr61 and Fisp12 staining could be detected in the early, single-cell layer of embryonic epidermis, as well as in later, multilayered differentiating epidermis. Fisp12 in epidermis declined to an undetectable level by the end of gestation and remained as such through adulthood, whereas Cyr61 was readily detectable in the epidermis. In the neonate, a strong staining for Fisp12 was seen in the oral epithelia where Cyr61 staining was much weaker, while Cyr61 was found in the upper jawbone where Fisp12 was not observed. The anti-Fisp12 signal in the oral epithelia gradually increased and remained intense into adulthood. In the tongue, both Cyr61 and Fisp12 were seen in the keratinized epithelia, although the Fisp12 staining pattern, but not that of Cyr61, excludes the filiform papillae.

Aside from the aforementioned sites of localization, Cyr61 and Fisp12 were also uniquely localized in several organ systems. For example, Cyr61, but not Fisp12, was present in skeletal and nervous systems. As expected from in situ hybridization results (O'Brien and Lau, 1992), Cyr61 protein was readily detected in the sclerotomal masses of the somites, and in cartilage and bone at later stages of development. In contrast, Fisp12 was not detectable in the skeletal system. Since correlation with chondrocytic differentiation is one of the most striking features of cyr61 expression (O'Brien and Lau, 1992), the absence of Fisp12 in the skeletal system may underscore an important difference in the biological roles of Cyr61 and Fisp12. In the E14.5 embryo, Cyr61 could be detected in the ventral spinal cord, dorsal ganglia, axial muscle and sclerotome-derived cartilaginous vertebrae. Fisp12, however, was not detected in these tissues.

By contrast, Fisp12 was uniquely present in various secretory tissues. Beginning at E16.5. Fisp12 could be detected in the pancreas, kidneys, and salivary glands. In the pancreas, Fisp12 was strictly localized to the periphery of the islets of Langerhans. In the kidney, strong Fisp12 staining was seen in the collecting tubules and Henle's loops, regions where Cyr61 was not found. In the mucous-type submandibular salivary gland only collecting ducts stained for Fisp12, whereas in the mixed mucous-serous submandibular gland, both serous acini and collecting ducts stained. The signal in acini was peripheral, raising the possibility that Fisp12 is capsule-associated. In simple holocrine sebaceous glands a strong acellular Fisp 12 signal was detected.

In summary, Cyr61 and Fisp12 have been co-localized in the placenta, the cardiovascular system, the lung and the skin. Neither protein was detected in the digestive system or the endocrine glands. Unique localization of Cyr61 can be detected in the skeletal and central nervous system, and Fisp12 is found in secretory tissues where Cyr61 is not.

An issue closely related to protein expression concerns the metabolic fate of the expressed proteins. Members of the cysteine-rich protein family have been localized. As discussed above, secreted Cyr61 is found in the ECM and on the cell surface but not in the culture medium (Yang and Lau, 1991), yet secreted Fisp12 was readily detected in the culture medium (Ryseck et al., 1991). To address the question of whether Fisp12 is also ECM-associated, the fate of both Cyr61 and Fisp12 was followed using pulse-chase experiments. Serum-stimulated, sub-confluent NIH 3T3 fibroblasts were metabolically pulse-labeled for 1 hour and chased in cold medium for various times. Samples were fractionated into cellular, ECM, and medium fractions followed by immunoprecipitation to detect Cyr61 and Fisp12. Both proteins have a similar short half-life of approximately 30 minutes in the cellular fraction, which includes both newly synthesized intracellular proteins as well as secreted proteins associated with the cell surface (Yang and Lau, 1991). It should be noted that since Cyr61 is quantitatively secreted after synthesis and only a minor fraction is stably associated with the ECM, the bulk of secreted Cyr61 is cell-surface associated (Yang and Lau, 1991).

A fraction of Cyr61 was chased into the ECM where it remained stable for several hours. Newly synthesized Fisp12 was also chased into the ECM, where its half-life was only about 1 hour. A larger fraction of Fisp12 was chased to the conditioned medium, where no Cyr61 was detectable. Fisp12 in the conditioned medium also had a short half-life of about 2 hours. Thus, whereas Cyr61 is strongly associated with the ECM, Fisp12 is associated with the ECM more transiently. This result suggests that Fisp12 might be able to act at a site distant from its site of synthesis and secretion, whereas Cyr61 may act more locally.

Since many ECM proteins associate with the matrix via interaction with heparan sulfate proteoglycans, the affinity with which a protein binds heparin might be a factor in its interaction with the ECM. The results of heparin binding assays, described below, are consistent with this hypothesis.

EXAMPLE 7

Protein Purification

Serum-stimulated NIH 3T3 fibroblast cells were lysed to provide a source of native murine Cyr61. Yang et al. Similarly, human fibroblasts are a source of native human Cyr61.

Recombinant murine Cyr61 was purified from Sf9 cells harboring the recombinant Baculovirus vector, described above, containing the complete cyr61 coding sequence. Although murine Cyr61 in Sf9 cell lysates formed insoluble aggregates as was the case with bacterial cell extracts, approximately 10% of the Cyr61 synthesized was secreted into the medium in a soluble form. The soluble, secreted form of Cyr61 was therefore subjected to purification.

Initially, subconfluent Sf9 cells in monolayer cultures were generated in supplemented Grace's medium (GIBCO-BRL, Inc., Grand Island, N.Y.). Grace, *Nature* 195:788 (1962). The Sf9 cells were then infected with 10 plaque-forming-units/cell of the recombinant Baculovirus vector, incubated for 16 hours, and fed with serum-free Grace's medium. These cells were expanded in serum-free Grace's Medium. The conditioned medium was collected 48 hours post-infection, although Cyr61 expression could be detected in the medium 24 hours after infection. Subsequently, the conditioned medium was cleared by centrifugation at 5000×g for 5 minutes, chilled to 4° C., adjusted to 50 mM MES, pH 6.0, 2 mM EDTA (Ethylenediamine tetraacetic acid), 1 mM PMSF (Phenylmethylsulfonyl fluoride) and applied to a Sepharose S column (Sigma Chemical Co., St. Louis, Mo.) at 4° C. (5 ml void volume per 500 ml medium). The column was washed with a buffer (50 mM MES, pH 6.0, 2 mM EDTA, 0.5 mM PMSF) containing 150 NaCl. and bound proteins were eluted with a linear gradient of NaCl (0.2–1.0 M) in the same buffer. The pooled fractions of Cyr61 eluted at 0.6–0.7 M NaCl as a distinct broad peak. The column fractions were 90% pure, as determined by 10% SDS-PAGE followed by Coomassie Blue staining or Western analysis. using techniques that are standard in the art. Yang et al.; see also, Sambrook et al., supra. For Western analysis, blots were probed with affinity-purified anti-Cyr61 antibodies as described in Yang et al., supra. After antibody probing, Western blots were stained with ECL™ (i.e., Enhanced ChemiLuminescence) detection reagents (Amersham Corp., Arlington Heights. Ill.). Fractions containing Cyr61 were pooled, adjusted to pH 7.5 with Tris-HCl. pH 7.5, and glycerol was added to 10% prior to storage of the aliquots at −70° C. Protein concentration was determined by the modified Lowry method using the BioRad protein assay kit (BioRad Laboratories, Inc., Hercules. Calif.). This purification procedure was repeated at least five times with similar results. The typical yield was 3–4 mg of 90% pure Cyr61 protein from 500 ml of conditioned medium.

Fisp12 was purified using a modification of the Cyr61 purification scheme (Kireeva et al., *Experimental Cell Research,* in press). Serum-free conditioned media (500 ml) of Sf9 cells infected at 10 pfu per cell were collected 48 hours post-infection and loaded onto a 5-ml Sepharose S (Sigma Chemical Co., St. Louis, Mo.) column. After extensive washing at 0.2 M and 0.4 M NaCl, bound proteins were recovered by step elution with 50 mM MES (pH 6.0) containing 0.5 M NaCl. Fractions containing Fisp12 of greater than 80% purity were pooled, NaCl adjusted to 0.15 M and the protein was concentrated 3–5 fold on a 0.5 ml Sepharose S column with elution of the protein at 0.6 M NaCl.

This purification scheme allowed the isolation of 1.5 mg of recombinant Fisp12 protein of at least 80% purity from 500 ml of serum-free conditioned media.

CTGF was purified by affinity chromatography using anti-PDGF cross-reactivity between CTGF and PDGF, as described in U.S. Pat. No. 5.408.040. column 7, line 15, to column 9, line 63, incorporated herein by reference.

EXAMPLE 8

Polypeptide Characterization

The murine Cyr61 protein has a M of 41,000 and is 379 amino acids long including the N-terminal secretory signal. There is 91% amino acid sequence identity with the 381 amino acid sequence of the human protein. Those regions of the mouse and human proteins contributing to the similarity of the two proteins would be expected to participate in the biological activities shared by the two polypeptides and disclosed herein. However, the mouse and human proteins do diverge significantly in the central portion of the proteins, where each protein is devoid of cysteines. See, O'Brien et al., *Cell Growth & Diff* 3:645–654 (1992). A cysteine-free region in the murine Cyr61 amino acid sequence is found between amino acid residues 164 to 226 (SEQ ID NO: 2). A corresponding cysteine-free region is found in the human Cyr61 amino acid sequence between amino acid residues 163 to 229 (SEQ ID NO: 4). More particularly, the mouse and human Cyr61 proteins are most divergent between Cyr61 amino acids 170–185 and 210–225. Other members of the ECM signalling molecule family of cysteine-rich proteins, e.g., Fisp12 (SEQ ID NO: 6) and CTGF (SEQ ID NO: 8), exhibit similar structures suggestive of secreted proteins having sequences dominated by cysteine residues.

Because murine Cyr61 contains 38 cysteines in the 355 amino acid secreted portion, the contribution of disulfide bond formation to Cyr61 tertiary structure was investigated. Exposure of Cyr61 to 10 mM dithiothreitol (DTT) for 16 hours did not affect the ability of Cyr61 to mediate cell attachment (see below). However, Cyr61 was inactivated by heating at 75° C. for 5 minutes by incubation in 100 mM HCl, or upon extensive digestion with chymotrypsin. These results indicate that murine Cyr61 is a heat- and acid-labile protein whose active conformation is not sensitive to reducing agents. The aforementioned structural similarities of murine and human Cyr61 polypeptides suggests that human Cyr61 may also be sensitive to heat or acid, but insensitive to reducing agents. In addition, Cyr61 is neither phosphorylated nor glycosylated.

To determine if the purified recombinant murine Cyr61 described above was the same as native murine Cyr61, two additional characteristics of mouse Cyr61 were determined. First, two independent protein fingerprints of recombinant and native murine Cyr61 were obtained. Purified recombinant murine Cyr61 and a lysate of serum-stimulated 3T3 cells, known to contain native murine Cyr61, were subjected to limited proteolysis with either trypsin or chymotrypsin, and their digestion products were compared. Partial tryptic digests of both the recombinant protein and cell lysate resulted in two Cyr61 fragments of approximately 21 and 19 kDa. Similarly, fingerprinting of both preparations by partial chymotrypsin digestion produced stable 23 kDa fragments from recombinant murine Cyr61 and native murine Cyr61.

Another criterion used to assess the properties of recombinant Cyr61 was its ability to bind heparin, described below. Purified recombinant murine Cyr61 bound quantitatively to heparin-sepharose at 0.15 M NaCl and was eluted at 0.8–1.0 M NaCl. This heparin binding capacity is similar to native murine Cyr61 obtained from serum-stimulated mouse fibroblasts. Because of the similarities of the murine and human Cyr61 proteins, recombinant human Cyr61 should exhibit properties similar to the native human Cyr61, as was the case for the murine polypeptides.

The polypeptides of the invention also extend to fragments. analogs and derivatives of the aforementioned full-length ECM signalling-molecules such as human and mouse Cyr61. The invention contemplates peptide fragments of ECM signalling molecules that retain at least one biological activity of an ECM signalling molecule, as described above. Candidate fragments for retaining at least one biological activity of an ECM signalling molecule include fragments that have an amino acid sequence corresponding to a conserved region of the known ECM signalling molecules. For example, fragments retaining one or more of the conserved cysteine residues of ECM signalling molecules would be likely candidates for ECM signalling molecule fragments that retain at least one biological activity. Beyond the naturally occurring amino acid sequences of ECM signalling molecule fragments, the polypeptides of the invention include analogs of the amino acid sequences or subsequences of native ECM signalling molecules.

ECM signalling molecule analogs are polypeptides that differ in amino acid sequence from native ECM signalling molecules but retain at least one biological activity of a native ECM signalling molecule, as described above. These analogs may differ in amino acid sequence from native ECM signalling molecules, e.g., by the insertion, deletion, or conservative substitution of amino acids. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art, Kyte et al., *J. Mol. Biol.* 157:105–132 (1982). The hydropathic index of an amino acid is based on a consideration of its hydrophobicity and charge, and include the following values: alanine (+1.8), arginine (−4.5), asparagine (−3.5), aspartate (−3.5), cysteine/cystine (+2.5), glycine (−0.4), glutamate (−3.5), glutamine (−3.5), histidine (−3.2), isoleucine (+4.5), leucine (+3.8), lysine (−3.9), methionine (+1.9), phenylalanine (+2.8), proline (−1.6), serine (−0.8), threonine (−0.7), tryptophan (−0.9), tyrosine (−1.3), and valine (+4.2). It is known in the art that amino acids of similar hydropathic indexes can be substituted and still retain protein function. Preferably, amino acids having hydropathic indexes of ±2 are substituted.

The hydrophilicity of amino acids can also be used to reveal substitutions that would result in proteins retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity. U.S. Pat. No. 4,554,101. incorporated herein by reference. Hydrophilicity values for each of the common amino acids, as reported in U.S. Pat. No. 4,554,101, are: alanine (−0.5), arginine (+3.0), asparagine (+0.2), aspartate (+3.0±1), cysteine (−1.0), glycine (0), glutamate (+3.0±1), glutamine (+0.2), histidine (−0.5), isoleucine (−1.8), leucine (−1.8), lysine (+3.0), methionine (−1.3), phenylalanine (−2.5), proline (−0.5±1), serine (+0.3), threonine (−0.4), tryptophan (−3.4), tyrosine (−2.3), and valine (−1.5). Substitution of amino acids having similar hydrophilicity values can result in proteins retaining biological activity, for example immunogenicity, as is understood in the art. Preferably, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Additionally, computerized algorithms are available to assist in predicting amino acid sequence domains likely to be accessible to an aqueous solvent. These domains are known in the art to frequently be disposed towards the exterior of a protein, thereby potentially contributing to binding determinants, including antigenic determinants. Having the DNA sequence in hand, the preparation of such analogs is accomplished by methods well known in the art (e.g., site-directed) mutagenesis and other techniques.

Derivatives of ECM signalling molecules are also contemplated by the invention. ECM signalling molecule derivatives are proteins or peptides that differ from native ECM signalling molecules in ways other than primary structure (i.e., amino acid sequence). By way of illustration, ECM signalling molecule derivatives may differ from native ECM signalling molecules by being glycosylated, one form of post-translational modification. For example, polypeptides may exhibit glycosylation patterns due to expression in heterologous systems. If these polypeptides retain at least one biological activity of a native ECM signalling molecule, then these polypeptides are ECM signalling molecule derivatives according to the invention. Other ECM signalling molecule derivatives include, but are not limited to, fusion proteins having a covalently modified N- or C-terminus, PEGylated polypeptides, polypeptides associated with lipid moieties, alkylated polypeptides, polypeptides linked via an amino acid side-chain functional group to other polypeptides or chemicals and additional modifications as would be understood in the art. In addition,the invention contemplates ECM signalling molecule-related polypeptides that bind to an ECM signalling molecule receptor, as described below.

The various polypeptides of the present invention, as described above may be provided as discrete polypeptides or be linked, e.g., by covalent bonds, to other compounds. For example, immunogenic carriers such as Keyhole Limpet Hemocyanin may be bound to a ECM signalling molecule of the invention.

EXAMPLE 9

Heparin Binding Assay

The heparin binding assay for native murine Cyr61. described in Yang et al., was modified for the purified recombinant murine protein. Initially, recombinant purified Cyr61 was suspended in RIPA (Radioimmuno-precipitation assay) buffer (150 mM NaCl, 1.0% NP-40, 0.5% deoxycholate. 0.1% SDS, 50 mM Tris-HCl, pH 8.0, 1 mM phenylmethylsulfonyl fluoride). Next. 200 µl of a 50% (v/v) slurry of heparin-Sepharose CL 6 B beads (Pharmacia-LKB Biotechnology, Inc., Piscataway, N.J.) was added to 100 µl of the recombinant Cyr61 solution and incubated for 1 hour. Under these conditions, human Cyr61 was quantitatively bound to heparin-agarose. Application of a salt concentration gradient in RIPA buffer resulted in the elution of recombinant murine Cyr61 at 0.8–1.0 M NaCl. The elution profile of the recombinant protein was similar to the elution profile for native murine Cyr61.

One might expect that Fisp12 would bind heparin with lower affinity than Cyr61, as it does not interact with the ECM as strongly as Cyr61. To examine this possibility, metabolically labeled [$^{35}$S-cysteine; 100 µCi per 100 mm dish: ICN] cell lysates were incubated with heparin agarose beads which were subsequently washed to remove unbound proteins. Bound proteins were eluted in increasing salt concentrations. Fisp12 from cell lysates was retained on heparin agarose but was eluted by 0.2 to 0.6 M NaCl with peak elution at 0.4 M NaCl. This is in contrast to Cyr61, which was eluted at significantly higher concentrations of NaCl. This difference in heparin binding is consistent with the differing affinities of Cyr61 and Fisp12 for the ECM, suggesting that binding to heparan sulfate proteoglycans may be a primary mechanism by which both proteins associate with the ECM.

EXAMPLE 10

Receptors

Human Cyr61, like murine Cyr61, was localized to the cell surface and ECM. The localization of Cyr61 to the cell surface implicated a cell surface receptor binding Cyr61. Consistent with that implication, the biological effects of Cyr61 are mediated by the $\alpha_v\beta_3$ integrin, or vitronectin receptor. The $\alpha_v\beta_3$ integrin, in association with other integrins, forms protein clusters providing focal points for cytoskeletal attachment. Cyr61 induces the formation of protein clusters, including the protein clusters containing the $\alpha_v\beta_3$ integrin. In addition, using an in vitro assay, the biological effects of Cyr61, including Cyr61-induced cell adhesion and mitogenesis, were abolished by the addition of either one of two monoclonal antibodies—LM609 (Cheresh, *Proc. Natl. Acad. Sci. [USA]* 84:6471–6475 [1987]) or anti-VnR 1 (Chen et al., *Blood* 86:2606–2615 [1995])—directed to the $\alpha_v\beta_3$ integrin. This data led to the identification of the $\alpha_v\beta_3$ integrin as the Cyr61 receptor.

Cyr61 induction of HUVE cell adhesion, described in Example 13 below, led to an investigation of the divalent cation-sensitive cell surface receptors expressed by HUVE cells. The cell adhesion properties of Cyr61 were used to identify the receptor, which is a divalent cation-sensitive cell surface receptor. The ability of Cyr61 to mediate cell adhesion, coupled with the strict requirement for divalent cations in the process, indicated that Cyr61 interacts with one of the divalent cation-dependent cell adhesion molecules from the integrin, selectin, or cadherin families, Ruoslahti et al., *Exp. Cell Res.* 227:1–11 (1996). Using well-characterized approaches to receptor identification, a series of inhibition studies were conducted. Inhibitors, or blocking agents, of various degrees of specificity (EDTA, similar to the EGTA described above; inhibitory peptides bearing variants of the RGD (single letter amino acid code) integrin recognition motif, such as RGDS, SGDR, and RGDSPK (Ruoslahti, et al., *Science* 238:491–497 [1987], Ruoslahti, E., *Ann. Rev. of Cell and Dev. Biol.* 12:698–715 [1996]); and known, specific anti-receptor antibodies) were used to identify a Cyr61 receptor. That receptor was the $\alpha_v\beta_3$ integrin, also known to function as the vitronectin receptor. Confirmation of that identification was obtained by showing that antibody LM609, a specific anti-$\alpha_v\beta_3$ integrin antibody, could block the effect of Cyr61 on cell adhesion. Integrins form a large family of heterodimeric adhesion receptors, with a broad ligand specificity range, involved in cell-cell and cell-matrix interactions. Beyond their requirement for divalent cations and their involvement in cell-matrix adhesion events [Hynes, R. O., *Cell* 69:11–25 (1992)], integrins also are involved in cell migration [Damsky et al., *Curr. Opin. Cell Biol.* 4:772–781 (1992): Doerr et al., *J. Biol. Chem.* 271: 2443–447 (1996)] and proliferation [Juliano et al., *J. Cell Biol.*, 120:577–585 (1993); Plopper et al., *Mol. Biol. Cell* 6:1349–1365 (1995); and Clark et al., *Science* 268:233–239 (1995)], two additional processes associated with Cyr61 activity. The $\alpha_v\beta_3$ integrin was found to be essential for Cyr61-mediated cell adhesion.

Characterization of CTGF binding to cells has been reported to occur through a cell surface receptor that also interacts with PDGF-BB (the BB isoform of PDGF), as recited in U.S. Pat. No. 5,408,040, column 11, line 10. to column 12, line 14, incorporated herein by reference. The identification of the foregoing receptors permits the the design and production of molecules and which bind to the respective receptors to inhibit the activities of ECM molecules.

EXAMPLE 11

Anti-ECM Signalling Molecule Antibodies

Antibodies, optionally attached to a label or to a toxin as described below, are also contemplated by the present invention. The availability of the human cyr61 cDNA sequence and the Cyr61 deduced protein sequence facilitate the implementation of methods designed to elicit anti-Cyr61 antibodies using a number of techniques that are standard in the art. Harlow et al.

In one embodiment, polyclonal antibodies directed against Cyr61 are generated. The generation of anti-Cyr61 antibodies specific for human Cyr61, for example, is optimized by designing appropriate antigens. The human Cyr61 protein is 381 amino acids long, including the N-terminal secretory signal. As described above, human Cyr61 exhibits a 91% amino acid sequence identity with the 379 amino acid sequence of the mouse protein. However, the mouse and human proteins diverge most significantly in the central portion of the proteins, where they are devoid of cysteines (see above). These sequence differences are exploited to elicit antibodies specific to the human Cyr61 by using as an antigen a peptide having a sequence derived from one of the divergent regions in the human protein, although antibodies directed to a conserved region are also contemplated by the invention.

In another embodiment of the present invention, monoclonal antibodies are elicited using intact recombinant human Cyr61 although a fragment may be used. Female BALB/c mice are inoculated intraperitoneally with a mixture of 0.25 ml recombinant human Cyr61 (5–50 micrograms), bacterially produced or produced in eukaryotic cells, and 0.25 ml complete Freund's adjuvant. Fourteen days later the injections are repeated with the substitution of incomplete Freund's adjuvant for complete Freund's adjuvant. After an additional two weeks, another injection of human Cyr61 in incomplete Freund's adjuvant is administered. About two weeks after the third injection, tail bleeds are performed and serum samples are screened for human anti-Cyr61 antibodies by immunoprecipitation with radiolabeled recombinant human Cyr61. About two months after the initial injection, mice whose sera yield the highest antibody titers are given booster injections of Cyr61 (5–50 micrograms in incomplete Freund's adjuvant, 0.1 ml intravenously and 0.1 ml intraperitoneally). Three days after the booster injection, the mice are sacrificed. Splenocytes are then isolated from each mouse using standard techniques, and the cells are washed and individually fused with a myeloma cell line, e.g., the X63Ag8.653 cell line (Harlow et al.), using polyethylene glycol, by techniques that are known in the art. Other suitable cell lines for fusion with splenocytes are described in Harlow et al., at page 144, Table 6.2, incorporated herein by reference. Fused cells are removed from the PEG solution, diluted into a counter-selective medium (e.g., Hypoxanthine-Aminopterin-Thymidine or HAT medium) to kill unfused myeloma cells, and inoculated into multi-well tissue culture dishes.

About 1–2 weeks later, samples of the tissue culture supernatants are removed from wells containing growing hybridomas, and tested for the presence of anti-Cyr61 antibodies by binding to recombinant human Cyr61 bound to nitrocellulose and screening with labeled anti-immunoglobulin antibody in a standard antibody-capture assay. Cells from positive wells are grown and single cells are cloned on feeder layers of splenocytes. The cloned cell lines are stored frozen. Monoclonal antibodies are collected and purified using standard techniques, e.g., hydroxylapatite chromatography. In an alternative, Cyr61 peptides used as antigens, may be attached to immunogenic carriers such as keyhole limpet hemocyanin carrier protein, to elicit monoclonal anti-Cyr61 antibodies.

Another embodiment involves the generation of antibody products against a fusion protein containing part, or all, of human Cyr61, including enough of the protein sequence to exhibit a useful epitope in a fusion protein. The fusion of the large subunit of anthranilate synthase (i.e., TrpE) murine Cyr61, and the fusion of glutathione S-transferase (i.e., GST) to murine Cyr61, have been used to successfully raise antibodies against murine Cyr61. Yang et al. In addition, a wide variety of polypeptides, well known to those of skill in the art, may be used in the formation of Cyr61 fusion polypeptides according to the invention.

More particularly, Yang reported a TrpE-Cyr61 fusion polypeptide that was expressed from a recombinant clone constructed by cloning a fragment of the murine cyr61 cDNA containing nucleotide 456 through nucleotide 951 (encoding Cyr61 amino acids 93–379) into the SacI site of the pATH1 vector, Dieckman et al., *J. Biol. Chem.* 260: 1513–1520 (1985). The recombinant construct was transformed into a bacterial host. e.g., *E. coli* K12, and expression of the fusion protein was induced by addition of 25 µg/ml indoleacrylic acid to growing cultures. Subsequently, cells were lysed and total cell lysate was fractionated by electrophoresis on a 7.5% polyacrylamide gel. The fusion protein of predicted size was the only band induced by indoleacrylic acid; that band was eluted from the gel and used as an antigen to immunize New Zealand White rabbits (Langshaw Farms) using techniques that are standard in the art. Harlow et al. In addition to polyclonal antibodies, the invention comprehends monoclonal antibodies directed to such fusion proteins.

In other embodiments of the invention, recombinant antibody products are used. For example, chimeric antibody products, "humanized" antibody products, and CDR-grafted antibody products are within the scope of the invention, Kashmiri et al., *Hybridoma* 14:461–473 (1995), incorporated herein by reference. Also contemplated by the invention are antibody fragments. The antibody products include the aforementioned types of antibody products used as isolated antibodies or as antibodies attached to labels. Labels can be signal-generating enzymes, antigens, other antibodies, lectins, carbohydrates, biotin, avidin, radioisotopes, toxins, heavy metals, and other compositions known in the art, attachment techniques are also well known in the art.

Anti-Cyr61 antibodies are useful in diagnosing the risk of thrombosis, as explained more fully in Example 20 below. In addition, anti-Cyr61 antibodies are used in therapies designed to prevent or relieve undesirable clotting attributable to abnormal levels of Cyr61. Further, antibodies according to the invention can be attached to toxins such as ricin using techniques well known in the art. These antibody products according to the invention are useful in delivering specifically-targeted cytotoxins to cells expressing Cyr61, e.g., cells participating in the neovascularization of solid tumors. These antibodies are delivered by a variety of administrative routes, in pharmaceutical compositions comprising carriers or diluents, as would be understood by one of skill in the art.

Antibodies specifically recognizing Fisp12 have also been elicited using a fusion protein. The antigen used to raise anti-Fisp12 antibodies linked glutathione-S-transferase (GST) to the central portion of Fisp12 (GST-Fisp12), where there is no sequence similarity to Cyr61 (O'Brien and Lau, 1992). A construct containing cDNA encoding amino acids 165 to 200 of Fisp12 was fused to the glutathione-S-transferase (GST) coding sequence. This was done by using polymerase chain reaction (PCR) to direct synthesis of a fragment of DNA encompassing that fragment of fisp12 flanked by a 5' BamHI restriction site and a 3' EcoRI restriction site. The 5' primer has the sequence 5'-GGG-GATCTGTGACGAGCCCAAGGAC-3' (SEQ ID NO: 9) and the 3' primer has the sequence 5'-GGGAATTCGAC-CAGGCAGTTGGCTCG-3' (SEQ ID NO: 10). For Cyr61-specific antiserum, a construct fusing the central portion of Cyr61 (amino acids 163 to 229), which contains no sequence similarity to Fisp12, to GST was made in the same manner using the 5' primer 5'-GGGGATCCTGTGATGAAGACAG-CATT-3' (SEQ ID NO: 11) and the 3' primer5'-GGGAAT-TCAACGATGCATTTCTGGCC-3' (SEQ ID NO: 12). These were directionally cloned into pGEX2 T vector (Pharmacia-LKB, Inc.) and the clones confirmed by sequence analysis. The GST-fusion protein was isolated on glutathione sepharose 4 B (Pharmacia-LKB, Inc.) according to manufacturer's instructions, and used to immunize New Zealand white rabbits. For affinity purifications, antisera were first passed through a GST-protein affinity column to remove antibodies raised against GST, then through a GST-Fisp12 or GST-Cyr61 protein affinity column to isolate anti-Fisp12 or anti-Cyr61 antibodies (Harlow et al., 1988).

These antibodies immunoprecipitated the correct size Fisp12 protein product synthesized in vitro directed by fisp12 mRNA. The antibodies are specific for the Fisp12 polypeptide and show no cross-reactivity with Cyr61.

Polyclonal antibodies recognizing CTGF are also known. U.S. Pat. No. 5.408,040, column 7, line 41, to column 9, line 63, incorporated by reference hereinabove, reveals an immunological cross-reactivity between PDGF and CTGF as described above.

EXAMPLE 12

Inhibitory peptides

Another embodiment of the present invention involves the use of inhibitory peptides in therapeutic strategies designed to inhibit the activity of the Cyr61 protein. One approach is to synthesize an inhibitory peptide based on the protein sequence of Cyr61. For example, a peptide comprising an amino acid sequence that is conserved between murine Cyr61 (SEQ ID NO: 2) and human Cyr61 (SEQ ID NO: 4) competes with native Cyr61 for its binding sites. This competition thereby inhibits the action of native Cyr61. For example, administration of an inhibitory peptide by well-known routes inhibits the capacity of Cyr61 to influence the cascade of events resulting in blood clots, the vascularization of tumors, or the abnormal vascularization of the eye (e.g., eye disorders characterized by vascularization of the retina or the vitreous humor), etc. In particular, an inhibitory peptide prevents Cyr61 from inhibiting the action of Tissue Factor Pathway Inhibitor, or TFPI, as described below.

In an embodiment of the invention, inhibitory peptides were designed to compete with Cyr61. These inhibitory peptides, like the antibodies of the preceding Example, exemplify modulators of Cyr61 activity, as described in the context of a variety of assays for Cyr61 activity that are disclosed herein. The peptide design was guided by sequence comparisons among murine Cyr61, Fisp12, and Nov (an avian proto-oncogene). The amino acid sequences of several members of this family are compared in FIG. 1. These types of sequence comparisons provide a basis for a rational design for a variety of inhibitory peptides. Some of these designed peptides, for example peptides spanning amino acids 48–68 (SEQ ID NO: 13). 115–135 (SEQ ID NO: 14), 227–250 (SEQ ID NO: 15), 245–270 (SEQ ID NO: 16), and 310–330 (SEQ ID NO: 17) of SEQ ID NO: 2 have been synthesized. A comparison of the murine Cyr61 amino acid sequence and the human Cyr61 amino acid sequence reveals that similar domains from the human protein may be used in the design of peptides inhibiting human Cyr61. In addition, sequence comparisons may involve the human Cyr61 amino acid sequence; comparisons may also include the human homolog of Fisp12, Connective Tissue Growth Factor, also identified as a member of this protein family. O'Brien et al. (1992).

Inhibitory peptides may also be designed to compete with other ECM signalling molecules, e.g., Fisp12 or CTGF, for binding to their respective receptors. The design of inhibiting peptides is facilitated by the similarity in amino acid sequences among the ECM signalling molecules. In addition, inhibitory peptide design may be guided by one or more of the methods known in the art for identifying amino acid sequences likely to comprise functional domains (e.g., hydrophilic amino acid sequences as external/surface protein domains; sequences compatible with α-helical formation as membrane-spanning domains). These methods have been implemented in the form of commercially available software, known to those of ordinary skill in the art. See e.g., the Intelligenetics Suite of Analytical Programs for Biomolecules. Intelligenetics, Inc., Mountain View, Calif. Using these approaches, inhibitory peptides interfering with the biological activity of an ECM signalling molecule such as Cyr61, Fisp 12 or CTGF, may be designed. With the design of the amino acid sequence of an inhibitory peptide, production of that peptide may be realized by a variety of well-known techniques including, but not limited to, recombinant production and chemical synthesis. Exemplary peptides that have been shown to specifically inhibit at least one biological activity of Cyr61 include peptides exhibiting the "RGD" motif, or motif variants such as "RGDS," "RGD-SPK," "GDR," or "SGDR." (Ruoslahti, et al., *Science* 238:491–497 [1987], Ruoslahti, E., *Ann. Rev. of Cell and Dev. Biol.* 12:698–715 [1996]) as described in Example 10 above.

EXAMPLE 13

Cell Adhesion

Another embodiment of the invention is directed to the use of Cyr61 to mediate cellular attachment to the extracellular matrix. Induction of cellular adhesion was investigated using murine Cyr61, fibronectin, and bovine serum albumin (BSA). Immunological 96-well plates (Falcon brand) were coated with 50 µl of 0.1% BSA in PBS at 4° C. in the presence of 0–30 µg/ml concentrations of murine Cyr61 or fibronectin. After two hours exposure to the coating solution, non-diluted immune or pre-immune antisera (30 µl/well), or affinity-purified anti-Cyr61 antibodies were added. For some wells, the coating mixture was adjusted to 10 mM DTT or 100 mM HCl. After 16 hours incubation, the coating solution was removed and the well surface was blocked with 1% BSA in phosphate-buffered saline (PBS) for 1 hour at room temperature. HUVE cells were plated in Ham's complete F12K medium [GIBCO-BRL, Inc.; Hams, *Proc. Natl. Acad. Sci. (USA)* 53:786 (1965)] at $5 \times 10^{3-10^4}$ cells/well. Cycloheximide was added to 100 µg/ml immediately before plating and monensin was added to 1 µM 14 hours before plating. After a 2-hour incubation at 37° C., the wells were washed with PBS and attached cells were fixed and stained with methylene blue. The attachment efficiency was determined by quantitative dye extraction and measurement of the extract absorbance at 650 nm. Oliver et al., *J. Cell. Sci.* 92:513–518 (1989).

HUVE cells attached poorly to dishes treated with BSA alone, but adhered well to dishes coated with fibronectin. Murine Cyr61-coated surfaces also supported HUVE cell attachment in a dose-dependent manner, similar to fibronectin. For example, at 1 µg/ml. Cyr61 and fibronectin yielded $A_{650}$ values of 0.1. An $A_{650}$ value of 0.5 corresponded to the attachment of $6 \times 10^3$ cells. At the other end of the tested concentration range. 30 µg/ml, Cyr61 yielded an $A_{650}$ of 0.8; fibronectin yielded an $A_{650}$ of 0.9. Cyr61 also promoted the attachment of NIH 3T3 cells, though less effectively than fibronectin. Cyr61-mediated cell attachment can be observed as early as 30 minutes after plating, as visualized by light microscopy.

The adhesion of HUVE cells on murine Cyr61-coated surfaces was specifically inhibited by anti-Cyr61 antiserum and by affinity-purified anti-Cyr61 antibodies, but not by pre-immune serum. In contrast, attachment of cells to fibronectin-coated dishes was not affected by either the anti-Cyr61 antiserum or affinity-purified anti-Cyr61 antibodies. These results show that enhancement of cell adhesion is a specific activity of the Cyr61 protein. Furthermore, the Cyr61-mediated cell attachment was insensitive to cycloheximide or monensin treatment, indicating that Cyr61 does not act by inducing de novo synthesis of ECM components, stimulation of fibronectin, or collagen secretion. Rather, the data support the direct action of Cyr61 on cells in effecting adhesion. The Cyr61-mediated attachment of HUVE cells was completely abolished by the presence of EGTA; however, attachment was restored by the addition of $CaCl_2$ or $MgSO_4$ to the medium. These results indicate that the interaction between Cyr61 and its cell surface receptor requires divalent cations, consistent with the observations leading to the identification of the $\alpha_v\beta_3$ integrin as the Cyr61 receptor described in Example 10. above.

The ability of Cyr61 to promote cell adhesion, and the ability of molecules such as anti-Cyr61 antibodies to inhibit that process is exploited in an assay for modulators of cell adhesion. The assay involves a comparison of cell adhesion to surfaces, e.g., plastic tissue culture wells, that are coated with Cyr61 and a suspected modulator of cell adhesion. As a control, a similar surface is coated with Cyr61 alone. Following contact with suitable cells, the cells adhering to the surfaces are measured. A relative increase in cell adhesion in the presence of the suspected modulator, relative to the level of cell adherence to a Cyr61-coated surface, identifies a promoter of cell adhesion. A relative decrease in cell adhesion in the presence of the suspected modulator identifies an inhibitor of cell adhesion.

The identification of a Cyr61 receptor led to the development of a rapid and specific ligand-receptor assay (i.e., integrin binding assay) for Cyr61. Monoclonal antibody LM609 (anti-$\alpha_v\beta_3$) has been described. Cheresh, 1987. Monoclonal antibody JBS5 (anti-fibronectin antibody) was purchased from Chemicon. Anti-human and anti-bovine vitronectin antisera were from Gibco BRL. HRP-conjugated goat anti-rabbit antibody was from KPL. RGDSPK peptide was from Gibco BRL; RGDS and SDGR peptides were from American Peptide Company. The peptides for functional assays were dissolved in PBS at 10 mg/ml and the pH was adjusted to 7.5–8.0 with NaOH. Human plasma vitronectin was from Collaborative Biomedical Products.

$\alpha_v\beta_3$ integrin purification from HUVE cell lysates was done as described in Pytela et al., *Meth. Enzimol.*, 144: 475–489 (1987). Briefly, $10^8$ cells were lysed in 1 ml of PBS containing 1 mM $CaCl_2$, 1 mM $MgCl_2$, 0.5 mM PMSF and 100 mM octylglucoside. The lysate was passed four times through a 0.5 ml column containing RGDSPK Sepharose (prepared from the cyanogen bromide activated Sepharose CL 4 B as described in Lam, S. C. T., *J. Biol. Chem.*, 267.5649–5655 (1992). The column was washed with 10 ml of the lysis buffer and the bound protein was eluted with 2 ml of the same buffer containing 1 mM RGDS peptide at room temperature. The $\alpha_v\beta_3$ integrin was dialyzed against PBS containing 1 mM $CaCl_2$, 1 mM $MgCl_2$, 5 mM octylglucoside and 0.1 mM PMSF with three changes of the dialysis buffer to remove the RGDS peptide. The protein was stored in aliquots at –70° C. The purity of the integrin was determined by SDS-PAGE under non-reducing conditions, followed by silver staining. Western blotting with anti-CD47 antibody showed that this $\alpha_v\beta_3$ integrin preparation does not contain any integrin-associated proteins.

The integrin binding assay was developed in accordance with the disclosures in Brooks et al., *Cell* 85:683–693 (1996), and Lam, S. C.-T. (1992). Approximately 50 ng of the integrin in a total volume of 50 µl were added per well of 96-well immunological Pro-Bind plates (Falcon) and incubated overnight at 4° C. Non-specific sites were blocked with 20 mg/ml BSA in the same buffer and washed four times in that buffer. Treated plates were incubated with 1 µg/ml Cyr61 or 0.1 µg/ml vitronectin for 3 hours at room temperature. EDTA (5 mM), RGDS peptide (0.5 mM) and blocking antibodies were either preincubated with the immobilized integrin for 1 hour before the addition of the protein ligand or added along with the ligand. The final dilution of the LM609 ascites fluid was 1:200. Bound proteins were detected by specific polyclonal antisera (anti-Cyr61 antiserum was diluted 1:500 and anti-vitronectin antiserum was diluted 1:1000 in PBS containing 1 mM $CaCl_2$, 1 mM $MgCl_2$, and 5 mg/ml BSA) followed by a secondary antibody-horseradish peroxidase conjugate (1:20000 in the same buffer). Plates were rinsed four times with PBS containing 1 mM $CaCl_2$ and 1 mM $MgCl_2$ after each incubation. Horseradish peroxidase (HRP) was detected with an HRP immunoassay kit (Bio-Rad Laboratories). The colorimetric reaction was developed for 15–30 minutes at room temperature, stopped by the addition of $H_2SO_4$, and the absorbance at 450 nm was measured. Those of ordinary skill in the art will understand that a variety of detection techniques could be employed in place of the enzyme-linked immunological approach exemplified. For example, other labels such as radiolabels, fluorescent compounds and the like could be bound, e.g., covalently, to an antibody or other agent recognizing the peptide of interest such as Cyr61.

The results of integrin binding assays showed that vitronectin and Cyr61 bound to the immobilized integrin. Further, both Cyr61 and vitronectin binding to $\alpha_v\beta_3$ were saturable. The concentration of Cyr61 at which saturation was reached was significantly higher than the concentration of vitronectin required for saturation. This difference may reflect a lower affinity of $\alpha_v\beta_3$ for Cyr61 compared to vitronectin, which is in agreement with the results of cell adhesion assays, which show that HUVE cells adhere to vitronectin and, more weakly, to Cyr61, in a concentration-dependent manner (see below). The specificity of the interaction was addressed by blocking the ligand binding site of the integrin using any one of several techniques, including divalent cation deprivation, RGDS peptide competition, and LM609 antibody inhibition. The interaction of both proteins (Cyr61 and vitronectin) with $\alpha_v\beta_3$ was inhibited by EDTA, the RGDS peptide, and the LM609 antibody. These properties of the Cyr61 interaction with $\alpha_v\beta_3$ were also in agreement with the results of the cell adhesion assay and indicated that HUVE cell adhesion to Cyr61 was mediated by the direct interaction of Cyr61 with the $\alpha_v\beta_3$ integrin.

In addition, Cyr61 induces focal adhesion, i.e., cell surface foci for cytoskeletal attachments. Focal adhesion is effected by cell surface protein complexes or clusters. These protein clusters are complex, including a variety of receptors from the integrin family, and a variety of protein kinases. The induction of focal adhesion by Cyr61 is reflected in the capacity of Cyr61 to induce particular members of these cell surface protein clusters. For example, Cyr61 induces the phosphorylation of Focal Adhesion Kinase, a 125 kDa polypeptide, and Paxillin, another protein known to be involved in the focal adhesion cell surface protein complexes. Moreover, indirect immunofluorescence studies have shown that Cyr61 is bound to a receptor (see above) in focal adhesive plaques. The plaques, in turn, are characteristic of focal adhesion protein complexes. Focal Adhesion Kinase, Paxillin, and $\alpha_v\beta_3$ Integrin are co-localized to the focal adhesion plaques produced by focal adhesion complex formation induced by Cyr61. These focal adhesion protein complexes bind Cyr61 at the cell surface; the complexes also attach internally to the cytoskeleton. Therefore, murine Cyr61, and human Cyr61 (see below), are, in part, adhesion molecules, a characteristic distinguishing Cyr61 from conventional growth factors. Those of skill in the art will also recognize that the $\alpha_v\beta_3$ integrin can be used, in conjunction with Cyr61, to screen for modulators of Cyr61 binding to its receptor. In one embodiment, the integrin is immobilized and exposed to either (a) Cyr61 and a suspected modulator of receptor binding; or (b) Cyr61 alone. Subsequently, bound Cyr61 is detected. e.g., by anti-Cyr61 antibody that is labeled using techniques known in the art, such as radiolabelling, fluorescent labelling, or the use of enzymes catalyzing colorimetric reactions. A promoter of Cyr61 binding to its receptor would increase binding of Cyr61 (and an inhibitor would decrease Cyr61), relative to the binding by Cyr61 alone.

In another embodiment of the invention, the effect of murine Cyr61 on cell morphogenesis was assessed by a cell spreading assay. Polystyrene Petri dishes were coated with 2 ml of a 10 µg/ml solution of Cyr61 or fibronectin in PBS with 0.1% BSA and treated as described above. A third plate was treated with BSA and served as a control. Each dish received $7 \times 10^6$ cells and was incubated for 2 hours. Cell spreading was analyzed by microscopy at 100-fold magnification. The results indicate that murine Cyr61 induces HUVE cell spreading to approximately the same extent as fibronectin. The efficient attachment (see above) and spreading of cells on murine Cyr61-coated substrates indicated that Cyr61 may interact with a signal-transducing cell surface receptor, leading to a cascade of cytoskeletal rearrangements and possible formation of focal contacts. Consequently, Cyr61 and Cyr61-related polypeptides may prove useful in controlling cell adhesion, e.g., the cell adhesion events that accompany metastasizing cancer cells, organ repair and regeneration, or chondrocyte colonization of prosthetic implants, discussed below.

In contrast to mouse Cyr61 which mediated both HUVE cell attachment and migration, hCyr61 was found to mediate cell adhesion but not spreading of HUVE cells. Immunological plates (96-well ProBind assay plates, Falcon) were coated with 0.1–30 µg/ml hCyr61, fibronectin (Gibco BRL) or vitronectin (Gibco BRL) in phosphate-buffered saline (PBS) containing 0.1% protease-free BSA (Sigma) for 16 hrs at 4° C. The wells were blocked with 1% BSA in PBS for 1 hr at room temperature and washed with PBS. HUVE cells were harvested with 0.02% EDTA in PBS, washed twice with serum-free F12 medium and resuspended in serum-free F12. In some experiments, fbs was added to 5–10%. Also, in experiments involving vitronectin-coated plates, endogenous vitronectin was removed from fbs by immunoaffinity chromatography using bovine polyclonal anti-vitronectin antibodies (Gibco). Norris et al., *J. Cell Sci.* 95:255–262 (1990). Cells were plated at $10^4$ cells/well. After 2 hours, cells were fixed with 4% paraformaldehyde, stained with methylene blue and quantified as described. Oliver et al., *J. Cell Sci.* 92:513–518 (1989).

Under serum-free conditions. hCyr61 mediated cell attachment but not spreading of HUVE cells. Attachment of HUVE cells to hCyr61-coated plates was enhanced by inclusion of serum in the culture medium. In the presence of serum. HUVE cells attached and spread on hCyr61 in a manner similar to that seen on fibronectin. Human Cyr61 supported HUVE cell adhesion in a dose-dependent manner both under high-serum (10%) and low-serum (0.5%) conditions. However, in the presence of 10% fbs, the maximal proportion of the cells attaching at a lower concentration of hCyr61, and the proportion of the cells attached, was higher. Human Cyr61 was also found to cooperate with vitronectin in promoting HUVE cell adhesion and spreading. Two major cell-adhesive proteins found in mammalian sera are fibronectin and vitronectin, also known as "serum spreading factor." For review, see Felding-Habermann et al., *Curr. Opin. Cell Biol.* 5:864–868 (1993). Cell attachment, spreading and growth on tissue-culture plastic depended upon vitronectin, rather than fibronectin, in serum for the following reasons: (1) considerable depletion of fibronectin in the batches of fbs due to "clotting" at 4° C.; and (2) inability of fibronectin to efficiently coat the plastic in the presence of an excess amount of other serum proteins. In contrast, vitronectin coated the plastic surfaces efficiently under the same conditions.

The ability of HUVE cells to adhere to hCyr61-coated plates in the presence of mock-immunodepleted fbs and serum immunodepleted with anti-bovine vitronectin antibodies were compared. HUVE cells adhered to hCyr61- coated surfaces significantly better in the presence of soluble vitronectin or mock-immunodepleted fbs than they did in the presence of serum-free medium or medium supplemented with vitronectin-immunodepleted fbs. The addition of vitronectin (30 μg/ml) to vitronectin-immunodepleted serum restored the ability of HUVE cells to adhere and spread on hCyr61-coated plates to the same level observed when whole serum was used in the cell attachment assay. Furthermore, soluble vitronectin alone, at a concentration equal to its level in 10% serum (30 μg/ml), restored the level of cell adhesion and spreading to the level found in the presence of 10% serum. Thus, vitronectin is a necessary and sufficient serum component contributing to HUVE cell adhesion and spreading on hCyr61-coated plastic surfaces. Control studies showed that the effect of vitronectin was not due to its preferential retention on the plastic dish surfaces in the presence of hCYR61.

Additionally, HUVE cell attachment and spreading in the presence of an increasing quantity of vitronectin was examined. The solutions for coating the dishes contained increasing amounts of vitronectin (0–10 μg/ml) with a fixed amount of hCyr61 (10 μ/ml). The results indicated that more cells adhered to plates coated with the two proteins than would have been expected by adding the individual adhesive capacities of vitronectin and hCyr61. This non-additive increase of adhesion in the presence of vitronectin and hCyr61 was not due to higher amounts of vitronectin absorbed on the plastic. ELISA assay with anti-human vitronectin antibodies showed that the amount of vitronectin adsorbed to plastic dishes exposed to the vitronectin/hCyr61 mixture did not exceed that of vitronectin alone by more than 20%. This difference is insufficient to explain the observed difference in cell adhesion (3–5 fold in different experiments). In addition, a higher proportion of HUVE cells also adhered to the mixture of proteins when the coating solution contained diluted vitronectin (2.5 μg/ml) than were found to adhere to dishes coated with higher concentrations of pure vitronectin (10 μg/ml) or pure hCyr61 (10 μg/ml). Thus, vitronectin and hCyr61 functionally cooperate and exert a synergistic effect on HUVE cell adhesion.

The capacity of Fisp12 to affect cell adhesion was also investigated. Fisp12 cell attachment assays were performed essentially as described (Oliver et al. 1989). 96-well immunological plates were coated for 16 hours at 4° C. with 20 μg/ml Cyr61, Fisp12 or fibronectin (Gibco BRL) in PBS containing 0.1 mg/ml BSA and blocked with 10 mg/ml BSA for 1 hour at room temperature. HUVE cells were plated at $10^4$ cells/well in F12K media with 10% FBS (Hyclone Laboratories, Inc., Logan, Utah): NIH 3T3 fibroblasts were plated at $3 \times 10^4$ cells/well and Mv1Lu cells were plated at $5 \times 10^4$ cells/well in minimal essential medium (MEM) with 10% FBS. After 1 hour incubation cells were fixed, stained with methylene blue and quantified as described (Oliver et al. 1989). Cell spreading was examined on cells plated on 100 mm polystyrene petri dishes coated with 2.5 ml of a 20 μg/ml solution of Cyr61, Fisp12 or fibronectin. $10^7$ cells were plated on each dish and cell spreading was analyzed 90 min. after plating by microscopy at 100× magnification.

The results indicated that Fisp12, as well as Cyr61, when coated on plastic dishes, promoted the attachment of three different cell types: HUVE cells, NIH 3T3 fibroblasts, and mink lung epithelial (Mv1Lu) cells. These cells attached poorly to uncoated plastic dishes or plastic dishes coated with bovine serum albumin, but attached significantly better to dishes coated with either fibronectin, Cyr61, or Fisp12. The ability of either Cyr61 or Fisp12 to mediate cell attachment is comparable to that of fibronectin for all three cell types. While the ability of Cyr61 to mediate cell attachment was previously demonstrated for fibroblasts and endothelial cells (Kireeva et al. 1996), these studies show cell attachment activity for both Fisp12 and Cyr61 in epithelial cells in addition to endothelial cells and fibroblasts.

Like cell attachment to fibronectin and Cyr61 (Kireeva et al., 1996). Fisp 12-mediated cell attachment was inhibited when EDTA was added to the culture medium. This inhibition was completely abolished by the addition of excess $MgCl_2$, indicating a requirement for divalent cations in Fisp12-mediated cell attachment. In addition to cell attachment, Fisp12 also promotes cell spreading. Similar cell spreading was found when NIH 3T3 cells were plated on dishes coated with either fibronectin, Cyr61, or Fisp12, but not BSA. Endothelial and epithelial cells also spread when plated on fibronectin, Cyr61, or Fisp12.

EXAMPLE 14

Migration of Fibroblasts

Cyr61 also affects chondrocytes, e.g., fibroblasts involved in skeletal development. In particular, Cyr61 influences the development, and perhaps maintenance, of cartilage, in contrast to the variety of growth-related proteins that exclusively influence development and maintenance of the bony skeleton. The chemotactic response of NIH 3T3 cells to murine Cyr61 was examined using a modified Boyden chamber (Neuroprobe Inc., catalog no. AP48). Grotendorst, *Meth. Enzymol.* 147:144–152 (1987). Purified Cyr61 protein was serially diluted in DMEM containing bovine serum albumin (BSA; 0.2 mg/ml) and added to the lower well of the chamber. The lower well was then covered with a collagen-coated polycarbonate filter (8 μm pore diameter; Nucleopore Corp., Pleasanton, Calif.). Cells ($6 \times 10^4$) were then loaded into the upper well. After 5 hours incubation (10% $CO_2$, 37° C.), the filter was removed and the cells were fixed and stained using Wright-Giemsa stain (Harleco formulation; EM Diagnostic Systems, Gibbstown, N.J.). Cells from the upper surface of the filter were then removed by wiping with a tissue swab. The chemotactic response was determined by counting the total number of migrating cells detected in ten randomly selected high-power microscopic fields (400-fold magnification) on the lower surface of the filter. Duplicate trials were performed for each experiment and the experiment was repeated three times to ensure reproducibility of the data.

NIH 3T3 cells responded to Cyr61 as a chemotactic factor in a dose-dependent manner in the Boyden chamber assay. Without Cyr61, approximately 4.8 cells had migrated per high-power field. In the presence of 0.5 μg/ml murine Cyr61, about 5.2 cells were found in each field. As the concentration of Cyr61 was raised to 1, 5 and 10 μg/ml, the average number of migrating cells detected per field rose to 7.5, 18.5, and 18.7. Thus murine Cyr61 acts as a chemoattractant for fibroblasts. The optimal concentration for the chemotactic activity of Cyr61 is 1–5 μg/ml in this assay; this concentration range is consistent with the reported ranges at which other ECM molecules provide effective chemotactic stimulation. For example, Thrombospondin, at 5–50 μg/ml. has a chemotactic effect on endothelial cells (Taraboletti et al., *J. Cell Biol.* 111:765–772 (1990): fibronectin also functions as a chemotactic agent at 1–30 μg/ml (Carsons et al., *Role of Fibronectin in Rheumatic Diseases*, in Fibronectin [Mosher. ed., Academic Press 1989]; Carsons et al., *Arthritis. Rheum.* 28:601–612 [1985]) as determined using similar Boyden chamber assays. The human Cyr61 polypeptide may be used to chemoattract fibroblasts in a manner analogous to murine Cyr61. Human CTGF has also been reported to induce the migration of non-human mammalian cells such as NIH 3T3 cells (mouse fibroblasts) and BASM cells (bovine aortic smooth muscle cells), as described in U.S. Pat. No. 5,408,040, column 7, line 65 to column 11, line 7, incorporated herein by reference.

In an alternative embodiment, an assay for modulators of cell migration, such as the migration of chondrocytes, involves a combination of a suspected modulator of cell migration and Cyr61 being added to the lower well of a Boyden chamber. As a control, Cyr61 is separately added to the lower well of another Boyden chamber. Relative cell migrations are then measured. An increase in cell migration in the presence of the suspected modulator relative to cell migration in response to Cyr61 alone identifies a promoter of chondrocyte cell migration, while a relative decrease in cell migration in the presence of the suspected modulator identifies an inhibitor.

EXAMPLE 15

Migration of Endothelial Cells—In Vitro Assays

The end product of in vitro angiogenesis is a well-defined network of capillary-like tubes. When cultured on gel matrices, e.g., collagen, fibrin, or Matrigel gels, endothelial cells must first invade the matrix before forming mature vessels. (Matrigel is a complex mixture of basement membrane proteins including laminin, collagen type IV, nidogen/entactin, and proteoglycan heparin sulfate, with additional growth factors. Kleinman et al., *Biochem.* 25:312–318 (1986). The invasive structures are cords which eventually anastomose to form the vessel-like structures. The angiogenic effect of human Cyr61 on confluent monolayers of human umbilical vein endothelial cells is assessed by seeding the cells onto three-dimensional collagen or fibrin gels, in the presence or absence of Cyr61. HUVE cells do not spontaneously invade such gels but do so when induced by agents such as tumor promoters.

Collagen gels were prepared by first solubilizing type I collagen (Collaborative Research, Inc., Bedford, Mass.) in a sterile 1:1000 (v/v) dilution of glacial acetic acid (300 ml per gram of collagen). The resulting solution was filtered through sterile triple gauze and centrifuged at 16,000×g for 1 hour at 4° C. The supernatant was dialyzed against 0.1× Eagle's Minimal Essential Medium (MEM; GIBCO-BRL, Inc.) and stored at 4° C. Gels of reconstituted collagen fibers were prepared by rapidly raising the pH and ionic strength of the collagen solution. The pH and ionic strength adjustments were accomplished by quickly mixing 7 volumes of cold collagen solution with one volume of 10×MEM and 2 volumes of sodium bicarbonate (11.76 mg/ml) in a sterile flask. The solution was kept on ice to prevent immediate gelation. The cold mixture was dispensed into 18 mm tissue culture wells and allowed to gel for 10 minutes at 37° C.

Fibrin gels were prepared by dissolving fibrinogen (Sigma Chemical Co. St. Louis, Mo.) immediately before use in calcium-free MEM to obtain a final concentration of 2.5 mg of protein/ml. Clotting was initiated by rapidly mixing 1.35 ml of fibrinogen solution with 15 µl of 10×MEM containing 25 U/ml thrombin (Sigma Chemical Co.) in a plastic tube. The mixture was transferred immediately into 18 mm tissue culture wells and allowed to gel for about 2 minutes at 37° C.

In some wells. Cyr61 was mixed into the gel matrix before gelation (final concentration 10 µg/ml), while in other wells, Cyr61 was not in the gel matrix but was added as part of the nutrient medium (similar range of concentrations as in the matrix) after the cells reached confluency. HUVE cells were seeded onto the gel matrix surface at $5 \times 10^4$ cells per well in Ham's F12K medium [GIBCO-BRL. Inc.] containing 10% fetal bovine serum, 100 µg/ml heparin, and 30 µg/ml endothelial cell growth factor. When the cells reached confluency, the medium was removed, the cells were rinsed with PBS, and fresh medium without endothelial cell growth factor was supplied. Some cultures received purified recombinant Cyr61, while others received Cyr61 and polyclonal anti-Cyr61 antibodies. Thus, the variety of cultures at confluency included: a) cultures with no Cyr61; b) cultures with Cyr61 within the matrix: c) cultures with Cyr61 supplementing the medium; and d) cultures with Cyr61 supplementing the medium along with polyclonal anti-Cyr61 antibodies.

Invasion of the gel matrix was quantified about 4–7 days after treatment of the confluent cultures. Randomly selected fields measuring 1.0 mm×1.4 mm were photographed in each well under phase-contrast microscopy with a Zeiss Axiovert inverted photomicroscope. Photographs were taken at a single level beneath the surface monolayer. Invasion was quantified by measuring the total length of all cell cords that penetrated beneath the surface monolayer. Results were expressed as the mean length in microns per field for at least 3 randomly selected fields from each of at least 3 separate experiments.

In order to examine the network of cords within the matrix for capillary-like tube formation, cultures were fixed in situ overnight with 2.5% glutaraldehyde and 1% tannic acid in 100 mM sodium cacodylate buffer, pH 7.4. Cultures were then washed extensively in 100 mM sodium cacodylate buffer, pH 7.4. The gels were cut into 2 mm×2 mm fragments, post-fixed in 1% osmium tetroxide in veronal acetate buffer (to minimize tissue swelling; see Havat, in *Principles and Techniques of Electron Microscopy: Biological Applications* 1:38 [Litton Educational Publishing, Inc. 1970]) for 45 minutes, stained en bloc with 0.5% uranyl acetate in veronal buffer for 45 minutes, dehydrated by exposure to a graded ethanol series, and embedded in Epon in flat molds. Semi-thin sections were cut perpendicular to the culture plane with an ultramicrotome, stained with 1% toluidine blue, and photographed under transmitted light using an Axiophot photomicroscope (Zeiss).

In an alternative embodiment, a suspected modulator of angiogenesis is combined with Cyr61 and the combination is added before, or after, formation of a gel. In this embodiment, a control is established by using Cyr61 alone. The migration of cells in response to the suspected modulator and Cyr61 is then compared to the migration of cells in response to Cyr61 alone. A promoter or positive effector will increase cell migration while an inhibitor or negative effector will decrease cell migration.

In an alternative in vitro assay for angiogenic activity, an assay for endothelial cell migration was developed. This chemotaxis assay has been shown to detect the effects of Cyr61 concentrations on the order of nanograms per milliliter. Primary Human Microvascular Endothelial Cells (HM-VEC PO51: Clonetics, San Diego, Calif.) were maintained in DME with 10% donor calf serum (Flow Laboratories, McLean, Va.) and 100 µg/ml endothelial cell mitogen (Biomedical Technologies Inc., Stoughton, Mass.). The cells were used between passages 10 and 15. To measure migration, cells were starved for 24 hours in DME containing 0.1% BSA, harvested, resuspended in DME with 0.1% BSA, and plated at 1.75×10⁴ cells/well on the lower surface of a gelatinized 0.5 µm filter (Nucleopore Corporation, Pleasanton, Calif.) in an inverted modified Boyden chamber. After 1–2 hours at 37° C., during which time the cells were allowed to adhere to the filter, the chamber was reverted to its normal position. To the top well of separate chambers, basic Fibroblast Growth Factor (a positive control), Cyr61, or a negative control solution (conditioned medium known to lack chemoattractants or DME plus BSA, see below) was added at concentrations ranging from 10 ng/ml to 10 µg/ml. Chambers were then incubated for 3–4 hours at 37° C. to allow migration. Chambers were disassembled, membranes fixed and stained, and the number of cells that had migrated to the top of the filter in 3 high-powered fields was determined, Tolsma et al., *J. Cell. Biol.* 122:497–511 (1993) (incorporated by reference), and references cited therein. DME with 0.1% BSA was used as a negative control and either bFGF (10 ng/ml) or conditioned media from angiogenic hamster cell lines (20 µg/ml total protein) were used as positive controls, Rastinejad et al., *Cell* 56:345–355 (1989). Each sample was tested in quadruplicate (test compound such as Cyr61, positive control, conditioned medium as a negative control, and DME plus BSA as a negative control) in a single experiment; experiments were repeated at least twice.

To allow comparison of experiments performed on different days, migration data is reported as the percent of maximum migration towards the positive control, calculated after subtraction of background migration observed in the presence of DME plus BSA. Test compounds that depressed the random movement of endothelial cells showed a negative value for the percent migration. Very high concentrations of thrombospondin (TSP) caused endothelial cells to detach from the membrane. Detachment was detected by counting cells on the lower face of the membrane. When cell loss exceeded 10%, the number of migrated cells was corrected for this loss. The results indicate that 0.01–10 µg/ml bFGF induced the migration of a constant 92 cells per three high-powered microscope fields Migration in the presence of Cyr61 revealed a greater dependence on concentration. At 10 ng/ml, Cyr61 induced an average of 64 cells to migrate per three high-powered fields examined. At 100 ng/ml Cyr61, approximately 72 cells were found in three fields; at 1 µg/ml Cyr61, a peak of 87 cells had migrated; at approximately 7 µg/ml Cyr61, about 61 cells were observed; and at 10 µg/ml Cyr61, approximately 57 cells were found to have migrated. The negative control revealed a constant basal level of endothelial cell migration of 53 cells per three high-powered microscope fields. In addition to these results, there is a perfect correlation of the results from this in vitro assay and the results from the in vivo cornea assay, described below.

To monitor toxicity, endothelial cells were treated with each of the tested compounds at a range of concentrations, under conditions identical to those used in the migration assay. Cells were then stained with Trypan blue and cells excluding Trypan blue were counted. The results showed that cells remained viable and that the inhibition of migration could not be attributed to toxicity. Where relevant, endothelial cells were pretreated for 36–48 hours with peptides at 20 µM in DME with 0.1% BSA before use in the migration assays. Toxicity was also tested over these time frames and found to be negligible.

The ability of Cyr61 to induce matrix invasion and tube formation by HUVE cells, as well as the ability of Cyr61 to induce human microvascular endothelial cells to migrate, demonstrates the angiogenic properties of this protein. It is anticipated that other members of the ECM signalling molecule family of cysteine-rich proteins, such as Fisp12 and CTGF, have similar properties that may be used in methods of the invention for screening for, and modulating, angiogenic conditions. In particular, one of ordinary skill in the art understands that an in vitro assay for angiogenic inhibitors involves the assay described above, including an effective amount of Cyr61, with and without the candidate inhibitor.

EXAMPLE 16

Migration of Endothelial Cells—An In Vitro Assay For Angiogenesis Inhibitors

The inclusion of an effective amount of an ECM signalling molecule, such as Cyr61 in the in vitro migration (i.e., chemotaxis) assay described in the preceding Example, provides an assay designed to detect inhibitors of ECM signalling molecules and angiogenesis. Because of the crucial role of neovascularization in such processes as solid tumor growth and metastasis, the development of assays to detect compounds that might antagonize these processes would be useful.

The above-described in vitro migration assay was adapted to include an ECM signalling molecule, Cyr61. Cyr61 was included at 1 µg/ml, which was found to be the optimal dosage in titration studies. As in the preceding Example, human microvascular endothelial cells (Clonetics) were used. In one series of assays, several carbohydrates and carbohydrate derivatives were analyzed. These compounds included 10 mM mannose, 10 mM mannose-6-phosphate, and 10 mM galactose. Results of these assays showed that Cyr61 plus mannose yielded approximately 73 cells per set of three high-powered microscope fields (see above). Cyr61 plus galactose induced the migration of approximately 74 cells per set of three high-powered fields. However, Cyr61 plus mannose-6-phosphate yielded approximately 2 migrating cells for each set of three high-powered fields examined. Control experiments demonstrate that the inhibition of Cyr61 activity by mannose-6-phosphate is specific.

The angiogenic activity of basic FGF (10 ng/ml) was also tested, as described above, with and without mannose-6-phosphate. In the presence of 10 mM mannose-6-phosphate, bFGF induced 51 cells per set of three high-powered fields to migrate; in its absence, bFGF induced the migration of approximately 52 cells. However, when either Cyr61 or Insulin Growth Factor II (IGF-II) were tested, mannose-6-phosphate reduced the number of migrating cells from approximately 48 or 47 cells, respectively, to approximately 12 or 11 cells, respectively. The effect of mannose-6-phosphate on IGF II activity was anticipated because mannose-6-phosphate is known to compete with IGF II for their common receptor (the IGF II receptor). Thus, mannose-6-phosphate specifically inhibits the chemotactic activity of Cyr61 on human endothelial cells. Moreover, because there is an essentially perfect correlation between the in vitro migration assay and the in vivo angiogenesis assay, described below, mannose-6-phosphate has been identified as an inhibitor of angiogenesis based on the results of the assay disclosed herein. Accordingly, the invention contemplates a method of inhibiting angiogenesis comprising the step of administering an inhibitor the angiogenic activity of Cyr 61 such as mannose-6-phosphate. Assays such as that described above may also be used to screen for other inhibitors of angiogenesis which may be useful in the treatment of diseases associated with angiogenesis such as cancer, and diseases of the eye which are accompanied by neovascularization.

In an embodiment of the invention, a method of screening for modulators of angiogenesis involves a comparative assay. One set of conditions involves exposure of cells to a combination of Cyr61 and a suspected modulator of cell migration. As a control, a parallel assay is performed that exposes cells to Cyr61 alone. A promoter of cell migration elevates the rate of in vitro cell migration relative to the rate of migration in the presence of Cyr61 alone, the converse is true for an inhibitor of the chemoattracting ability of Cyr61.

EXAMPLE 17

Migration of Endothelial Cells—An In Vivo Assay

An in vivo assay for endothelial cell migration has also been developed. In general, the assay protocol is consistent with the disclosure of Tolsma et al. 1993. To assess angiogenesis associated with the formation of granulation tissue (i.e., the newly formed, proliferative, fibroblastic dermal tissue around wounds during healing), sponge implants were used as previously described (Fajardo, et al., *Lab. Invest.* 58:718–724 [1988]). Polyvinyl-alcohol foam discs (10-mm diam×1-mm thick) were prepared by first removing a 2-mm diameter central core of sponge. PBS or an RGDS peptide (other possible test compounds include fragments of Cyr61, RGDS peptide, small molecules such as mannose-6-phosphate) at 100 µM were added to the sponge core which was then coated with 5 µl of sterile Hydron (Interferon Sciences, New Brunswick. N.J.). After solidifying, the coated core was returned to the center of the sponge which was then covered on both sides with 5 µm filters and secured in place with glue (Millipore Corp., Bedford, Mass.). One control and one test disc were then implanted subcutaneously in the lower abdomen of anesthetized Balb/c female mice where granulation tissue could invade the free perimeter of the disc. Wounds were closed with autoclips and animals left undisturbed until sacrificed.

Quantitative estimates of thymidine incorporation in situ into endothelial cells in the discs were obtained as previously described (Polverini, et al, *J. Immunol.* 118:529–532 [1977]). Sponge implants were evaluated at days 5, 7, 10, and 14 after implantation. Thirty minutes before sacrifice, mice were injected with a solution containing [$^3$H]-thymidine in saline (specific activity 6.7 Ci/mM; New England Nuclear/Du Pont, Wilmington, Del.) to a level of 1 µCi per gram of body weight. Sponges were removed and facially embedded to provide a uniform section of the entire circumference. Tissues were fixed in 10% neutral buffered formalin, dehydrated through a graded series of alcohols, and embedded in glycol methacrylate (Polysciences. Miles. Ill.). Autoradiograms were prepared by dipping sections mounted on acid-cleaned glass slides into NTB type 2 emulsion (Eastman Kodak). After exposure for 4 weeks at 4° C., autoradiographs were developed in half strength D-19 developer, fixed in Kodak Rapid Fixer, and stained with hematoxylin and eosin. Quantitation of endothelial cell labeling was performed by counting all endothelial cells that lined capillaries and venules extending from the periphery to the center of the sponge by rectilinear scanning under oil immersion (×1.000). A total of 500–700 endothelial cells were counted in each of two sponges containing either PBS, TSP, or peptide fragments (i.e., thrombospondin fragments). Cells were considered labeled if five or more grains were detected over the nucleus. The percentage of labeled cells was calculated and a chi-square analysis of data derived from control and experimental sponges was performed.

The results of the foregoing assay established that thrombospondin fragments could inhibit the process of angiogenesis. More generally, one of ordinary skill in the art would appreciate that the scope of the present invention extends to such in vivo assays for suspected modulators of ECM signalling molecule activities, such as the chemotactic ability of Cyr61 to induce cell migration. As with other assays of the invention, a comparative assay involves exposure of cells, in vivo, to a sponge laden with Cyr61 in the presence or absence of a suspected modulator of Cyr61 activity. Following implantation, incubation, and removal, the relative rates of cell migration are determined. A promoter of Cyr61 activity will increase the rate of cell migration relative to cell migration induced by Cyr61 alone; an inhibitor will decrease the rate of cell migration relative to the level ascribable to Cyr61 alone.

EXAMPLE 18

Mitogen Potentiation

In another aspect of the invention, murine Cyr61 enhanced the mitogenic effect of growth factors on fibroblasts and endothelial cells. When NIH 3T3 fibroblasts or HUVE cells were treated with a non-saturating dose of either basic Fibroblast Growth Factor (bFGF) or Platelet-Derived Growth Factor (PDGF-BB), the addition of murine Cyr61 significantly increased the incorporation of radiolabeled thymidine compared to cells treated with the growth factors alone. The thymidine incorporation assay is a standard technique for determining whether cells are actively growing by assessing the extent to which the cells have entered the S phase and are synthesizing DNA. The Cyr61 enhancement of bFGF- or PDGF-BB-induced thymidine incorporation was dose dependent, requiring a minimum concentration of 0.5–1.0 µg/ml of recombinant protein for either cell type. The enhancement of DNA synthesis by Cyr61 was inhibited by the addition of specific anti-Cyr61 antiserum.

More specifically, NIH 3T3 fibroblast cells were plated on 24-well plates at 3×10$^4$ cells/well and grown in DMEM with 10% fetal bovine serum (Intergen Co., Purchase, N.Y.) for 3–4 days and incubated with medium containing 0.2% FBS for the following 48 hours. The following compounds, at the parenthetically noted final concentrations, were then added to the plated cells in fresh DMEM containing 0.2% fbs and [$^3$H]-thymidine 1 µCi/ml final concentration: ICN Biomedicals, Inc., Costa Mesa, Calif.): bFGF (15 ng/ml), PDGF-BB (30 ng/ml), and murine Cyr61 (0.5–5 µg/ml). These compounds were added to individual plates according to the following pattern: 1) no supplementation; 2) murine Cyr61; 3) bFGF; 4) murine Cyr61 and bFGF; 5) PDGF-BB: and 6) murine Cyr61 and PDGF. After 18–20 hours of incubation, cells were washed with PBS and fixed with 10% trichloroacetic acid. DNA was dissolved in 0.1 N NaOH and thymidine incorporation was determined. The results indicated that murine Cyr61, in the absence of a growth factor, did not stimulate DNA synthesis as measured by tritiated thymidine incorporation. Without any supplements. 3T3 cells incorporated approximately 1.8×10$^4$ cpm of [$^3$H]-thymidine, in the presence or absence of Cyr61. Cells exposed to bFGF alone incorporated about 1.2×10$^5$ cpm: cells contacting bFGF and murine Cyr61 incorporated 2×10$^5$ cpm. Cells receiving PDGF-BB incorporated about 1.2×10$^5$ cpm; and cells exposed to PDGF-BB and murine Cyr61 incorporated approximately $2.4 \times 10^5$ cpm. Therefore, murine Cyr61 did not function as a mitogen itself, but did potentiate the mitogenic activity of bFGF and PDGF-BB, two known growth factors.

The ability of murine Cyr61 to potentiate the mitogenic effect of different levels of bFGF also revealed a threshold requirement for the growth factor. Human umbilical vein endothelial cells were plated essentially as described above for 3T3 cells and exposed to a constant amount of murine Cyr61: controls received no Cyr61. Different plates were then exposed to different levels of bFGF, comprising a series of bFGF concentrations ranging from 0–10 ng/ml. Following culture growth in the presence of $[^3H]$-thymidine for 72 hours, cells exposed to 0–0.1 ng/ml of bFGF exhibited a baseline level of thymidine incorporation (approximately $4 \times 10^2$ cpm), in the presence or absence of Cyr61. At 1 ng/ml bFGF, however, HUVE cells increased their thymidine incorporation in the presence of bFGF to $6 \times 10^2$ cpm; in the presence of 1 ng/ml bFGF and murine Cyr61, HUVE cells incorporated $1.3 \times 10^3$ cpm. At 10 ng/ml bFGF, cells exposed to bFGF incorporated about $1.8 \times 10^3$ cpm thymidine: cells receiving 10 ng/ml bFGF and Cyr61 incorporated approximately $6.1 \times 10^3$ cpm.

The capacity of murine Cyr61 to potentiate the mitogenic activity of bFGF was verified by a thymidine incorporation assay involving HUVE cells and various combinations of bFGF, Cyr61, and anti-Cyr61 antibodies. Cells were plated and grown as described above. The following combinations of supplements (final plate concentrations noted parenthetically) were then pre-incubated for 1 hour before addition to individual plates: 1) pre-immune antiserum (3%); 2) bFGF (15 ng/ml) and pre-immune antiserum (3%); 3) pre-immune antiserum (3%) and Cyr61 (4 µg/ml): 4) pre-immune antiserum (3%), Cyr61 (4 µg/ml), and bFGF (15 ng/ml): 5) anti-Cyr61 antiserum (3%); 6) anti-Cyr61 antiserum and bFGF (15 ng/ml): 7) anti-Cyr61 antiserum (3%) and Cyr61 (4 µg/ml); and 8) anti-Cyr61 antiserum (3%). Cyr61 (4 µg/ml), and bFGF (15 ng/ml).

Following incubation in the presence of $[^3H]$-thymidine as described above, cells exposed to pre-immune antiserum incorporated about $2 \times 10^2$ cpm thymidine; cells contacting pre-immune antiserum and bFGF incorporated $1.3 \times 10^3$ cpm; cells receiving pre-immune antiserum and Cyr61 incorporated $1 \times 10^2$ cpm; cells receiving pre-immune antiserum. Cyr61, and bFGF incorporated $3.6 \times 10^3$ cpm; cells exposed to anti-Cyr61 antiserum incorporated $2 \times 10^2$ cpm: cells receiving anti-Cyr61 antiserum and bFGF incorporated about $1.3 \times 10^3$ cpm; cells contacting anti-Cyr61 antiserum and Cyr61 incorporated about $1 \times 10^2$ and cells receiving anti-Cyr61 antiserum. Cyr61, and bFGF incorporated $1 \times 10_3$ cpm. These results indicate that pre-immune antiserum had no effect on Cyr61-induced potentiation of bFGF mitogenic activity. Anti-Cyr61 antiserum, however, completely abolished the potentiation of bFGF by Cyr61. Moreover, the effect of anti-Cyr61 antiserum was specific to Cyr61-induced mitogenic potentiation because anti-Cyr61 antiserum had no effect on the mitogenic activity of bFGF per se. Therefore, Cyr61 can be used as a reagent to screen for useful mitogens.

DNA synthesis for HUVE cells and NIH 3T3 fibroblasts was measured by thymidine incorporation as described previously (Kireeva et al., Mol. Cell. Biol. 16: 1326–1334 [1996]) with minor modifications. HUVE cells were grown in 24-well plates to a subconfluent state, serum-starved for 24 hours and treated with F12K medium containing 10% fetal bovine serum (FBS), 1 µCi/ml $[^3H]$-thymidine and 10 ng/ml basic Fibroblast Growth Factor (bFGF) (Gibco-BRL, Inc.) with various concentrations of Cyr61 and Fisp12 as indicated. NIH 3T3 fibroblasts were grown to subconfluence, serum-starved for 48 hours, and treated with Minimal Essential Medium (MEM) containing 0.5% FBS, 1 µCi/ml $[^3H]$thymidine, bFGF and various concentrations of Cyr61 or Fisp12. Thymidine incorporation into the trichloroacetic acid-insoluble fraction was determined after 24 hour incubation. Logarithmically grown mink lung epithelial cells (Mv1lu. CCL64) were treated with various concentrations of TGF-β1 (Gibco-BRL) and 2 µg/ml of Cyr61 or Fisp12 for 18 hours: $[^3H]$-thymidine was then added to 1 µCi/ml for 2 hours. Thymidine incorporation was determined as described above.

Purified recombinant Fisp12 protein did not exhibit any mitogenic activity under any tested assay conditions. Rather, Fisp12 was able to enhance DNA synthesis induced by fibroblast growth factor in either NIH 3T3 fibroblasts or HUVE-cells. This activity was nearly indistinguishable from that exhibited by Cyr61.

Whereas in fibroblasts and endothelial cells, Cyr61 and Fisp12 enhance growth factor-induced DNA synthesis, both proteins can also enhance growth factor-mediated actions in another way. It is known that TGF-β acts to inhibit DNA synthesis in epithelial cells (Satterwhite et al., 1994). It was observed that both Cyr61 and Fisp12 enhanced the ability of TGF-β to inhibit DNA synthesis in mink lung epithelial cells. The data demonstrate that both recombinant Cyr61 and Fisp12. purified from serum-free sources, are not mitogenic by themselves, but have the ability to synergize with the actions of polypeptide growth factors. Cyr61 and Fisp12 enhance DNA synthesis induction by FGF, and enhance DNA synthesis inhibition by TGF-β.

The present invention also comprehends the use of CTGF in methods to potentiate the mitogenic effect of true growth factors, or to screen for true growth factors. Those contemplated uses are in contrast to the reported use of CTGF as a mitogen or growth factor itself. U.S. Pat. No. 5,408,040, column 7, line 65, to column 11, line 7, incorporated herein by reference hereinabove.

Further, the invention comprehends methods of screening for modulators of mitogen potentiation. A comparative assay exposes subconfluent cells to an ECM signalling molecule such as Cyr61, a growth factor, and a suspected modulator of an ECM signalling molecule. As a control, similar cells are exposed to the ECM signalling molecule and the growth factor. A further control exposes similar cells to the growth factor and the suspected modulator in the absence of the ECM signalling molecule. Based on the relative cell proliferation rates, as measured by, e.g., $[^3H]$-thymidine incorporation, an identification of a suspected modulator as a promoter of mitogen potentiation (elevated cell proliferation in the presence of all three molecules) or an inhibitor of mitogen potentiation (decreased cell proliferation in the presence of the three molecules) can be made.

EXAMPLE 19

Cornea Assay For Angiogenic Factors And Modulators

Another assay for modulators of angiogenesis is an in vivo assay for assessing the effect of a suspected modulator in the presence of an ECM signalling molecule-related biomaterial, such as Cyr61, on angiogenesis is the Cornea Assay. The Cornea Assay takes advantage of the absence of blood vessels in the cornea, which in the presence of an angiogenic factor, results in the detectable development of capillaries extending from the sclera into the cornea. Friedlander et al., *Science* 270:1500–1502 (1995). This ingrowth of new blood vessels from the sclera can be microscopically monitored. Further, the visually determined rate of migration can be used to assess changes in the rate of angiogenesis. These cornea assays may be performed using a wide variety of animal models. Preferably, the cornea assays are performed using rats. By way of example, an assay for suspected modulators of Cyr61 using this assay is disclosed. To perform this assay, Cyr61 is initially titrated using primary capillary endothelial cells to determine effective concentrations of Cyr61. Subsequently, Cyr61, in the presence or absence of a suspected modulator, is surgically implanted into the corneas of mammalian laboratory animals, e.g., rabbits or rats. In a preferred embodiment, Cyr61 (or Cyr61 and a suspected modulator) is embedded in a biocompatible matrix, using matrix materials and techniques that are standard in the art. Subsequently, eyes containing implants are visually observed for growth of the readily visible blood vessels within the eye. Control implantations may consist of physiologically balanced buffers embedded in the same type of matrix and implanted into eyes of the same type of laboratory animal receiving the Cyr61-containing implants.

The development of an in vivo cornea assay for angiogenic factors has advantages over existing in vitro assays for these factors. The process of angiogenesis involves four distinct phases: induction of vascular discontinuity, endothelial cell movement, endothelial cell proliferation, and three-dimensional restructuring and sprouting. In vitro assays can evaluate only two of these steps: endothelial cell migration and mitogenesis. Thus, to provide a comprehensive assay for angiogenic factors, an in vivo assay such as the cornea assay is preferred.

The cornea assay has been used to confirm the effect of angiogenic factors such as Cyr61, Fisp12, CTGF, and Nov, on the process of angiogenesis. Moreover, modifying the cornea assay by including any of these angiogenic factors and a suspected modulator of their activity results in a cornea assay for modulators of angiogenesis. For example, in one embodiment of the invention, dose of an angiogenic factor such as Cyr61 could be used in cornea assays for positive effectors of the angiogenic activity of Cyr61. An appropriate dose of Cyr61 would initially be determined by titration of the dose response relationship of Cyr61 with angiogenic events. Inclusion of a control assay lacking Cyr61 would eliminate compounds having a direct effect on angiogenesis. In an alternative embodiment of the invention, an effective dose of an angiogenic factor such as Cyr61 could be used to assay for negative modulators of the activity of an angiogenic factor. In yet another alternative embodiment, a corneal implant comprises Cyr61 and another corneal implant comprises Cyr61 and a suspected modulator of angiogenesis. Measurements of the development of blood vessels in the implanted corneas provides a basis for identifying a suspected modulator as a promoter of angiogenesis (elevated blood vessel development in the cornea containing an implant comprising the suspected modulator. A relative decrease in blood vessel development identifies an inhibitor of angiogenesis.

The rat is preferred as the animal model for the cornea assay. Disclosures in the art have established the rat model as a well-characterized system for analyzing angiogenesis. Parameters such as implant size, protein release dynamics, and suitable surgical techniques, have been well characterized. Although any strain of rat can be used in the cornea assay, preferred strains will be well-characterized laboratory strains such as the Sprague-Dawley strain.

Although rats of various sizes can be used in the cornea assay, a preferred size for the rats is 150–200 g/animal. Anesthesia is induced with Methoxyflurane and is maintained for 40–60 minutes with sodium pentobarbital (50 mg/kg. delivered intraperitoneally). The eyes are gently opened and secured in place by clamping the upper eyelid with a non-traumatic hemostat. Two drops of sterile propraracaine hydrochloride (0.5%) are then placed on each eye as to effect local anesthesia. Using a suitable surgical blade such as a No. 11 Bard Parker blade, an approximately 1.5 mm incision is made approximately 1 mm from the center of the cornea. The incision extends into the stroma but not through it. A curved iris spatula approximately 1.5 mm in width and approximately 5 mm in length is then inserted under the lip of the incision and gently blunt-dissected through the stroma toward the outer canthus of the eye. Slight finger pressure against the globe of the eye helps to steady the eye during dissection. The spatula penetrates the stroma no more than approximately 2.5 mm. Once the cornea pocket is made, the spatula is removed and the distance between the limbus and base of the pocket is measured to make sure the separation is at least about 1 mm.

To provide slow release of the protein after implantation in the cornea, protein is mixed with poly-2-hydroxyethylmethacrylate (Hydron), or an equivalent agent, to form a pellet of approximately 5 µl. Implants made in this way are rehydrated with a drop of sterile lactated Ringers solution and implanted as described above. After implantation, the corneal pocket is sealed with erythromycin ointment. After implantation, the protein-Hydron pellet should remain near the limbus of the cornea (cornea-sclera border) and vision should not be significantly impaired.

Following surgery, animals are examined daily for seven days with the aid of a stereomicroscope to check for inflammation and responses. To facilitate examination, the animal is anesthetized with Methoxyflurane and the anesthetic is continuously administered by nose cone during examination. During this seven day period, animals are monitored for implant position and corneal exudate. Animals exhibiting corneal exudate are sacrificed. A preferred method of euthanasia is exsanguination. Animals are initially anesthetized with sodium pentobarbital (50 mg/kg) and then perfused, as described below.

After seven days, animals are perfused with colloidal carbon (e.g., India Ink). Anesthesia is induced with Methoxyflurane, and is maintained with sodium pentobarbital (50 mg/kg, intraperitoneally). Each animal is perfused with 100–200 ml warm (37° C.) lactated Ringers solution per 150 g of body mass via the abdominal aorta. Once the snout of the animal is completely blanched, 20–25 ml of colloidal carbon is injected in the same way as the Ringers solution, until the head and thoracic organs are completely black. Eyes are then enucleated and fixed. Corneas are excised, flattened, and photographed.

Each protein is typically tested in three doses, in accordance with the practice in the art. Those of ordinary skill in the art realize that six positive corneal responses per dose are required to support an identification of an angiogenic response. An exemplary cornea assay includes three doses of the protein under study, with six rats being tested at each dose. Additionally, six animals are exposed to a buffer-Hydron implant and serve as negative controls. Exposure of at least three animals to a known angiogenic factor-Hydron implant serve as positive controls. Finally, to demonstrate the specificity of any observed response, six animals are exposed to implants containing a single dose of the protein under study an excess of neutralizing antibody, and Hydron.

A cornea assay as described above was performed to assess the ability of Cyr61 to induce angiogenesis. Four animals were given negative control implants containing a buffer-Hydron pellet (both eyes). Each of these animals failed to show any blood vessel development in either eye after seven days. Six animals received implants containing a biologically effective amount of Fibroblast Growth Factor (0.15 µM) in one eye and a control pellet in the other eye: all six showed angiogenic development in the eye receiving FGF, none showed neovascularization in the eye receiving the negative control. Seven animals received 1 µg/ml Cyr61 in one eye and all seven of these eyes showed blood vessel growth; one of the seven eyes receiving a negative control showed angiogenic development. Finally, four animals received implants locally releasing 1 µg/ml Cyr61 (Hydron prepared with a 10 µg/ml Cyr61 solution) and a specific anti-Cyr61 antibody in three-fold excess over Cyr61: none of the eyes of this group showed any angiogenic development. Thus, the in vivo assay for angiogenesis identifies angiogenic factors such as FGF and Cyr61. The assay also is able to reveal inhibition of angiogenic development induced ECM signalling molecules such as Cyr61.

EXAMPLE 20

Blood Clotting

ECM signalling molecules are also useful in correcting hemostasis, or abnormal blood clotting. A defect in blood clotting caused by, e.g., low level expression of cyr61 which thereby allows Tissue Factor Pathway Inhibitor (TFPI) to act unchecked can be corrected by expression or use of recombinant Cyr61 protein.

Cyr61 can interact with TFPI, a protein that inhibits extrinsic blood coagulation. TFPI inhibits blood clotting in a two step process. First, TFPI binds to factor Xa and the TFPI:Xa complex then interacts with the Tissue Factor (TF):Factor VIIa complex, thereby inhibiting the latter complex. The TF:Factor VIIa complex is the complex that activates factors IX and X. By inhibiting TF:VIIa, TFPI regulates coagulation by preventing the activation of Factors IX and X, required for blood clotting. The interaction of Cyr61 with TFPI inhibits the activity of TFPI, thus promoting blood coagulation. Cyr61 is, thus, a tissue factor agonist.

Because of the interaction of Cyr61 and TFPI, Cyr61 can control the ability of TFPI to inhibit coagulation, thereby regulating hemostasis. A defect in Cyr61 may lead to the inability to inhibit TFPI at the appropriate time, resulting in excessive inhibition of tissue factor, thereby preventing clot formation. Deregulated expression of Cyr61 will conversely inhibit the activity of TFPI constitutively, and thus tissue factor is constantly active, resulting in excessive clotting. When the expression of Cyr61 in endothelial cells is deregulated, one possible outcome is thrombosis.

In addition to Cyr61, other ECM signalling molecules, such as Fisp12 and CTGF, have been shown to exert effects on cells participating in angiogenesis. Consequently, it is anticipated that a variety of ECM signalling molecule-related biomaterials, alone or in combination, may be used in the methods of the invention directed towards modulating hemostasis.

EXAMPLE 21

Ex vivo Hematopoietic Stem Cell Cultures

To investigate the effect of Cyr61 on the growth of primitive multipotent stem cells, several assays that distinguish these cells from more mature progenitor cells in a hematopoietic culture are employed. These assays make use of physicochemical (fibronectin-binding) or growth and development-related (generation of progenitor blast colonies) differences between immature and mature subsets of cells.

Two cell lines which require conditioned media for growth are used as a source of hematopoietic stem cells (HSC). These cloned, factor-dependent murine lines are B6Sut (cloned from long term bone marrow culture and capable of growing in liquid medium without differentiation, but multipotent in agar, as described in Greenberger et al, *Proc. Natl. Acad. Sci. [USA]* 80:2931 [1983]), and FDCP-mix (cloned from long term bone marrow culture cells infected with the recombinant virus src-MoMuLV, and are multipotent in agar cultures, as described in Spooncer et al., *Nature* 310:2288 [1984]). B6Sut cells are propagated in Kincaid's medium with 10% fetal calf serum (FCS) and 10% 6×-concentrated WEHI-conditioned medium. Greenberger et al. FDCP-mix cells are propagated in Fischer's medium with 20% horse serum and 10% 6×-concentrated WEHI-conditioned medium. The cell lines are propagated at 37° C. 5% $CO_2$.

Various ex Vivo or in Vitro cultures are assayed for population growth in the presence or absence of exogenously supplied murine Cyr61 or polyclonal anti-Cyr61 antibodies. Under limiting dilution conditions, the cobblestone area forming cell (CAFC) assay is used to identify cells with long term repopulating ability. Ploemacher et al., *Blood* 74:2755 (1989): Ploemacher et al., *Blood* 78:2527 (1991). Cells identified as having long term repopulating ability by the CAFC assay are then analyzed by measuring three parameters: Rate of population doubling, mitotic index, and rate of DNA synthesis.

Long term cultures, with or without supplementation with Cyr61, are assayed for their levels of primitive HSC in the CAFC assay, van der Sluijs et al., *Exp. Hematol.* 22:1236 (1994). For example, M2-10B4 stromal cells, B6Sut, and FDCP-mix are each subjected to the CAFC assay in the following manner, described for the M2-10B4 cell line. Stromal cell layers are prepared by inoculating $5 \times 10^5$ M2-10B4 stromal cells (a cell line cloned from bone marrow stroma, Sutherland et al. *Blood* 78:666 [1991]) into each well of a 96-well culture plate in DMEM with 10% FCS. When the cells approach confluency, they are rinsed with PBS and irradiated (20 Gy of gamma-irradiation, 1.02–1.04 Gy/minute) to prevent replication of any hematopoietic cells within the stroma, without affecting the stroma's ability to support hematopoiesis.

Hematopoietic stem cells are added to the irradiated stromal cells in DMEM with 10% FCS, in the presence or absence of Cyr61 (10 µg/ml final concentration). Population doubling rates are determined. e.g., by microscopic examination of cell morphology to determine the numbers of long term repopulating cells (and more mature short term progenitor cells) present in the various experimental long term cultures. Subsequent investigation of the expansion and differentiation capacities of the potential long term HSC cultures is used for confirmation of suitable candidate cell lines.

The mitotic index is determined according to procedures standard in the art. Keram et al., *Cancer Genet. Cytogenet.* 55:235 (1991). Harvested cells are fixed in methanol:acetic acid (3:1, v:v), counted, and resuspended at $10^6$ cells/mil in fixative. Ten microliters of this suspension is placed on a slide, dried, and treated with Giemsa stain. The cells in metaphase are counted under a light microscope, and the mitotic index is calculated by dividing the number of metaphase cells by the total number of cells on the slide. Statistical analysis of comparisons of mitotic indices is performed using the 2-sided paired t-test.

The rate of DNA synthesis is measured using a thymidine incorporation assay. Various cultures are propagated in 1 µCi/ml [$^3$H]-thymidine (ICN Biomedicals, Inc., Costa Mesa, Calif.) for 24–72 hours. Harvested cells are then rinsed with PBS and fixed with 10% trichloroacetic acid. DNA is dissolved in 0.1 N NaOH, and thymidine incorporation is determined, for example by liquid scintillation spectrophotometry.

The use of an ECM signalling molecule-related biomaterial. such as Cyr61, can be used in the ex vivo expansion of hematopoietic stem cell cultures. In addition, more than one ECM signalling molecule-related biomaterial may be used to expand these cultures. For example. Cyr61, with its expression targeted locally, may be combined with Fisp12, which exhibits a more expansive targeting as evidenced by the presence of Fisp12 in culture media. As an alternative, CTGF may be substituted for Fisp12, its mouse ortholog. One of skill in the art would be able to devise other combinations of ECM signalling molecule-related biomolecules that are within the spirit of the invention.

Those of ordinary skill in the art will recognize that the successful expansion of hematopoietic stem cell cultures in the presence of ECM signalling molecules such as Cyr61 provides a basis for a method of screening for suspected modulators of that expansion process. As in the other methods of the invention, a suspected modulator is combined with an ECM signalling molecule such as Cyr61 and exposed to primitive cells. In parallel, the ECM signalling molecule is exposed to similar cells. The relative rates of expansion may be used to identify a promoter, or inhibitor, of the ability of the ECM signalling molecule to expand pluripotent hematopoietic stem cell cultures.

Cyr61, alone or in combination with other hematopoietic growth factors, may also be used to expand stem cell populations taken from a patient and which may, after expansion, be returned to the patient or other suitable recipient patient after for example, chemotherapy or other treatment modalities that result in the depletion of blood cells in a patient. Stem cell populations expanded according to the present invention may also be used in bone marrow transplants in a patient in need thereof.

EXAMPLE 22

Organ regeneration

The role of Cyr61 in the various cellular processes invoked by changes in the cellular growth state indicate that this protein would be effective in promoting organ regeneration. Towards that end, studies were conducted to determine the expression profile of murine cyr61 in remaining liver tissue following a partial hepatectomy. (The response of remaining liver tissue following partial hepatectomy is a model for the liver's response to a variety of injuries, including chemical injuries, e.g., exposure to toxic levels of carbon tetrachloride.)

BALB/c 3T3 (Charles River) mice were subjected to partial hepatectomies removing approximately 67% of their liver tissue. Higgins et al., *Archs. Path.* 12:186–202 (1931). Twenty microgram aliquots of RNA were removed from the remaining liver tissue at varying times following the operation and liver RNA was isolated by tissue homogenization followed by guanidinium isothiocyanate, cesium chloride precipitation. Sambrook et al. RNAs were then immobilized on nitrocellulose filters and probed with radiolabeled clones containing various regions of murine cyr61 cDNA. Results were visualized by autoradiography and indicated that removal of liver tissue induced cyr61 mRNA expression, particularly in cells found near the injury site. Consequently, induction of cyr61 expression, e.g., by recombinant techniques, might promote the regeneration of organs such as liver. For example, Cyr61 expression can be controlled, e.g., by introducing recombinant cyr6 constructs that have been engineered to provide the capacity to control expression of the gene, e.g., by the use of tissue-specific promoters, e.g., the K14 promoter for expression in skin. The recombinant cyr61 may be introduced to cells of the relevant organ by gene therapy techniques using vectors that facilitate homologous recombination (e.g., vectors derived from Herpesviruses, Adenoviruses, Adeno-associated Virus, Cytomegalovirus, Baculovirus, retroviruses, Vaccinia Virus, and others). Techniques for introducing heterologous genes into eukaryotic cells, and techniques for integrating heterologous genes into host chromosomes by homologous recombination, are well known in the art.

The development of skin, another organ, is also affected by Cyr61. The expression of Cyr61 is induced in cells in the vicinity of skin injuries. Also, as described above, Cyr61 has a chemotactic effect (i.e., Cyr61 induces cell migration) on endothelial cells and fibroblasts. Further, Cyr61 induces the proliferation of endothelial cells and fibroblasts. Both processes are involved in the healing of skin wounds. Accordingly, Cyr61 administration. e.g., by localized or topical delivery, should promote skin regeneration.

Cyr61 is also highly expressed in lung epithelium. These cells are frequently injured by exposure to environmental contaminants. In particular, lung epithelium is frequently damaged by air-borne oxidants. The administration of Cyr61. e.g., in atomizers or inhalers, may contribute to the healing of lung epithelium damaged, e.g., by environmental contaminants.

EXAMPLE 23

Chondrogenesis—ECM Signalling Molecules Are Expressed in Mesenchyme

Some ECM signalling molecules are also expressed in cells, such as Mesenchyme cells, that ultimately become a part of the skeletal system. In this Example, Cyr61 is identified as one of the ECM signalling molecules expressed in mesenchyme cells. Limb mesenchymal cells were grown in micromass culture as described above on glass coverslips (Fisher) for 3 days. Cultures were fixed in 4% paraformaldehyde in PBS, incubated for 30 minutes at room temperature with 1 mg/ml bovine testicular hyaluronidase (type IV, Sigma) in 0.1N sodium acetate (pH 5.5) with protease inhibitors phenymethylsulfonyl fluoride (PMSF, 1 mM), pepstatin (1 µg/ml), leupeptin (1 µg/ml), aprotinin (1 µg/ml), aminocaproic acid (50 mM), benzamidine (5 mM), and EDTA (1 mM), blocked with 10% goat serum in PBS and incubated overnight at 4 C. with primary antibodies against Cyr61 (Yang et al., 1991), fibronectin (Gibco) and tenascin (Gibco). Controls were incubated with anti-Cyr61 antibodies neutralized with 1 µg/ml purified Cyr61. Cultures were subsequently incubated with FITC-conjugated goat-anti-rabbit secondary antibody (Zymed), for 1 hour at room temperature.

For whole mount immunohistochemical staining, mouse embryos from gestational days 10.5 to 12.5 were fixed in 4% paraformaldehyde in PBS, dehydrated in methanol/PBS and stored at −20 C. in absolute methanol. After rehydration, embryos were incubated with anti-Cyr6 1 antibodies as described in Hogan et al., *Development* 120:53–60 (1994), incorporated herein by reference. Controls were incubated with anti-Cyr61 antibodies neutralized with 1 µg/ml purified Cyr61. Immunostained embryos were fixed, cleared and photographed.

Consistent with the transient expression of the Cyr61 mRNA in somitic mesenchymal cells that are differentiating into chondrocytes (O'Brien et al., 1992), the Cyr61 protein was found in the developing embryonic skeletal system. Cyr61 was localized by whole mount immunohistochemical staining to the proximal limb bud mesenchyme in gestational day 10.5 to 12.5 embryos. The Cyr61 protein was localized to the developing vertebrae, the calvarial frontal bone and the first brachial arch, as well as in the heart and umbilical vessels, forming an expression pattern that was consistent with the cyr61 mRNA expression pattern (O'Brien et al., 1992).

Cyr61 protein could be detected by immunoblot analysis in whole limb buds and in micromass cultures of limb bud mesenchymal cells. The level of Cyr61 protein remained at relatively constant levels throughout the 4 day culture period during which chondrogenesis occurred. Using quantitative immunoblot analysis, Cyr61 was estimated to represent approximately 0.03% of total cellular and extracellular proteins in the mesenchymal cell cultures. Cyr61, tenascin (Gibco), and fibronectin were localized to the cartilage nodules by immunofluorescent staining in the mesenchymal cell cultures. Cyr61 and tenascin were primarily localized among the intranodular cells, while a fibrillar staining pattern was also observed around and between the cartilage nodules with anti-fibronectin antibodies. A similar immunofluorescent staining pattern was observed in transverse sections of the micromass cultures for all three antibodies. Together, these results show that endogenous Cyr61 is localized in the developing limb bud mesenchyme, both in vivo and in vivo.

EXAMPLE 24

Chondrogenesis—ECM Signalling Molecules Promote Cell Adhesion

Cyr61 is a secreted protein that mediates the adhesion of fibroblasts and endothelial cells to non-tissue culture-treated plastic surfaces (Kireeva et al., *Mol. Cell. Biol.* 16:1326–1334 [1996]). The attachment of limb bud mesenchymal cells on non-tissue culture dishes coated with BSA. Cyr61, tenascin, and fibronectin, were compared.

Cyr61, fibronectin (Gibco), or tenascin (Gibco) were diluted in 0.1% protease-free bovine serum albumin (BSA) in PBS with 0.5 mM PMSF, to a final concentrations of 10 or 50 µg/ml. A 10 µl drop/well was placed in a non-tissue culture treated 24-well plate (Corning), and incubated at room temperature for 2 hours. The wells were blocked with 1% BSA in PBS for 1 hour at room temperature, and rinsed with serum-free MEM (Modified Eagle's Medium). Limb mesenchymal cells, suspended at $5\times10^5$ cell/ml in serum-free MEM, were added at a volume of 400 µl/well, and incubated at 37 C., 5% $CO_2$ for 1 or 3 hours. At each time point, the cell suspension was removed, the wells were rinsed with MEM and the remaining adherent cells were photographed.

Cells attached poorly to BSA-coated dishes, but adhered as clusters of rounded cells to Cyr61- and tenascin-coated dishes within 1 hour of plating. In contrast, cells plated on fibronectin-coated dishes attached uniformly and started to spread. When cells were allowed to attach for 3 hours, many more adherent cells were observed. Furthermore, intercellular clustering and rounded cell morphology were maintained in cells plated on Cyr61 and tenascin, while cells plated on fibronectin spread to form a monolayer. These observations show that Cyr61 mediates the adhesion and maintenance of a rounded cellular morphology which is conducive for mesenchymal cell chondrogenesis (Zanetti et al., *Dev. Biol.* 139:383–395 [1990]: Solursh et al., *Dev. Bio.* 94:259–264 [1982]), similar to that i previously reported for tenascin (Mackie et al., *J. Cell Biol.* 105:2569–2579 [1987]).

As mentioned previously, ECM signalling molecules such as Cyr61 may be used in methods of screening for modulators of cell adhesion including, but not limited to, the adhesion of chondrocytes. The comparative assay, described above, measures the relative adhesion levels of cells exposed to a combination of an ECM signalling molecule and a suspected modulator of cell adhesion and cells exposed to the ECM signalling molecule alone, whereby the relative levels provide a basis for identifying either a promoter or an inhibitor of cell adhesion.

EXAMPLE 25

Chondrogenesis—ECM Signalling Molecules Promote Cell Aggregation

Since aggregation is an essential step for chondrogenic differentiation (Solursh, M., In *The role of extracellular matrix in development,* pp. 277–303 (Trelstad, R., ed.) (Alan R. Liss, N.Y. 1984)), the ability of Cyr61 to mediate intercellular aggregation in suspension cultures of mesenchymal cells was assessed. The number of cells remaining at various times after isolation were counted. Untreated mesenchymal cells in suspension began to aggregate soon after isolation, as the number of single cells was decreased to 30% of the initial number within a 2 hour incubation period. Cell aggregation was significantly inhibited in cultures treated with affinity-purified anti-Cyr61 antibodies, indicating that endogenous Cyr61 is important for mesenchymal cell aggregation. To rule out the possibility that the affinity-purified anti-Cyr61 antibodies might contain undefined components that interfere with aggregation, anti-Cyr61 antibodies, described above, were pre-incubated with purified Cyr61 protein prior to addition to cells. These pre-incubated antibodies affected cell aggregation no more than the IgG and Cyr61 buffer controls, indicating that the anti-Cyr61 antibodies achieved their inhibition of cell aggregation by neutralizing the endogenous Cyr61 protein of mesenchymal cells.

In addition to the cell aggregation in suspension cultures described above, the effect of Cyr61 on mesenchymal cell aggregation in micromass cultures was also examined. When purified Cyr61 protein (0.3 µg/ml) was added to limb mesenchymal cells, precocious cellular aggregation was observed within 24 hours, unlike control cells which had not received Cyr61. Neither Cyr61-treated nor control cultures had differentiated into cartilage nodules at this time. By culture day 3, the development of internodular cellular condensations between the distinct cartilage nodules was more extensive in Cyr61-treated cultures. These internodular condensations subsequently undergo chondrogenesis, observed as Alcian blue-staining cartilaginous matrix on culture day 4. Taken together, these results indicate that Cyr61 is able to promote cell-cell aggregation, a necessary step in chondrogenesis of mesenchymal cells in micromass culture.

EXAMPLE 26

Chondrogenesis—ECM Signalling Molecules Promote Cell Proliferation

At Some ECM signalling molecules, such as Cyr61, affect chondrogenesis, as revealed by effects on limb bud mesenchyme cells in micromass culture, as described above. Ahrens et al., *Dev. Biol.* 60:69–82 (1977), has reported that these cells, in micromass culture, undergo chondrogenesis in a manner similar to the in vivo process. Mesenchyme cells were obtained from mouse embryonic limb buds by trypsin digestion (1 mg/ml. 1:250 dilution of porcine pancreatic trypsin, Sigma Chemical Co.). Cells were explanted in plastic tissue culture wells and allowed to attach for 2 hours at 37° C., 5% $CO_2$. Cells were then incubated for 24 hours at 37° C. 5% $CO_2$ in MEM with 10% FBS, penicillin (50 U/ml), and streptomycin (50 µg/ml). At this point, the composition of the medium was changed by substituting 4% NuSerum (Collaborative Biomedical Products, Inc.) for 10% FBS. Individual cultures then received Cyr61, fibronectin, heparin, (each at approximately 1 µg/ml) or buffer as a negative control. An additional control was provided by adding a 1:100 dilution of affinity-purified anti-Cyr61 antibody (approximately 13 µg/ml stock solution), elicited and purified by standard techniques. Harlow et al.

Cell proliferation was assessed by the thymidine assay, described above, and by microscopic cell counts. Chondrogenesis was assessed by quantifying the incorporation of [$^{35}$S]-sulfate (ICN Biomedicals, Inc.) into sulfated glycosaminoglycans, and by qualitatively determining the extent of chondrogenesis by cell staining with Alcian Blue. Cultures, described above, were labeled with 2.5 µCi/ml [$^{35}$S]-sulfate for 18 hours, washed twice in PBS, fixed with Kahle's fixative (Pepper et al., *J. Cell Sci.* 109:73–83 [1995]) and stained for 18 hours in 0.5% Alcian Blue, pH 1.0. The extent of chondrogenesis is correlated with the intensity of Alcian Blue staining. San Antonio et al., *Del. Biol.* 115:313–324 (1986). The results show that Cyr61 specifically increased limb bud mesenchyme cell proliferation and aggregation, leading to enhanced chondrogenesis.

In addition to demonstrating that purified Cyr61 enhanced growth factor-induced DNA synthesis in fibroblasts and endothelial cells, the effects of Cyr61 on cell proliferation were directly examined. Cell proliferation during the 4 day culture period was determined by counting cell number and by incorporation of [$^3$H]-thymidine. To determine cell number, cells were harvested by trypsin/EDTA (Sigma) and counted with a Coulter counter. In parallel cultures, [$^3$H]-thymidine (1 µCi/ml; ICN) was added to the media for 18 hours and incorporation in the TCA-insoluble layer was determined by liquid scintillation counting. Purified Cyr61 protein added to limb mesenchymal cells both increased cell number and enhanced DNA synthesis after 2 and 3 days in culture, although the total cell number in Cyr61-treated and Cyr61-untreated cultures leveled off at the same level after 4 days.

The role of Cyr61 in chondrogenesis may also improve the integration of prosthetic devices. For example, skeletal injuries and conditions frequently are treated by the introduction of a prosthesis e.g., hip prosthesis, knee prosthesis. Beyond questions of histocompatibility, the successful implantation of a prosthetic device requires that the foreign element become integrated into the organism's skeletal structure. The capacity of Cyr61 polypeptides to affect cell adhesion, migration, and proliferation, and the ability of Cyr61 polypeptides to induce the differentiation of mesenchyme cells into chondrocytes, should prove valuable in the treatment of skeletal disorders by prosthesis implantation. For example, integration of a prosthetic device by chondrocyte colonization would be promoted by therapeutic treatments involving the administration of Cyr61 in a pharmaceutically acceptable adjuvant, carrier or diluent, using any of the administration routes known in the art or by coating the prosthesis device with Cyr61 polypeptides in a suitable carrier. The carrier may also be a slow-release type vehicle to allow sustained release of the polypeptides.

As noted in previously, the methods of the invention include a method of screening for modulators of cell proliferation, including chondrocytes. A comparison of the relative rates of cell proliferation in the presence of a control comprising an ECM signalling molecule alone (e.g., Cyr61) and in the presence of a combination of an ECM signalling molecule and a suspected modulator of cell proliferation provides a basis for identifying a suspected modulator as a promoter, or inhibitor, of chondrocyte proliferation.

EXAMPLE 27

Chondrogenesis—ECM Signalling Molecules Promote Chondrogenesis

Chondrogenic differentiation was quantitated by incorporation of [$^{35}$S]-sulfate (ICN) into sulfated glycosaminoglycans and assessed qualitatively by Alcian Blue staining. Cultures were radiolabeled with 2.5 µCi/ml [$^{35}$S]-sulfate for 18 hr, fixed with Kahle's fixative and stained with 0.5% Alcian Blue, pH 1.0 (Lev et al., 1964). The extent of chondrogenesis is correlated with the intensity of Alcian Blue staining (San Antonio et al. 1986). [$^{35}$S]-Sulfate incorporation in the fixed cell layer was quantitated by liquid scintillation counting.

Exogenous purified Cyr61 protein promoted limb mesenchymal cell aggregation and resulted in greater Alcian blue-staining cartilaginous regions in micromass cultures, suggestive of a chondrogenesis-promoting effect. This effect was quantified by the incorporation of [$^{35}$S]-sulfate into sulfated glycosaminoglycans (San Antonio et al., 1986) in Cyr61-treated micromass cultures. Exogenous Cyr61 enhanced [$^{35}$S]-sulfate incorporation in a dose-dependent manner, resulting in a 1.5-fold and 3.5-fold increase with 0.3 and 5 µg/ml Cyr61, respectively, and was correlated qualitatively by increased Alcian Blue staining. The increase observed at the 5 µg/ml Cyr61 dose (120 nM) is an underestimation of the actual extent of chondrogenesis, since some of the large cartilage nodules which were formed at this dose detached from the dish. Cultures treated with 10 µg/ml Cyr61 formed a more massive mound of cartilage.

A review of the literature indicated that chondrogenesis in limb mesenchymal cell micromass cultures was increased 2-fold with the addition of 10 µg/ml heparin (San Antonio et al., 1987; Resh et al., 1985) and 3-fold with 50 µg/ml tenascin (200 nM) (Mackie et al., 1987). The results demonstrated that purified Cyr61 was effective at concentrations (10–100 nM) similar to or less than those of other molecules known to promote chondrogenesis in this cell system.

Since a certain threshold cell density must be reached for initial aggregation to occur (Umansky. 1966; Ahrens et al. 1977), embryonic mesenchymal cells plated at low densities are normally unable to differentiate into chondrocytes, although the addition of exogenous factors such as heparin or poly-L-lysine (San Antonio et al., 1986; San Antonio et al., 1987) have been shown to support chondrogenesis in cells plated under these conditions. Therefore, the ability of Cyr61 to promote differentiation of mesenchymal cells plated at densities above and below the threshold for chondrogenesis was assessed. Cells plated at $2.5 \times 10^6$ cell/ml incorporated little [$^{35}$S]-sulfate. However, when Cyr61 was added, these sub-threshold density cultures formed nodules and incorporated sulfate to a level similar to that in cultures plated at $3 \times 10^6$ cells/mil, which supports chondrogenesis. Therefore. Cyr61 can promote chondrogenesis in mesenchymal cells plated at non-chondrogenic. sub-threshold densities.

It is conceivable that when mesenchymal cells are plated in a h high density micromass, the extent of chondrogenesis may be maximal and cannot be enhanced further by exogenous factors, which also may not be accessible to all cells. However, addition of exogenous Cyr61 resulted in a 2-fold enhancement in [$^{35}$S]-sulfate incorporation in cultures plated at densities ranging from 3 to $10 \times 10^6$ cell/ml. Therefore, Cyr61 can further enhance chondrogenesis in high density micromass cultures, which have apparently not reached a maximal degree of differentiation.

It is possible that the increased [$^{35}$S]-sulfate incorporation in Cyr61-treated cultures is at least partly due to an increase in cell number, since Cyr61 also promotes cell proliferation. If this were true, then normalization of sulfate incorporation with respect to cell number would eliminate any differences between control and Cyr61-treated cultures. This was not found to be the case. Cyr61-treated cultures still showed an approximately 2-fold increase in normalized sulfate incorporation over control, indicating that Cyr61 promotes a net increase in chondrogenesis. On culture day 2, the sulfate/cell number ratio was lower in Cyr61-treated cultures compared to controls and is reflective of a low level of [$^{35}$S]-sulfate incorporation relative to cell number, since mesenchymal cells are mostly proliferating rather than differentiating in these early stage cultures (Ede. 1983).

The presence of endogenous Cyr61 in these cells, both in vivo and in vitro, indicates that Cyr61 may indeed function biologically to regulate chondrogenic differentiation. The ability of exogenously added purified Cyr61 to promote intercellular aggregation and to increase [$^{35}$S]-sulfate incorporation and Alcian-blue staining in limb mesenchymal cells demonstrates that Cyr61 can act as a chondrogenesis enhancing factor. As shown above in Example 11, anti-Cyr61 antibodies can neutralize both the cell adhesion and DNA-synthesis enhancement activities of Cyr61. Anti-Cyr61 antibodies were added to the mesenchymal cell culture media or mixed the cell suspension prior to plating. Chondrogenesis was inhibited in the cultures treated with anti-Cyr61 antibodies, as demonstrated by decreases of [$^{35}$S]-sulfate incorporation to 50% and 30% of controls, when antibodies were added to the media, and mixed with the cells, respectively. These observations were correlated with decreased Alcian Blue staining. However, mixing of the anti-Cyr61 antibodies with mesenchymal cells prior to plating resulted in complete detachment in some of the treated cultures within 24 hours.

To eliminate the possibility of an unidentified component in the antibody preparation as a cause of cell detachment, anti-Cyr61 antibody was preincubated with 1 µg/ml purified Cyr61 protein prior to mixing with cells. The inhibition of chondrogenesis in mesenchymal cells mixed with neutralized anti-Cyr61 antibodies was abolished.

Generally, the invention contemplates a method of screening for modulators of chondrogenesis. A comparative assay involves the exposure of chondrocytes to either (a) a combination of a suspected modulator of chondrogenesis and an ECM signalling molecule such as Cyr61, or (b) the ECM signalling molecule alone. Measurements of the relative rates of chondrogenesis then provide a basis for identifying the suspected modulator of chondrogenesis as a promoter or inhibitor of that process.

The results described in this Example demonstrate that endogenous Cyr61 is present in mesenchymal cells and is important for their chondrogenesis. Accordingly, the use of an ECM signalling molecule, such as Cyr61, to induce bone healing is contemplated by the invention. For example, a biologically effective amount of Cyr61 is introduced into a matrix such as a sponge, as described above, and this material is then applied to set bone fractures or used to gather together the fragments of a comminuted bone fracture. A biodegradable matrix may be employed, or the matrix may be removed at an appropriate later time. Alternatively, Cyr61 may be applied directly to bone. In addition, Cyr61 may be applied to inanimate objects such as biocompatible prosthesis, as described in Example 26.

EXAMPLE 28

Genetics

Another way to control the effects of an ECM signalling molecule-related biomaterial is to inactivate it by creating dominant negative mutations in the relevant gene in actively growing and dividing cells. One approach involves the use of recombinant techniques, e.g., to create homozygous mutant genotypes in ex vivo cultures such as HSC cultures. Introduction of these cells into an organism, e.g., a human patient, would then provide an opportunity for the introduced mutant cells to expand and alter the expression of the ECM signalling molecule in vivo. Mutants homozygous for such a mutation could affect the expression of an endogenous wild type ECM signalling molecule in other cells. Heterozygous mutants might produce altered ECM signalling molecules capable of interacting with the wild type ECM signalling molecule, also being expressed, in such a way that the ECM signalling molecule's activities are modulated or abolished.

Furthermore, because of the role played by ECM signalling molecules such as Cyr61 in regulating chondrogenesis (i.e., skeletal development), genetic manipulations that alter the expression of human Cyr61 may prove medically important for prenatal screening methods and gene therapy treatments related to skeletal conditions, in addition to angiogenic conditions. For example, the cyr61 gene is expressed when mesenchymal cells of both ectodermal and mesodermal origins differentiate to form chondrocytes. Thus, one of the roles that Cyr61 might play is to regulate the commitment of mesenchyme cells to chondrocyte cell lineages involved in skeletal development. Consistent with this view, transgenic mice overexpressing cyr61 ectopically are born with skeletal abnormalities. In all cases examined, the presence of the skeletal deformities correlates with expression of the transgene. These results suggest that the human form of Cyr61 may also regulate chondrogenesis and skeletal development. It is also possible that the human cyr61 gene may correspond to a genetic locus already known to affect skeletal development or birth defects relating to bone morphogenesis. Knowledge of the human Cyr61 protein sequence, presented in SEQ ID NO: 4 herein, and the coding sequence of the cDNA, presented in SEQ ID NO: 3 herein, provide the basis for the design of a variety of gene therapy approaches.

This information also provides a basis for the design of probes useful in genotypic analyses. e.g., Restriction Fragment Length Polymorphism analyses. Such analyses are useful in the fields of genetic counselling, e.g., in diagnosing diseases and conditions and the likelihood of their occurrence, as well as in forensic analyses.

By way of example, the materials of the present invention are useful in the prenatal screening for a variety of conditions or disorders, including blood disorders, skeletal abnormalities, and cancerous conditions. Well known techniques for obtaining fetal cells, e.g., amniocentesis, provide the materials needed for diagnosis. In one embodiment of the invention, the fetal cells are expanded and DNA is isolated. In another embodiment, fetal cells are lysed and polymerase chain reactions are performed using oligonucleotide primers according to the invention. Using either approach, the DNA is then subjected to analysis. One analytical approach involves nucleotide sequence determination of particular regions of cyr61 or of the entire gene. The available human Cyr61 coding sequence, presented in SEQ ID NO: 3 herein, facilitates the design of sequencing primers that brings nucleotide sequence analysis into the realm of practical reality. An alternative to nucleotide sequence analysis is an investigation of the expression characteristics of the fetal nucleic acid. The capacity of the fetal nucleic acid to be expressed might be dispositive in the diagnosis of Cyr61-related angiogenic, chondrogenic, or oncogenic disorders.

The invention also comprehends a kit comprising Cyr61. The kits according to the invention provide Cyr61 in a form that is useful for performing the aforementioned methods of the invention. Kits according to the invention contain isolated and purified recombinant human Cyr61 in a suitable buffer, optionally stabilized by the addition of glycerol for storage at −20° C. In addition to the Cyr61 provided in the kit, the invention also contemplates the inclusion of any one of a variety of buffering agents, salts of various types and concentrations, and additional protein stabilizing agents such as DTT, all of which are well known in the art. Other kits according to the invention incorporate isolated and purified murine Cyr61. Kits incorporating a Cyr61 polypeptide and an inhibitory peptide or an anti-Cyr61 antibody, as described above, are also contemplated.

What is claimed is:

1. An antibody that specifically binds to a polypeptide comprising a sequence set forth in SEQ ID NO:4, wherein the antibody binds to a portion of the sequence set forth in SEQ ID NO:4 that is divergent from the sequence set forth in SEQ ID NO:2.

2. An antibody that specifically binds to a polypeptide comprising a fusion protein, said fusion protein comprising a sequence set forth in SEQ ID NO:4, wherein said antibody specifically binds to a portion of the sequence set forth in SEQ ID NO:4, and wherein the portion is divergent from the sequence set forth in SEQ ID NO:2.

3. The antibody according to claim 1, wherein said antibody further comprises a label.

4. The antibody according to claim 3, wherein said label is selected from the group consisting of an enzyme, protein, peptide, antigen, antibody, lectin, carbohydrate, biotin, avidin, radioisotope, toxin and heavy metal.

5. The antibody according to any one of claims 1 or 2–4, wherein said antibody is a humanized antibody.

6. The antibody according to any one of claims 1 or 2–4, wherein said antibody is a CDR-grafted antibody.

7. The antibody according to any one of claims 1 or 2–4, wherein said antibody is a chimeric antibody.

8. The antibody according to any one of claims 1 or 2–4, wherein said antibody is an antibody fragment.

9. The antibody according to any one of claims 1 or 2–4, wherein said antibody is a monoclonal antibody.

10. The antibody according to any one of claims 1 or 2–4, wherein said antibody is a polyclonal antibody.

11. A pharmaceutical composition comprising the antibody according to any one of claims 1 or 2–4, and a pharmaceutically acceptable adjuvant, diluent, or a carrier.

12. A kit comprising the antibody according to any one of claims 1 or 2–4.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 1480 base pairs
      (B) TYPE: nucleic acid
      (C) STRANDEDNESS: single
      (D) TOPOLOGY: linear (ii) MOLECULE TYPE: protein (ix) FEATURE:
      (A) NAME/KEY: CDS
      (B) LOCATION: 180..1316

(ix) FEATURE:
      (A) NAME/KEY: misc_feature
      (D) OTHER INFORMATION: "Mouse cyr61 cDNA coding sequence"

(xi) SEQUENCE DESCRIPTION: SEQ ID NO: 1:

```
CGAGAGCGCC CCAGAGAAGC GCCTGCAATC TCTGCGCCTC CTCCGCCAGC ACCTCGAGAG        60

AAGGACACCC GCCGCCTCGG CCCTCGCCTC ACCGCACTCC GGGCGCATTT GATCCCGCTG       120

CTCGCCGGCT TGTTGGTTCT GTGTCGCCGC GCTCGCCCCG GTTCCTCCTG CGCGCCACA        179

ATG AGC TCC AGC ACC TTC AGG ACG CTC GCT GTC GCC GTC ACC CTT CTC        227
Met Ser Ser Ser Thr Phe Arg Thr Leu Ala Val Ala Val Thr Leu Leu
 1               5                  10                  15

CAC TTG ACC AGA CTG GCG CTC TCC ACC TGC CCC GCC GCC TGC CAC TGC        275
His Leu Thr Arg Leu Ala Leu Ser Thr Cys Pro Ala Ala Cys His Cys
             20                  25                  30

CCT CTG GAG GCA CCC AAG TGC GCC CCG GGA GTC GGG TTG GTC CGG GAC        323
Pro Leu Glu Ala Pro Lys Cys Ala Pro Gly Val Gly Leu Val Arg Asp
```

```
                35                    40                    45
GGC TGC GGC TGC TGT AAG GTC TGC GCT AAA CAA CTC AAC GAG GAC TGC        371
Gly Cys Gly Cys Cys Lys Val Cys Ala Lys Gln Leu Asn Glu Asp Cys
 50                  55                  60

AGC AAA ACT CAG CCC TGC GAC CAC ACC AAG GGG TTG GAA TGC AAT TTC        419
Ser Lys Thr Gln Pro Cys Asp His Thr Lys Gly Leu Glu Cys Asn Phe
 65                  70                  75                  80

GGC GCC AGC TCC ACC GCT CTG AAA GGG ATC TGC AGA GCT CAG TCA GAA        467
Gly Ala Ser Ser Thr Ala Leu Lys Gly Ile Cys Arg Ala Gln Ser Glu
                     85                  90                  95

GGA AGA CCC TGT GAA TAT AAC TCC AGA ATC TAC CAA AAC GGG GAA AGC        515
Gly Arg Pro Cys Glu Tyr Asn Ser Arg Ile Tyr Gln Asn Gly Glu Ser
                    100                 105                 110

TTC CAG CCC AAC TGT AAA CAC CAG TGC ACA TGT ATT GAT GGC GCC GTG        563
Phe Gln Pro Asn Cys Lys His Gln Cys Thr Cys Ile Asp Gly Ala Val
                115                 120                 125

GGC TGC ATT CCT CTG TGT CCC CAA GAA CTG TCT CTC CCC AAT CTG GGC        611
Gly Cys Ile Pro Leu Cys Pro Gln Glu Leu Ser Leu Pro Asn Leu Gly
130                 135                 140

TGT CCC AAC CCC CGG CTG GTG AAA GTC AGC GGG CAG TGC TGT GAA GAG        659
Cys Pro Asn Pro Arg Leu Val Lys Val Ser Gly Gln Cys Cys Glu Glu
145                 150                 155                 160

TGG GTT TGT GAT GAA GAC AGC ATT AAG GAC TCC CTG GAC GAC CAG GAT        707
Trp Val Cys Asp Glu Asp Ser Ile Lys Asp Ser Leu Asp Asp Gln Asp
                    165                 170                 175

GAC CTC CTC GGA CTC GAT GCC TCG GAG GTG GAG TTA ACG AGA AAC AAT        755
Asp Leu Leu Gly Leu Asp Ala Ser Glu Val Glu Leu Thr Arg Asn Asn
                    180                 185                 190

GAG TTA ATC GCA ATT GGA AAA GGC AGC TCA CTG AAG AGG CTT CCT GTC        803
Glu Leu Ile Ala Ile Gly Lys Gly Ser Ser Leu Lys Arg Leu Pro Val
                195                 200                 205

TTT GGC ACC GAA CCG CGA GTT CTT TTC AAC CCT CTG CAC GCC CAT GGC        851
Phe Gly Thr Glu Pro Arg Val Leu Phe Asn Pro Leu His Ala His Gly
210                 215                 220

CAG AAA TGC ATC GTT CAG ACC ACG TCT TGG TCC CAG TGC TCC AAG AGC        899
Gln Lys Cys Ile Val Gln Thr Thr Ser Trp Ser Gln Cys Ser Lys Ser
225                 230                 235                 240

TGC GGA ACT GGC ATC TCC ACA CGA GTT ACC AAT GAC AAC CCA GAG TGC        947
Cys Gly Thr Gly Ile Ser Thr Arg Val Thr Asn Asp Asn Pro Glu Cys
                    245                 250                 255

CGC CTG GTG AAA GAG ACC CGG ATC TGT GAA GTG CGT CCT TGT GGA CAA        995
Arg Leu Val Lys Glu Thr Arg Ile Cys Glu Val Arg Pro Cys Gly Gln
                    260                 265                 270

CCA GTG TAC AGC AGC CTA AAA AAG GGC AAG AAA TGC AGC AAG ACC AAG       1043
Pro Val Tyr Ser Ser Leu Lys Lys Gly Lys Lys Cys Ser Lys Thr Lys
                275                 280                 285

AAA TCC CCA GAA CCA GTC AGA TTT ACT TAT GCA GGA TGC TCC AGT GTC       1091
Lys Ser Pro Glu Pro Val Arg Phe Thr Tyr Ala Gly Cys Ser Ser Val
290                 295                 300

AAG AAA TAC CGG CCC AAA TAC TGC GGC TCC TGC GTA GAT GGC CGG TGC       1139
Lys Lys Tyr Arg Pro Lys Tyr Cys Gly Ser Cys Val Asp Gly Arg Cys
305                 310                 315                 320

TGC ACA CCT CTG CAG ACC AGA ACT GTG AAG ATG CGG TTC CGA TGC GAA       1187
Cys Thr Pro Leu Gln Thr Arg Thr Val Lys Met Arg Phe Arg Cys Glu
                    325                 330                 335

GAT GGA GAG ATG TTT TCC AAG AAT GTC ATG ATG ATC CAG TCC TGC AAA       1235
Asp Gly Glu Met Phe Ser Lys Asn Val Met Met Ile Gln Ser Cys Lys
                    340                 345                 350

TGT AAC TAC AAC TGC CCG CAT CCC AAC GAG GCA TCG TTC GAC TGT AC       1283
```

```
                Cys Asn Tyr Asn Cys Pro His Pro Asn Glu Ala Ser Phe Arg Leu Tyr
                        355                 360                 365

AGC CTA TTC AAT GAC ATC CAC AAG TTC AGG GAC TAAGTGCCTC CAGGGTTC              1336
Ser Leu Phe Asn Asp Ile His Lys Phe Arg Asp
        370                 375

AGTGTGGGCT GGACAGAGGA GAAGCGCAAG CATCATGGAG ACGTGGGTGG GCGGAGGA             1396

AATGGTGCCT TGCTCATTCT TGAGTAGCAT TAGGGTATTT CAAAACTGCC AAGGGGCT             1456

TGTGGACGGA CAGCAGCGCA GCCG                                                  1480

(2) INFORMATION FOR SEQ ID NO: 2:

(i) SEQUENCE CHARACTERISTICS:
        (A) LENGTH: 379 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "Mouse Cyr61 amino acid sequence"

(xi) SEQUENCE DESCRIPTION: SEQ ID NO: 2:

Met Ser Ser Ser Thr Phe Arg Thr Leu Ala Val Ala Val Thr Leu Leu
 1               5                  10                  15

His Leu Thr Arg Leu Ala Leu Ser Thr Cys Pro Ala Ala Cys His Cys
            20                  25                  30

Pro Leu Glu Ala Pro Lys Cys Ala Pro Gly Val Gly Leu Val Arg Asp
        35                  40                  45

Gly Cys Gly Cys Cys Lys Val Cys Ala Lys Gln Leu Asn Glu Asp Cys
    50                  55                  60

Ser Lys Thr Gln Pro Cys Asp His Thr Lys Gly Leu Glu Cys Asn Phe
65                  70                  75                  80

Gly Ala Ser Ser Thr Ala Leu Lys Gly Ile Cys Arg Ala Gln Ser Glu
                85                  90                  95

Gly Arg Pro Cys Glu Tyr Asn Ser Arg Ile Tyr Gln Asn Gly Glu Ser
            100                 105                 110

Phe Gln Pro Asn Cys Lys His Gln Cys Thr Cys Ile Asp Gly Ala Val
        115                 120                 125

Gly Cys Ile Pro Leu Cys Pro Gln Glu Leu Ser Leu Pro Asn Leu Gly
    130                 135                 140

Cys Pro Asn Pro Arg Leu Val Lys Val Ser Gly Gln Cys Cys Glu Glu
145                 150                 155                 160

Trp Val Cys Asp Glu Asp Ser Ile Lys Asp Ser Leu Asp Asp Gln Asp
                165                 170                 175

Asp Leu Leu Gly Leu Asp Ala Ser Glu Val Glu Leu Thr Arg Asn Asn
            180                 185                 190

Glu Leu Ile Ala Ile Gly Lys Gly Ser Ser Leu Lys Arg Leu Pro Val
        195                 200                 205

Phe Gly Thr Glu Pro Arg Val Leu Phe Asn Pro Leu His Ala His Gly
    210                 215                 220

Gln Lys Cys Ile Val Gln Thr Thr Ser Trp Ser Gln Cys Ser Lys Ser
225                 230                 235                 240

Cys Gly Thr Gly Ile Ser Thr Arg Val Thr Asn Asp Asn Pro Glu Cys
                245                 250                 255

Arg Leu Val Lys Glu Thr Arg Ile Cys Glu Val Arg Pro Cys Gly Gln
            260                 265                 270
```

-continued

```
Pro Val Tyr Ser Ser Leu Lys Lys Gly Lys Lys Cys Ser Lys Thr Lys
        275                 280                 285

Lys Ser Pro Glu Pro Val Arg Phe Thr Tyr Ala Gly Cys Ser Ser Val
    290                 295                 300

Lys Lys Tyr Arg Pro Lys Tyr Cys Gly Ser Cys Val Asp Gly Arg Cys
305                 310                 315                 320

Cys Thr Pro Leu Gln Thr Arg Thr Val Lys Met Arg Phe Arg Cys Glu
                325                 330                 335

Asp Gly Glu Met Phe Ser Lys Asn Val Met Met Ile Gln Ser Cys Lys
            340                 345                 350

Cys Asn Tyr Asn Cys Pro His Pro Asn Glu Ala Ser Phe Arg Leu Tyr
        355                 360                 365

Ser Leu Phe Asn Asp Ile His Lys Phe Arg Asp
    370                 375
```

(2) INFORMATION FOR SEQ ID NO: 3:

(i) SEQUENCE CHARACTERISTICS:
        (A) LENGTH: 1418 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 124..1266

(ix) FEATURE:
        (A) NAME/KEY: misc_feature
        (D) OTHER INFORMATION: "Human cyr61 cDNA coding sequence"

(xi) SEQUENCE DESCRIPTION: SEQ ID NO: 3:

```
GGGCGGGCCC ACCGCGACAC CGCGCCGCCA CCCCGACCCC GCTGCGCACG GCCTGTCCGC        60

TGCACACCAG CTTGTTGGCG TCTTCGTCGC CGCGCTCGCC CCGGGCTACT CCTGCGCGCC       120

ACA ATG AGC TCC CGC ATC GCC AGG GCG CTC GCC TTA GTC GTC ACC CTT        168
    Met Ser Ser Arg Ile Ala Arg Ala Leu Ala Leu Val Val Thr Leu
    1               5                  10                  15

CTC CAC TTG ACC AGG CTG GCG CTC TCC ACC TGC CCC GCT GCC TGC CAC        216
Leu His Leu Thr Arg Leu Ala Leu Ser Thr Cys Pro Ala Ala Cys His
                 20                  25                  30

TGC CCC CTG GAG GCG CCC AAG TGC GCG CCG GGA GTC GGG CTG GTC CGG        264
Cys Pro Leu Glu Ala Pro Lys Cys Ala Pro Gly Val Gly Leu Val Arg
             35                  40                  45

GAC GGC TGC GGC TGC TGT AAG GTC TGC GCC AAG CAG CTC AAC GAG GAC        312
Asp Gly Cys Gly Cys Cys Lys Val Cys Ala Lys Gln Leu Asn Glu Asp
         50                  55                  60

TGC AGC AAA ACG CAG CCC TGC GAC CAC ACC AAG GGG CTG GAA TGC AAC        360
Cys Ser Lys Thr Gln Pro Cys Asp His Thr Lys Gly Leu Glu Cys Asn
     65                  70                  75

TTC GGC GCC AGC TCC ACC GCT CTG AAG GGG ATC TGC AGA GCT CAG TCA        408
Phe Gly Ala Ser Ser Thr Ala Leu Lys Gly Ile Cys Arg Ala Gln Ser
 80                  85                  90                  95

GAG GGC AGA CCC TGT GAA TAT AAC TCC AGA ATC TAC CAA AAC GGG GAA        456
Glu Gly Arg Pro Cys Glu Tyr Asn Ser Arg Ile Tyr Gln Asn Gly Glu
                100                 105                 110

AGT TTC CAG CCC AAC TGT CAA CAT CAG TGC ACA TGT ATT GAT GGC GCC        504
Ser Phe Gln Pro Asn Cys Gln His Gln Cys Thr Cys Ile Asp Gly Ala
            115                 120                 125
```

-continued

```
GTG GGC TGC ATT CCT CTG TGT CCC CAA GAA CTA TCT CTC CCC AAC TTG      552
Val Gly Cys Ile Pro Leu Cys Pro Gln Glu Leu Ser Leu Pro Asn Leu
            130                 135                 140

GGC TGT CCC AAC CCT CGG CTG GTC AAA GTT ACC GGG CAG TGC TGC GAG      600
Gly Cys Pro Asn Pro Arg Leu Val Lys Val Thr Gly Gln Cys Cys Glu
145                 150                 155

GAG TGG GTC TGT GAC GAG GAT AGT ATC AAG GAC CCC ATG GAG GAC CAG      648
Glu Trp Val Cys Asp Glu Asp Ser Ile Lys Asp Pro Met Glu Asp Gln
160                 165                 170                 175

GAC GGC CTC CTT GGC AAG GAG CTG GGA TTC GAT GCC TCC GAG GTG GAG      696
Asp Gly Leu Leu Gly Lys Glu Leu Gly Phe Asp Ala Ser Glu Val Glu
            180                 185                 190

TTG ACG AGA AAC AAT GAA TTG ATT GCA GTT GGA AAA GGC AGA TCA CTG      744
Leu Thr Arg Asn Asn Glu Leu Ile Ala Val Gly Lys Gly Arg Ser Leu
                195                 200                 205

AAG CGG CTC CCT GTT TTT GGA ATG GAG CCT CGC ATC CTA TAC AAC CCT      792
Lys Arg Leu Pro Val Phe Gly Met Glu Pro Arg Ile Leu Tyr Asn Pro
            210                 215                 220

TTA CAA GGC CAG AAA TGT ATT GTT CAA ACA ACT TCA TGG TCC CAG TGC      840
Leu Gln Gly Gln Lys Cys Ile Val Gln Thr Thr Ser Trp Ser Gln Cys
225                 230                 235

TCA AAG ACC TGT GGA ACT GGT ATC TCC ACA CGA GTT ACC AAT GAC AAC      888
Ser Lys Thr Cys Gly Thr Gly Ile Ser Thr Arg Val Thr Asn Asp Asn
240                 245                 250                 255

CCT GAG TGC CGC CTT GTG AAA GAA ACC CGG ATT TGT GAG GTG CGG CCT      936
Pro Glu Cys Arg Leu Val Lys Glu Thr Arg Ile Cys Glu Val Arg Pro
            260                 265                 270

TGT GGA CAG CCA GTG TAC AGC AGC CTG AAA AAG GGC AAG AAA TGC AGC      984
Cys Gly Gln Pro Val Tyr Ser Ser Leu Lys Lys Gly Lys Lys Cys Ser
            275                 280                 285

AAG ACC AAG AAA TCC CCC GAA CCA GTC AGG TTT ACT TAC GCT GGA TGT     1032
Lys Thr Lys Lys Ser Pro Glu Pro Val Arg Phe Thr Tyr Ala Gly Cys
            290                 295                 300

TTG AGT GTG AAG AAA TAC CGG CCC AAG TAC TGC GGT TCC TGC GTG GAC     1080
Leu Ser Val Lys Lys Tyr Arg Pro Lys Tyr Cys Gly Ser Cys Val Asp
305                 310                 315

GGC CGA TGC TGC ACG CCC CAG CTG ACC AGG ACT GTG AAG ATG CGG TTC     1128
Gly Arg Cys Cys Thr Pro Gln Leu Thr Arg Thr Val Lys Met Arg Phe
320                 325                 330                 335

CGC TGC GAA GAT GGG GAG ACA TTT TCC AAG AAC GTC ATG ATG ATC CAG     1176
Arg Cys Glu Asp Gly Glu Thr Phe Ser Lys Asn Val Met Met Ile Gln
            340                 345                 350

TCC TGC AAA TGC AAC TAC AAC TGC CCG CAT GCC AAT GAA GCA GCG TTT     1224
Ser Cys Lys Cys Asn Tyr Asn Cys Pro His Ala Asn Glu Ala Ala Phe
            355                 360                 365

CCC TTC TAC AGG CTG TTC AAT GAC ATT CAC AAA TTT AGG GAC                1266
Pro Phe Tyr Arg Leu Phe Asn Asp Ile His Lys Phe Arg Asp
            370                 375                 380

TAAATGCTAC CTGGGTTTCC AGGGCACACC TAGACAAACA AGGGAGAAGA GTGTCAGA       1326

CAGAATCATG GAGAAAATGG GCGGGGGTGG TGTGGGTGAT GGGACTCATT GTAGAAAG       1386

AGCCTTCTCA TTCTTGAGGA GCATTAAGGT AT                                   1418
```

(2) INFORMATION FOR SEQ ID NO: 4:

(i) SEQUENCE CHARACTERISTICS:
        (A) LENGTH: 381 amino acids
        (B) TYPE: amino acid
        (D) TOPOLOGY: linear (ii) MOLECULE TYPE: protein (ix) FEATURE:
    (A) NAME/KEY: misc_feature
    (D) OTHER INFORMATION: "Human Cyr61 amino acid sequence"

(xi) SEQUENCE DESCRIPTION: SEQ ID NO: 4:

```
Met Ser Ser Arg Ile Ala Arg Ala Leu Ala Leu Val Val Thr Leu Leu
 1               5                  10                  15

His Leu Thr Arg Leu Ala Leu Ser Thr Cys Pro Ala Ala Cys His Cys
            20                  25                  30

Pro Leu Glu Ala Pro Lys Cys Ala Pro Gly Val Gly Leu Val Arg Asp
         35                  40                  45

Gly Cys Gly Cys Cys Lys Val Cys Ala Lys Gln Leu Asn Glu Asp Cys
     50                  55                  60

Ser Lys Thr Gln Pro Cys Asp His Thr Lys Gly Leu Glu Cys Asn Phe
 65                  70                  75                  80

Gly Ala Ser Ser Thr Ala Leu Lys Gly Ile Cys Arg Ala Gln Ser Glu
                85                  90                  95

Gly Arg Pro Cys Glu Tyr Asn Ser Arg Ile Tyr Gln Asn Gly Glu Ser
            100                 105                 110

Phe Gln Pro Asn Cys Gln His Gln Cys Thr Cys Ile Asp Gly Ala Val
         115                 120                 125

Gly Cys Ile Pro Leu Cys Pro Gln Glu Leu Ser Leu Pro Asn Leu Gly
    130                 135                 140

Cys Pro Asn Pro Arg Leu Val Lys Val Thr Gly Gln Cys Cys Glu Glu
145                 150                 155                 160

Trp Val Cys Asp Glu Asp Ser Ile Lys Asp Pro Met Glu Asp Gln Asp
                165                 170                 175

Gly Leu Leu Gly Lys Glu Leu Gly Phe Asp Ala Ser Glu Val Glu Leu
            180                 185                 190

Thr Arg Asn Asn Glu Leu Ile Ala Val Gly Lys Gly Arg Ser Leu Lys
         195                 200                 205

Arg Leu Pro Val Phe Gly Met Glu Pro Arg Ile Leu Tyr Asn Pro Leu
    210                 215                 220

Gln Gly Gln Lys Cys Ile Val Gln Thr Thr Ser Trp Ser Gln Cys Ser
225                 230                 235                 240

Lys Thr Cys Gly Thr Gly Ile Ser Thr Arg Val Thr Asn Asp Asn Pro
                245                 250                 255

Glu Cys Arg Leu Val Lys Glu Thr Arg Ile Cys Glu Val Arg Pro Cys
            260                 265                 270

Gly Gln Pro Val Tyr Ser Ser Leu Lys Lys Gly Lys Lys Cys Ser Lys
        275                 280                 285

Thr Lys Lys Ser Pro Glu Pro Val Arg Phe Thr Tyr Ala Gly Cys Leu
    290                 295                 300

Ser Val Lys Lys Tyr Arg Pro Lys Tyr Cys Gly Ser Cys Val Asp Gly
305                 310                 315                 320

Arg Cys Cys Thr Pro Gln Leu Thr Arg Thr Val Lys Met Arg Phe Arg
                325                 330                 335

Cys Glu Asp Gly Glu Thr Phe Ser Lys Asn Val Met Met Ile Gln Ser
            340                 345                 350

Cys Lys Cys Asn Tyr Asn Cys Pro His Ala Asn Glu Ala Ala Phe Pro
        355                 360                 365

Phe Tyr Arg Leu Phe Asn Asp Ile His Lys Phe Arg Asp
    370                 375                 380
```

-continued (2) INFORMATION FOR SEQ ID NO: 5:

(i) SEQUENCE CHARACTERISTICS:
        (A) LENGTH: 2267 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "Fisp12 cDNA coding sequence"

(xi) SEQUENCE DESCRIPTION: SEQ ID NO: 5:

```
GAATTCCGCC GACAACCCCA GACGCCACCG CCTGGAGCGT CCAGACACCA ACCTCCGCCC      60

CTGTCCGAAT CCAGGCTCCA GCCGCGCCTC TCGTCGCCTC TGCACCCTGC TGTGCATCCT     120

CCTACCGCGT CCCGATCATG CTCGCCTCCG TCGCAGGTCC CATCAGCCTC GCCTTGGTGC     180

TCCTCGCCCT CTGCACCCGG CCTGCTACGG GCCAGGACTG CAGCGCGCAA TGTCAGTGCG     240

CAGCCGAAGC AGCGCCGCAC TGCCCCGCCG GCGTGAGCCT GGTGCTGGAC GGCTGCGGCT     300

GCTGCCGCGT CTGCGCCAAG CAGCTGGGAG AACTGTGTAC GGAGCGTGAC CCCTGCGACC     360

CACACAAGGG CCTCTTCTGC GATTTCGGCT CCCCCGCCAA CCGCAAGATT GGAGTGTGCA     420

CTGCCAAAGA TGGTGCACCC TGTGTCTTCG GTGGGTCGGT GTACCGCAGC GGTGAGTCCT     480

TCCAAAGCAG CTGCAAATAC CAATGCACTT GCCTGGATGG GGCCGTGGGC TGCGTGCCCC     540

TATGCAGCAT GGACGTGCGC CTGCCCAGCC CTGACTGCCC CTTCCCGAGA AGGGTCAAGC     600

TGCCTGGGAA ATGCTGCAAG GAGTGGGTGT GTGACGAGCC CAAGGACCGC ACAGCAGTTG     660

GCCCTGCCCT AGCTGCCTAC CGACTGGAAG ACACATTTGG CCCAGACCCA ACTATGATGC     720

GAGCCAACTG CCTGGTCCAG ACCACAGAGT GGAGCGCCTG TTCTAAGACC TGTGGAATGG     780

GCATCTCCAC CCGAGTTACC AATGACAATA CCTTCTGCAG ACTGGAGAAG CAGAGCCGCC     840

TCTGCATGGT CAGGCCCTGC GAAGCTGACC TGGAGGAAAA CATTAAGAAG GGCAAAAAGT     900

GCATCCGGAC ACCTAAAATC GCCAAGCCTG TCAAGTTTGA GCTTTCTGGC TGCACCAGTG     960

TGAAGACATA CAGGGCTAAG TTCTGCGGGG TGTGCACAGA CGGCCGCTGC TGCACACCGC    1020

ACAGAACCAC CACTCTGCCA GTGGAGTTCA AATGCCCCGA TGGCGAGATC ATGAAAAAGA    1080

ATATGATGTT CATCAAGACC TGTGCCTGCC ATTACAACTG TCCTGGGGAC AATGACATCT    1140

TTGAGTCCCT GTACTACAGG AAGATGTACG GAGACATGGC GTAAAGCCAG GAAGTAAGGG    1200

ACACGAACTC ATTAGACTAT AACTTGAACT GAGTTGCATC TCATTTTCTT CTGTAAAAAC    1260

AATTACAGTA GCACATTAAT TTAAATCTGT GTTTTTAACT ACCGTGGGAG GAACTATCCC    1320

ACCAAAGTGA GAACGTTATG TCATGGCCAT ACAAGTAGTC TGTCAACCTC AGACACTGGT    1380

TTCGAGACAG TTTACACTTG ACAGTTGTTC ATTAGCGCAC AGTGCCAGAA CGCACACTGA    1440

GGTGAGTCTC CTGGAACAGT GGAGATGCCA GGAGAAAGAA AGACAGGTAC TAGCTGAGGT    1500

TATTTTAAAA GCAGCAGTGT GCCTACTTTT TGGAGTGTAA CCGGGGAGGG AAATTATAGC    1560

ATGCTTGCAG ACAGACCTGC TCTAGCGAGA GCTGAGCATG TGTCCTCCAC TAGATGAGGC    1620

TGAGTCCAGC TGTTCTTTAA GAACAGCAGT TTCAGCCTCT GACCATTCTG ATTCCAGTGA    1680

CACTTGTCAG GAGTCAGAGC CTTGTCTGTT AGACTGGACA GCTTGTGGCA AGTAAGTTTG    1740

CCTGTAACAA GCCAGATTTT TATTGATATT GTAAATATTG TGGATATATA TATATATATA    1800

TATATTTGTA CAGTTATCTA AGTTAATTTA AAGTCATTTG TTTTTGTTTT AAGTGCTTTT    1860
```

```
GGGATTTTAA ACTGATAGCC TCAAACTCCA AACACCATAG GTAGGACACG AAGCTTATCT    1920

GTGATTCAAA ACAAAGGAGA TACTGCAGTG GGAATTGTGA CCTGAGTGAC TCTCTGTCAG    1980

AACAAACAAA TGCTGTGCAG GTGATAAAGC TATGTATTGG AAGTCAGATT TCTAGTAGGA    2040

AATGTGGTCA AATCCCTGTT GGTGAACAAA TGGCCTTTAT TAAGAAATGG CTGGCTCAGG    2100

GTAAGGTCCG ATTCCTACCA GGAAGTGCTT GCTGCTTCTT TGATTATGAC TGGTTTGGGG    2160

TGGGGGGCAG TTTATTTGTT GAGAGTGTGA CCAAAAGTTA CATGTTTGCA CCTTTCTAGT    2220

TGAAAATAAA GTATATATAT ATTTTTTATA TGAAAAAAAA GGAATTC                  2267
```

(2) INFORMATION FOR SEQ ID NO: 6:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: misc_feature
        (D) OTHER INFORMATION: "Fisp12 amino acid sequence"

(xi) SEQUENCE DESCRIPTION: SEQ ID NO: 6:

```
Met Leu Ala Ser Val Ala Gly Pro Ile Ser Leu Ala Leu Val Leu Leu
 1               5                  10                  15

Ala Leu Cys Thr Arg Pro Ala Thr Gly Gln Asp Cys Ser Ala Gln Cys
            20                  25                  30

Gln Cys Ala Ala Glu Ala Ala Pro His Cys Pro Ala Gly Val Ser Leu
        35                  40                  45

Val Leu Asp Gly Cys Gly Cys Cys Arg Val Cys Ala Lys Gln Leu Gly
    50                  55                  60

Glu Leu Cys Thr Glu Arg Asp Pro Cys Asp Pro His Lys Gly Leu Phe
65                  70                  75                  80

Cys Asp Phe Gly Ser Pro Ala Asn Arg Lys Ile Gly Val Cys Thr Ala
                85                  90                  95

Lys Asp Gly Ala Pro Cys Val Phe Gly Gly Ser Val Tyr Arg Ser Gly
            100                 105                 110

Glu Ser Phe Gln Ser Ser Cys Lys Tyr Gln Cys Thr Cys Leu Asp Gly
        115                 120                 125

Ala Val Gly Cys Val Pro Leu Cys Ser Met Asp Val Arg Leu Pro Ser
    130                 135                 140

Pro Asp Cys Pro Phe Pro Arg Arg Val Lys Leu Pro Gly Lys Cys Cys
145                 150                 155                 160

Lys Glu Trp Val Cys Asp Glu Pro Lys Asp Arg Thr Ala Val Gly Pro
                165                 170                 175

Ala Leu Ala Ala Tyr Arg Leu Glu Asp Thr Phe Gly Pro Asp Pro Thr
            180                 185                 190

Met Met Arg Ala Asn Cys Leu Val Gln Thr Thr Glu Trp Ser Ala Cys
        195                 200                 205

Ser Lys Thr Cys Gly Met Gly Ile Ser Thr Arg Val Thr Asn Asp Asn
    210                 215                 220

Thr Phe Cys Arg Leu Glu Lys Gln Ser Arg Leu Cys Met Val Arg Pro
225                 230                 235                 240

Cys Glu Ala Asp Leu Glu Glu Asn Ile Lys Lys Gly Lys Lys Cys Ile
                245                 250                 255
```

```
Arg Thr Pro Lys Ile Ala Lys Pro Val Lys Phe Glu Leu Ser Gly Cys
            260                 265                 270
Thr Ser Val Lys Thr Tyr Arg Ala Lys Phe Cys Gly Val Cys Thr Asp
        275                 280                 285
Gly Arg Cys Cys Thr Pro His Arg Thr Thr Thr Leu Pro Val Glu Phe
    290                 295                 300
Lys Cys Pro Asp Gly Glu Ile Met Lys Lys Asn Met Met Phe Ile Lys
305                 310                 315                 320
Thr Cys Ala Cys His Tyr Asn Cys Pro Gly Asp Asn Asp Ile Phe Glu
            325                 330                 335
Ser Leu Tyr Tyr Arg Lys Met Tyr Gly Asp Met Ala
            340                 345
```

(2) INFORMATION FOR SEQ ID NO: 7:

(i) SEQUENCE CHARACTERISTICS:
        (A) LENGTH: 2075 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "CTGF cDNA coding sequence"

(xi) SEQUENCE DESCRIPTION: SEQ ID NO: 7:

```
CCCGGCCGAC AGCCCCGAGA CGACAGCCCG GCGCGTCCCG GTCCCCACCT CCGACCACCG      60

CCAGCGCTCC AGGCCCCGCG CTCCCCGCTC GCCGCCACCG CGCCCTCCGC TCCGCCCGCA     120

GTGCCAACCA TGACCGCCGC CAGTATGGGC CCCGTCCGCG TCGCCTTCGT GGTCCTCCTC     180

GCCCTCTGCA GCCGGCCGGC CGTCGGCCAG AACTGCAGCG GGCCGTGCCG GTGCCCGGAC     240

GAGCCGGCGC CGCGCTGCCC GGCGGGCGTG AGCCTCGTGC TGGACGGCTG CGGCTGCTGC     300

CGCGTCTGCG CCAAGCAGCT GGGCGAGCTG TGCACCGAGC GCGACCCCTG CGACCCGCAC     360

AAGGGCCTCT TCTGTGACTT CGGCTCCCCG GCCAACCGCA AGATCGGCGT GTGCACCGCC     420

AAAGATGGTG CTCCCTGCAT CTTCGGTGGT ACGGTGTACC GCAGCGGAGA GTCCTTCCAG     480

AGCAGCTGCA AGTACCAGTG CACGTGCCTG GACGGGGCGG TGGGCTGCAT GCCCCTGTGC     540

AGCATGGACG TTCGTCTGCC CAGCCCTGAC TGCCCCTTCC CGAGGAGGGT CAAGCTGCCC     600

GGGAAATGCT GCGAGGAGTG GGTGTGTGAC GAGCCCAAGG ACCAAACCGT GGTTGGGCCT     660

GCCCTCGCGG CTTACCGACT GGAAGACACG TTTGGCCCAG ACCCAACTAT GATTAGAGCC     720

AACTGCCTGG TCCAGACCAC AGAGTGGAGC GCCTGTTCCA AGACCTGTGG GATGGGCATC     780

TCCACCCGGG TTACCAATGA CAACGCCTCC TGCAGGCTAG AGAAGCAGAG CCGCCTGTGC     840

ATGGTCAGGC CTTGCGAAGC TGACCTGGAA GAGAACATTA GAAGGGCAA AAAGTGCATC     900

CGTACTCCCA AAATCTCCAA GCCTATCAAG TTTGAGCTTT CTGGCTGCAC CAGCATGAAG     960

ACATACCGAG CTAAATTCTG TGGAGTATGT ACCGACGGCC GATGCTGCAC CCCCCACAGA    1020

ACCACCACCC TGCCGGTGGA GTTCAAGTGC CCTGACGGCG AGGTCATGAA GAAGAACATG    1080

ATGTTCATCA AGACCTGTGC CTGCCATTAC AACTGTCCCG GAGACAATGA CATCTTTGAA    1140

TCGCTGTACT ACAGGAAGAT GTACGGAGAC ATGGCATGAA GCCAGAGAGT GAGAGACATT    1200

AACTCATTAG ACTGGAACTT GAACTGATTC ACATCTCATT TTTCCGTAAA AATGATTTCA    1260

GTAGCACAAG TTATTTAAAT CTGTTTTTCT AACTGGGGGA AAAGATTCCC ACCCAATTCA    1320
```

-continued

```
AAACATTGTG CCATGTCAAA CAAATAGTCT ATCTTCCCCA GACACTGGTT TGAAGAATGT    1380

TAAGACTTGA CAGTGGAACT ACATTAGTAC ACAGCACCAG AATGTATATT AAGGTGTGGC    1440

TTTAGGAGCA GTGGGAGGGT ACCGGCCCGG TTAGTATCAT CAGATCGACT CTTATACGAG    1500

TAATATGCCT GCTATTTGAA GTGTAATTGA GAAGGAAAAT TTTAGCGTGC TCACTGACCT    1560

GCCTGTAGCC CCAGTGACAG CTAGGATGTG CATTCTCCAG CCATCAAGAG ACTGAGTCAA    1620

GTTGTTCCTT AAGTCAGAAC AGCAGACTCA GCTCTGACAT TCTGATTCGA ATGACACTGT    1680

TCAGGAATCG GAATCCTGTC GATTAGACTG GACAGCTTGT GGCAAGTGAA TTTGCCTGTA    1740

ACAAGCCAGA TTTTTTAAAA TTTATATTGT AAATATTGTG TGTGTGTGTG TGTGTGTATA    1800

TATATATATA TATGTACAGT TATCTAAGTT AATTTAAAGT TGTTTGTGCC TTTTTATTTT    1860

TGTTTTTAAT GCTTTGATAT TTCAATGTTA GCCTCAATTT CTGAACACCA TAGGTAGAAT    1920

GTAAAGCTTG TCTGATCGTT CAAAGCATGA AATGGATACT TATATGGAAA TTCTGCTCAG    1980

ATAGAATGAC AGTCCGTCAA AACAGATTGT TTGCAAAGGG GAGGCATCAG TGTCTTGGCA    2040

GGCTGATTTC TAGGTAGGAA ATGTGGTAGC TCACG                                2075
```

(2) INFORMATION FOR SEQ ID NO: 8:

(i) SEQUENCE CHARACTERISTICS:
        (A) LENGTH: 349 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: misc_feature
        (D) OTHER INFORMATION: "CTGF amino acid sequence"

(xi) SEQUENCE DESCRIPTION: SEQ ID NO: 8:

```
Met Thr Ala Ala Ser Met Gly Pro Val Arg Val Ala Phe Val Val Leu
 1               5                  10                  15

Leu Ala Leu Cys Ser Arg Pro Ala Val Gly Gln Asn Cys Ser Gly Pro
             20                  25                  30

Cys Arg Cys Pro Asp Glu Pro Ala Pro Arg Cys Pro Ala Gly Val Ser
         35                  40                  45

Leu Val Leu Asp Gly Cys Gly Cys Cys Arg Val Cys Ala Lys Gln Leu
     50                  55                  60

Gly Glu Leu Cys Thr Glu Arg Asp Pro Cys Asp Pro His Lys Gly Leu
 65                  70                  75                  80

Phe Cys Asp Phe Gly Ser Pro Ala Asn Arg Lys Ile Gly Val Cys Thr
                 85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190
```

-continued

```
Thr Met Ile Arg Ala Asn Cys Leu Val Gln Thr Thr Glu Trp Ser Ala
        195                 200                 205
Cys Ser Lys Thr Cys Gly Met Gly Ile Ser Thr Arg Val Thr Asn Asp
        210                 215                 220
Asn Ala Ser Cys Arg Leu Glu Lys Gln Ser Arg Leu Cys Met Val Arg
225                 230                 235                 240
Pro Cys Glu Ala Asp Leu Glu Glu Asn Ile Lys Lys Gly Lys Lys Cys
                245                 250                 255
Ile Arg Thr Pro Lys Ile Ser Lys Pro Ile Lys Phe Glu Leu Ser Gly
                260                 265                 270
Cys Thr Ser Met Lys Thr Tyr Arg Ala Lys Phe Cys Gly Val Cys Thr
        275                 280                 285
Asp Gly Arg Cys Cys Thr Pro His Arg Thr Thr Thr Leu Pro Val Glu
        290                 295                 300
Phe Lys Cys Pro Asp Gly Glu Val Met Lys Lys Asn Met Met Phe Ile
305                 310                 315                 320
Lys Thr Cys Ala Cys His Tyr Asn Cys Pro Gly Asp Asn Asp Ile Phe
                325                 330                 335
Glu Ser Leu Tyr Tyr Arg Lys Met Tyr Gly Asp Met Ala
                340                 345
```

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGGGATCTGT GACGAGCCCA AGGAC                                    25

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGGAATTCGA CCAGGCAGTT GGCTCG                                  26

(2) INFORMATION FOR SEQ ID NO: 11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GGGGATCCTG TGATGAAGAC AGCATT                                  26

(2) INFORMATION FOR SEQ ID NO: 12:

(i) SEQUENCE CHARACTERISTICS:

```
           (A) LENGTH: 26 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 12:

GGGAATTCAA CGATGCATTT CTGGCC                                            26

(2) INFORMATION FOR SEQ ID NO: 13:

(i) SEQUENCE CHARACTERISTICS:
           (A) LENGTH: 21 amino acids
           (B) TYPE: amino acid
           (C) STRANDEDNESS: not relevant
           (D) TOPOLOGY: not relevant (ii) MOLECULE TYPE: peptide (xi) SEQUENCE DESCRIPTION: SEQ ID NO: 13:

Asp Gly Cys Gly Cys Cys Lys Val Cys Ala Lys Gln Leu Asn Glu Asp
1               5                   10                  15

Cys Ser Lys Thr Gln
            20

(2) INFORMATION FOR SEQ ID NO: 14:

(i) SEQUENCE CHARACTERISTICS:
           (A) LENGTH: 21 amino acids
           (B) TYPE: amino acid
           (C) STRANDEDNESS: not relevant
           (D) TOPOLOGY: not relevant (ii) MOLECULE TYPE: peptide (xi) SEQUENCE DESCRIPTION: SEQ ID NO: 14:

Pro Asn Cys Lys His Gln Cys Thr Cys Ile Asp Gly Ala Val Gly Cys
1               5                   10                  15

Ile Pro Leu Cys Pro
            20

(2) INFORMATION FOR SEQ ID NO: 15:

(i) SEQUENCE CHARACTERISTICS:
           (A) LENGTH: 24 amino acids
           (B) TYPE: amino acid
           (C) STRANDEDNESS: not relevant
           (D) TOPOLOGY: not relevant (ii) MOLECULE TYPE: peptide (xi) SEQUENCE DESCRIPTION: SEQ ID NO: 15:

Cys Ile Val Gln Thr Thr Ser Trp Ser Gln Cys Ser Lys Ser Cys Gly
1               5                   10                  15

Thr Gly Ile Ser Thr Arg Val Thr
            20

(2) INFORMATION FOR SEQ ID NO: 16:

(i) SEQUENCE CHARACTERISTICS:
           (A) LENGTH: 26 amino acids
           (B) TYPE: amino acid
           (C) STRANDEDNESS: not relevant
           (D) TOPOLOGY: not relevant (ii) MOLECULE TYPE: peptide
```

-continued

```
        (xi) SEQUENCE DESCRIPTION: SEQ ID NO: 16:

Ile Ser Thr Arg Val Thr Asn Asp Asn Pro Glu Cys Arg Leu Val Lys
1               5                  10                  15

Glu Thr Arg Ile Cys Glu Val Arg Pro Cys
                20                  25

(2) INFORMATION FOR SEQ ID NO: 17:

(i) SEQUENCE CHARACTERISTICS:
            (A) LENGTH: 21 amino acids
            (B) TYPE: amino acid
            (C) STRANDEDNESS: not relevant
            (D) TOPOLOGY: not relevant (ii) MOLECULE TYPE: peptide (xi) SEQUENCE DESCRIPTION: SEQ ID NO: 17:

Lys Tyr Cys Gly Ser Cys Val Asp Gly Arg Cys Cys Thr Pro Leu Gln
1               5                  10                  15

Thr Arg Thr Val Lys
                20
```